United States Patent [19]

Yoshioka et al.

[11] Patent Number: 4,933,355
[45] Date of Patent: Jun. 12, 1990

[54] THIAZOLE DERIVATIVES, THEIR PREPARATION AND THEIR USE IN THE TREATMENT OF DIABETES COMPLICATIONS

[75] Inventors: Takao Yoshioka; Takashi Fujita; Yuichi Aizawa; Tsutomu Kanai; Hiroyoshi Horikoshi, all of Hiromachi, Japan

[73] Assignee: Sankyo Company Limited, Tokyo, Japan

[21] Appl. No.: 337,366

[22] Filed: Apr. 13, 1989

[30] Foreign Application Priority Data

Apr. 14, 1988 [JP] Japan .................................. 63-92027

[51] Int. Cl.$^5$ ................. C07D 417/06; A61K 31/425
[52] U.S. Cl. ..................................... 514/369; 514/212; 514/227.8; 514/236.8; 514/255; 514/326; 540/603; 544/60; 544/133; 544/367; 546/209; 548/183
[58] Field of Search ............. 548/183; 514/369, 227.8, 514/236.8, 212, 255, 326; 540/603; 544/60, 133, 367; 546/209

[56] References Cited

U.S. PATENT DOCUMENTS 4,831,045  5/1989  Tanouchi .......................... 514/369

FOREIGN PATENT DOCUMENTS 316790  5/1989  European Pat. Off. ............ 548/183
179873  7/1988  Japan .................................. 548/183

Primary Examiner—Robert Gerstl
Attorney, Agent, or Firm—Frishauf, Holtz, Goodman & Woodward

[57] ABSTRACT

Compounds of formula (I):

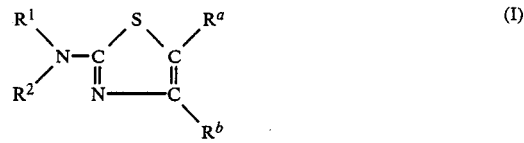

in which: $R^1$ and $R^2$ are independently hydrogen, alkyl, aliphatic hydrocarbon groups having one or two carbon-carbon double or treble bonds, cycloalkyl, aryl, substituted aryl, aralkyl, substituted aralkyl, alkanoyl, alkenyol, cycloalkylcarbonyol, arylcarbonyl, substituted arylcarbonyl, arylalkanoyl, substituted arylalkanoyl, arylalkenoyl, substituted arylalkenoyl, alkoxycarbonyl, aryloxycarbonyl, substituted aryloxycarbonyl, aralkyloxycarbonyl, substituted aralkyloxycarbonyl, optionally substituted carbamoyl or thiocarbamoyol, alkylsulfonyl, haloalkylsulfonyl, arylsulfonyl, substituted arylsulfonyl, alkylthio, arylthio and substituted arylthio, or $R^1$ and $R^2$, together with the nitrogen atom to which they are attached, form a nitrogen-containing heterocyclic group; one of $R^a$ and $R^b$ is hydrogen, alkyl or halogen, and the other of $R^a$ and $R^b$ is a group of formula (II):

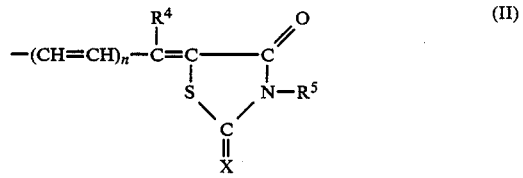

$R^4$ is hydrogen, carboxy, protected carboxy or optionally substituted carbamoyl; $R^5$ is hydrogen, or carboxyalkyl or protected carboxyalkyl in which the alkyl part is $C_1$-$C_6$; n=0, 1 or 2; X is oxygen or sulfur; are useful in the treatment of the complications attendant upon diabetes and may be prepared by condensation of a thiazolidine or rhodanine compound with a compound corresponding to the remainder of the molecule of the compound of formula (I).

37 Claims, No Drawings

THIAZOLE DERIVATIVES, THEIR PREPARATION AND THEIR USE IN THE TREATMENT OF DIABETES COMPLICATIONS

BACKGROUND OF THE INVENTION

The present invention relates to a series of new thiazole derivatives, in which the thiazole ring is attached via an unsaturated carbon chain to a rhodanine or thiazolidine-2,4-dione ring system. The invention also provides a process for preparing the compounds as well as methods and compositions for using them.

The enzyme aldose reductase is implicated in many of the complications of diabetes, and inhibitors of its activity can, therefore, be used in the treatment and prevention of such complications. A number of thiazolidine and/or rhodanine derivatives have been found to have the ability to inhibit the activity of aldose reductase. Thus, certain compounds of this type are disclosed in European Patent Publication Nos. 47,109 and 208,040, and in the published Japanese Patent Application Kokai Nos. 56,175/86, 238,286/87 and 179,873/88 (the latter being published after the priority date hereof).

We have now discovered a new series of thiazole derivatives having a very marked ability to inhibit the activity of aldose reductase, which ability is believed to be significantly better than that of the above-mentioned prior art compounds, from which they differ structurally primarily by virtue of the thiazole group. Moreover, these new derivatives include compounds which, upon oral administration, have been found to combine excellent absorption from the gastro-intestinal tract with very low toxicity.

BRIEF SUMMARY OF INVENTION

It is, therefore, an object of the present invention to provide a new series of compounds which have the ability to inhibit the activity of aldose reductase.

It is a further object of the invention to provide such compounds for use in the treatment of the complications of diabetes.

The compounds of the present invention are thiazole derivatives having the formula (I):

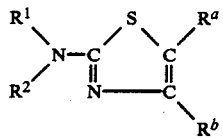

(I)

in which:

$R^1$ and $R^2$ are independently selected from the group consisting of:
hydrogen atoms,
$C_1-C_{12}$ alkyl groups,
$C_3-C_6$ aliphatic hydrocarbon groups having one or two carbon-carbon double or treble bonds,
$C_3-C_8$ cycloalkyl groups,
$C_6-C_{14}$ aryl groups,
substituted $C_6-C_{14}$ aryl groups having at least one substituent selected from the group consisting of substituents (a) defined below,
aralkyl and substituted aralkyl groups with from 1 to 3 aryl parts each of which is $C_6-C_{14}$ and an alkyl part which is $C_1-C_5$, and said substituted aralkyl groups having at least one substituent selected from the group consisting of substituents (a) defined below,
$C_1-C_{12}$ alkanoyl groups,
$C_3-C_{12}$ alkenoyl groups,
$C_4-C_9$ cycloalkylcarbonyl groups,
$C_7-C_{15}$ arylcarbonyl groups,
substituted $C_7-C_{15}$ arylcarbonyl groups having at least one substituent selected from the group consisting of substituents (a) defined below,
arylalkanoyl groups in which the aryl part is $C_6-C_{14}$ and is unsubstituted or has at least one substituent selected from the group consisting of substituents (a) defined below and the alkanoyl part is $C_2-C_6$,
arylalkenoyl groups in which the aryl part is $C_6-C_{14}$ and is unsubstituted or has at least one substituent selected from the group consisting of substituents (a) defined below and the alkenoyl part is $C_3-C_6$,
$C_2-C_7$ alkoxycarbonyl groups,
$C_7-C_{15}$ aryloxycarbonyl groups,
substituted $C_7-C_{15}$ aryloxycarbonyl groups having at least one substituent selected from the group consisting of substituents (a) defined below,
$C_8-C_{20}$ aralkyloxycarbonyl groups,
substituted $C_8-C_{20}$ aralkyloxycarbonyl groups having at least one substituent selected from the group consisting of substituents (a) defined below,
groups of formula $-CONR^6R^7$,
groups of formula $-CSNR^6R^7$,
$C_1-C_6$ alkylsulfonyl groups,
$C_1-C_6$ haloalkylsulfonyl groups,
$C_6-C_{14}$ arylsulfonyl groups,
substituted $C_6-C_{14}$ arylsulfonyl groups having at least one substituent selected from the group consisting of substituents (a) defined below,
$C_1-C_6$ alkylthio groups,
$C_6-C_{14}$ arylthio groups, and
substituted $C_6-C_{14}$ arylthio groups having at least one substituent selected from the group consisting of substituents (a) defined below;
or $R^1$ and $R^2$, together with the nitrogen atom to which they are attached, form a nitrogen-containing heterocyclic group having from 5 to 8 ring atoms, of which 0 or 1 are additional hetero-atoms selected from the group consisting of nitrogen, oxygen and sulfur hetero-atoms, said heterocyclic group being unsubstituted or having at least one substituent selected from the group consisting of substituents (b) defined below, or form such a heterocyclic group fused to at least one benzene or naphthalene ring system which ring system is unsubstituted or has at least one substituent selected from the group consisting of substituents (c) defined below;
one of $R^a$ and $R^b$ represents a hydrogen atom, a $C_1-C_6$ alkyl group or a halogen atom, and the other of $R^a$ and $R^b$ represents a group of formula (II):

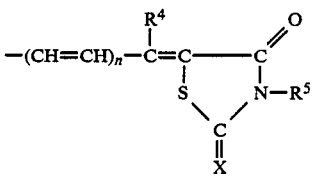

(II)

$R^4$ represents a hydrogen atom, a carboxy group, a protected carboxy group or a group of formula $-CONR^8R^9$;

$R^5$ represents a hydrogen atom, or a carboxyalkyl or protected carboxyalkyl group in which the alkyl part is $C_1-C_6$;

n=0, 1 or 2;

X represents an oxygen or sulfur atom;

$R^6$ and $R^7$ are independently selected from the group consisting of:
hydrogen atoms,
$C_1-C_6$ alkyl groups,
$C_3-C_6$ alkenyl groups,
$C_3-C_8$ cycloalkyl groups,
$C_6-C_{14}$ aryl groups,
substituted $C_6-C_{14}$ aryl groups having at least one substituent selected from the group consisting of substituents (c) defined below,
$C_7-C_{19}$ aralkyl groups,
substituted $C_7-C_{19}$ aralkyl groups having at least one substituent selected from the group consisting of substituents (c) defined below,
$C_1-C_6$ alkylsulfonyl groups,
$C_1-C_6$ haloalkylsulfonyl groups,
$C_6-C_{14}$ arylsulfonyl groups,
substituted $C_6-C_{14}$ arylsulfonyl groups having at least one substituent selected from the group consisting of substituents (c) defined below,
$C_1-C_{12}$ alkanoyl groups,
$C_4-C_9$ cycloalkylcarbonyl groups,
$C_7-C_{15}$ arylcarbonyl groups,
substituted $C_7-C_{15}$ arylcarbonyl groups having at least one substituent selected from the group consisting of substituents (c) defined below;

$R^8$ and $R^9$ are independently selected from the group consisting of hydrogen atoms and $C_1-C_6$ alkyl groups;

substituents (a):
$C_1-C_8$ alkyl groups,
$C_1-C_6$ haloalkyl groups,
$C_6-C_{14}$ aryl groups,
$C_7-C_{19}$ aralkyl groups,
$C_1-C_{12}$ alkanoyl groups,
$C_7-C_{15}$ arylcarbonyl groups,
$C_2-C_7$ alkoxycarbonyl groups,
$C_7-C_{15}$ aryloxycarbonyl groups,
$C_8-C_{20}$ aralkyloxycarbonyl groups,
groups of formula $-CONR^{10}R^{11}$,
groups of formula $-CSNR^{10}R^{11}$,
(where $R^{10}$ and $R^{11}$ are independently selected from the group consisting of hydrogen atoms, $C_1-C_6$ alkyl groups and $C_6-C_{14}$ aryl groups),
groups of formula $-NR^{12}R^{13}$, (where $R^{12}$ and $R^{13}$ are independently selected from the group consisting of hydrogen atoms, $C_1-C_6$ alkyl groups, $C_6-C_{14}$ aryl groups, $C_1-C_6$ alkanoyl groups and $C_7-C_{15}$ arylcarbonyl groups),
halogen atoms,
nitro groups,
cyano groups,
hydroxy groups,
$C_1-C_6$ alkoxy groups,
$C_6-C_{14}$ aryloxy groups,
$C_1-C_{12}$ alkanoyloxy groups,
$C_7-C_{15}$ arylcarbonyloxy groups,
$C_2-C_7$ alkoxycarbonyloxy groups,
$C_7-C_{15}$ aryloxycarbonyloxy groups,
$C_8-C_{20}$ aralkyloxycarbonyloxy groups,
carboxy groups,
sulfo groups, and
sulfamoyl groups;

substituents (b):
oxygen atoms (i.e. to form an oxo group),
halogen atoms,
$C_1-C_6$ alkyl groups,
$C_6-C_{14}$ aryl groups,
substituted $C_6-C_{14}$ aryl groups having at least one substituent selected from the group consisting of substituents (c) defined below,
$C_7-C_{19}$ aralkyl groups,
substituted $C_7-C_{19}$ aralkyl groups having at least one substituent selected from the group consisting of substituents (c) defined below,
$C_1-C_6$ alkanoyl groups,
$C_7-C_5$ arylcarbonyl groups, and
substituted $C_7-C_{15}$ arylcarbonyl groups having at least one substituent selected from the group consisting of substituents (c) defined below;

substituents (c):
$C_1-C_4$ alkyl groups,
$C_1-C_4$ alkoxy groups,
$C_6-C_{10}$ aryl groups,
$C_6-C_{10}$ aryloxy groups,
$C_1-C_6$ alkanoyloxy groups,
halogen atoms,
hydroxy groups,
cyano groups,
trifluoromethyl groups,
carboxy groups, and
nitro groups.

The invention also embraces the pharmaceutically acceptable salts of said compounds of formula (I) and, where said compounds contain a carboxy group, also the esters thereof.

The invention further provides a pharmaceutical composition for the treatment or prevention of complications of diabetes, which comprises at least one compound of said formula (I) or a pharmaceutically acceptable salt or ester thereof in admixture with a pharmaceutically acceptable carrier or diluent.

The invention still further provides a method for the treatment or prophylaxis of the complications of diabetes in a mammal suffering from diabetes, which may be human or non-human, by administering thereto an effective amount of at least one compound of said formula (I) or a pharmaceutically acceptable salt or ester thereof.

The invention also provides processes for preparing the aforesaid compounds, as will be described in detail hereafter.

DETAILED DESCRIPTION OF INVENTION

In the compounds of the present invention, where $R^1$ and/or $R^2$ represents an alkyl group, this may be a straight or branched chain alkyl group having from 1 to 12 carbon atoms, and examples include the methyl, ethyl, propyl, isopropyl, butyl, isobutyl, t-butyl, sec-butyl, pentyl, isopentyl, neopentyl, 2-methylbutyl, 1,1-dimethylpropyl, 1-ethylpropyl, hexyl, isohexyl, neohexyl, 1-methylpentyl, 2-methylpentyl, 3-methylpentyl, 1,3-dimethylbutyl, 2-ethylbutyl, 1,2,2-trimethylpropyl, 1-ethyl-1-methylpropyl heptyl, 1,1-dimethylpentyl, 1-methylhexyl, 2-methylhexyl, 3-methylhexyl, 1,3-dimethylpentyl, 1,4-dimethylpentyl, 1-propylbutyl, 1-ethylpentyl, 1-isopropyl-2-methylpropyl, 2-ethylpentyl, octyl, 1-methylheptyl, 1,5-dimethylhexyl, 1-ethylhexyl, 1-ethyl-3-methylpentyl, 1,1,3,3-tetramethylbutyl, 2-methyloctyl, nonyl, 2-methylnonyl, 2-ethyloctyl, decyl, 2-methyldecyl, 2-ethyldecyl, undecyl and dodecyl groups. Of these, we prefer the $C_1$–$C_8$ alkyl groups, of which the $C_1$–$C_6$ alkyl groups, for example the methyl, ethyl, propyl, isopropyl, butyl, isobutyl, t-butyl, sec-butyl, pentyl, isopentyl, neopentyl, 2-methylbutyl, 1,1-dimethylpropyl, 1-ethylpropyl, hexyl, isohexyl, neohexyl, 1-methylpentyl, 3-methylpentyl, 1,3-dimethylbutyl, 2-ethylbutyl, 1,2,2-trimethylpropyl and 1-ethyl-1-methylpropyl groups are more preferred. The $C_1$–$C_4$ alkyl groups, for example the methyl, ethyl, propyl, isopropyl, butyl, isobutyl and sec-butyl groups are most preferred.

Where $R^1$ and/or $R^2$ represents an aliphatic hydrocarbon group having one or two carbon-carbon double or treble bonds, this may be an alkenyl group, which may be a straight or branched chain alkenyl group having from 3 to 6 carbon atoms, and examples include the allyl, 3-butenyl, 2-butenyl, 4-pentenyl, 3-pentenyl, 2-pentenyl, 3-methyl-2-butenyl, 2,4-pentadienyl, 2-propylallyl, 2,3-dimethyl-2-butenyl, 2-methyl-2-propenyl, 2-methyl-3-pentenyl, 4-methyl-3-pentenyl, 1-methyl-4-pentenyl, 5-hexenyl, 4-hexenyl, 3-hexenyl, 2-hexenyl and 2,4-hexadienyl groups, of which the allyl and 2-methyl-2-propenyl groups are preferred.

Alternatively, the aliphatic hydrocarbon group having one or two carbon-carbon double or treble bonds represented by $R^1$ and/or $R^2$ may be an alkynyl group, which may be a straight or branched chain alkynyl group having from 3 to 6 carbon atoms, and examples include the propargyl, 2-butynyl, 3-butynyl, 1,1-dimethyl-2-propynyl, 2-pentynyl, 3-pentynyl, 4-pentynyl, 1-methyl-2-butynyl, 2-hexynyl, 1-methyl-2-pentynyl, 1-methyl-3-pentynyl, 1,1-dimethyl-2-butynyl and 1,1-dimethyl-3-butynyl groups, of which the propargyl group is preferred.

Where $R^1$ and/or $R^2$ represents a cycloalkyl group, this has from 3 to 8 carbon atoms and examples include the cyclopropyl, cyclobutyl, cyclopentyl, cyclohexyl, cycloheptyl and cyclooctyl groups, of which the $C_3$–$C_6$ cycloalkyl groups are preferred.

Where $R^1$ and/or $R^2$ represents an aryl group, this is a carbocyclic aromatic group which has from 6 to 14 carbon atoms in the aromatic ring system and examples include the phenyl, 1-naphthyl, 2-naphthyl, 1-anthryl, 2-anthryl and 9-anthryl groups, which may be unsubstituted or may have at least one substituent selected from the group consisting of substituents (a), defined above and exemplified below, of which the phenyl and naphthyl groups are more preferred and the phenyl group is most preferred.

Specific examples of substituted aryl groups which may be represented by $R^1$ and/or $R^2$ include the o-, m- or p-aminophenyl, o-, m- or p-(N,N-dimethylamino)phenyl, o-, m- or p-nitrophenyl, o-, m- or p-fluorophenyl, o-, m- or p-chlorophenyl, o-, m- or p-bromophenyl, o-, m- or p-cyanophenyl, o-, m- or p-hydroxyphenyl, o-, m- or p-methoxyphenyl, o-, m- or p-ethoxyphenyl, o-, m- or p-ethoxycarbonylphenyl, o-, m- or p-ethylcarbamoylphenyl, o-, m- or p-pentyloxyphenyl, o-, m- or p-phenoxyphenyl, o-, m- or p-formyloxyphenyl, o-, m- or p-acetoxyphenyl, o-, m- or p-acetamidophenyl, o-, m- or p-carboxyphenyl, o-, m- or p-benzoylaminophenyl, o-, m- or p-ethylaminophenyl, o-, m- or p-phenylaminophenyl, o-, m- or p-benzoyloxyphenyl, o-, m- or p-benzoylphenyl, o-, m- or p-acetylphenyl, o-, m- or p-carbamoylphenyl, o-, m- or p-sulfamoylphenyl, o-, m- or p-methylphenyl, o-, m- or p-ethylphenyl, o-, m- or p-isopropylphenyl, o-, m- or p-biphenyl, o-, m- or p-benzyloxyphenyl, o-, m- or p-trifluoromethylphenyl, 4-fluoro-3-nitrophenyl, 2-bromo-4-methylphenyl, 2-bromo-4,6-difluorophenyl, 2-acetamido-5-trifluoromethylphenyl, 2-ethoxy-4-fluoro-6-nitrophenyl, pentafluorophenyl, 2,4-dibromophenyl, 2,4-difluorophenyl, 2,4,6-tribromophenyl, 4-iodophenyl, 2,3-dimethoxyphenyl, 2,4-dimethoxyphenyl, 3,4-dimethoxyphenyl, 3,4,5-trimethoxyphenyl, 2,6-dimethylphenyl, 2,4-dichlorophenyl, 2,6-dichlorophenyl, 3,4-dichlorophenyl, 3,4-difluorophenyl, 2,5-dichlorophenyl, 2,4,6-trichlorophenyl, 2,4,6-trifluorophenyl, 2,4,5-trifluorophenyl, 2-hydroxy-3,5-dibromophenyl, 2-chloro-4-fluorophenyl, 2-fluoro-4-trifluoromethylphenyl, 2-nitro-4-trifluoromethylphenyl, 2-fluoro-4-chlorophenyl, 4-fluoro-2-trifluoromethylphenyl, 2-hydroxy-3,5-di-t-butylphenyl, 4-hydroxy-3,5-di-t-butylphenyl, 4-hydroxy-3,5-dimethylphenyl, 3,5-dichloro-4-hydroxyphenyl, 2-hydroxy-5-(1,1,3,3-tetramethylbutyl)phenyl, 4-fluoro-1-naphthyl, 4-chloro-1-naphthyl, 4-fluoro-2-naphthyl, 4-chloro-2-naphthyl, 3-hydroxy-2-naphthyl and 4-sulfo-1-naphthyl groups.

Where $R^1$ and/or $R^2$ represents an aralkyl group, the aryl part of this group is a carbocyclic aromatic group which has from 6 to 14 carbon atoms in the aromatic ring system and the aralkyl group may contain from 1 to 3 such aryl groups. The alkyl part is a $C_1$–$C_5$, preferably $C_1$–$C_3$, more preferably $C_1$–$C_2$, alkyl group, which may be any of those alkyl groups having from 1 to 5 carbon atoms exemplified above in relation to rhe alkyl groups which may be represented by $R^1$ and $R^2$. The aralkyl group may be unsubstituted or it may have at least one substituent selected from the group consisting of substituents (a), defined above and exemplified in general terms below. It preferably has a total of from 7 to 19 carbon atoms including the atoms of both the aromatic ring system and the alkyl part, but the number will depend, inter alia, on the nature and number of the aryl groups; the number of aryl groups may be restricted by steric constraints. Examples of the unsubstituted aralkyl groups include the benzyl, 1-phenylethyl, 2-phenylethyl (commonly referred to as "phenethyl"), 1-phenylpropyl, 3-phenylpropyl, 1-phenylbutyl, 4-phenylbutyl, 1-methyl-1-phenylethyl, 1-naphthylmethyl, 2-naphthylmethyl, bis(2-naphthyl)methyl, (1-naphthyl)(phenyl)methyl, 9-anthrylmethyl, diphenylmethyl and triphenylmethyl groups. Examples of the substituted groups include those in which the aryl group of any of the above aralkyl groups is replaced by one of the substituted aryl groups listed above, especially the bis(p-fluorophenyl)methyl and (2-naphthyl)(p-fluorophenyl)methyl groups.

Where $R^1$ and/or $R^2$ represents an alkanoyl having from 1 to 12 carbon atoms, this may be a straight or branched chain group, for example a formyl, acetyl, propionyl, butyryl, isobutyryl, valeryl, hexanoyl, heptanoyl, octanoyl, nonanoyl or dodecanoyl group, of which the $C_1$–$C_6$ alkanoyl groups are preferred.

Where $R^1$ and/or $R^2$ represents an alkenoyl group having from 3 to 12 carbon atoms, this may be a straight or branched chain group, for example an acryloyl, methacryloyl, crotonoyl, isocrotonoyl, oleoyl or elaidoyl group.

Where $R^1$ and/or $R^2$ represents an alicyclic acyl group having from 4 to 9 carbon atoms, i.e. a cycloalkylcarbonyl group, the cycloalkyl part has from 3 to 8 ring carbon atoms and may be any of the cycloalkyl groups exemplified above. Examples include the cyclopropylcarbonyl, cyclobutylcarbonyl, cyclopentylcarbonyl, cyclohexylcarbonyl, cycloheptylcarbonyl and cyclooctylcarbonyl groups.

Where $R^1$ and/or $R^2$ represents an aromatic acyl group having from 7 to 15 carbon atoms, this is an arylcarbonyl group, in which the aryl part is $C_6$–$C_{14}$ and may be unsubstituted or may have at least one substituent selected from the group consisting of substituents (a), defined above and exemplified below; the aryl part may be any of the substituted and unsubstituted aryl groups exemplified above. The benzoyl and substituted benzoyl groups are preferred. Specific examples include the benzoyl, 1-naphthoyl, 2-naphthoyl, 9-anthracenecarbonyl, o-, m- or p-fluorobenzoyl, o-, m- or p-chlorobenzoyl, o-, m- or p-bromobenzoyl, o-, m- or p-methylbenzoyl, o-, m- or p-ethylbenzoyl, o-, m- or p-nitrobenzoyl, o-, m- or p-cyanobenzoyl, o-, m- or p-carboxybenzoyl, o-, m- or p-ethoxycarbonylbenzoyl, o-, m- or p-hydroxybenzoyl, o-, m- or p-methoxybenzoyl, o-, m- or p-ethoxybenzoyl, o-, m- or p-formyloxybenzoyl, o-, m- or p-acetoxybenzoyl, o-, m- or p-phenoxybenzoyl, o-, m- or p-carbamoylbenzoyl, o-, m- or p-sulfamoylbenzoyl, o-, m- or p-trifluoromethyl- benzoyl, o-, m- or p-benzoylbenzoyl, o-, m- or p-phenylbenzoyl, o-, m- or p-aminobenzoyl, o-, m- or p-acetamidobenzoyl, o-, m- or p-benzoylaminobenzoyl, 2,4-dichlorobenzoyl, 3,4-dichlorobenzoyl, 2,5-dichlorobenzoyl, pentafluorobenzoyl, 3,4,5,-trimethoxybenzoyl, 4-hydroxy-3,5-di-t-butylbenzoyl, 2,3-dibromobenzoyl, 3,5-dibromobenzoyl, 3,5-dinitrobenzoyl, 3-nitro-2-naphthoyl and 3-hydroxy-2-anthracenecarbonyl groups.

Where $R^1$ and/or $R^2$ represents an arylalkanoyl group in which the aryl part is $C_6$–$C_{14}$ and is unsubstituted or has at least one substituent selected from the group consisting of substituents (a) and the alkanoyl part is $C_2$–$C_6$, or an arylalkenoyl group in which the aryl part is $C_6$–$C_{14}$ and is unsubstituted or has at least one substituent selected from the group consisting of substituents (a) and the alkenoyl part is $C_3$–$C_6$, the aryl, alkanoyl and alkenoyl parts may be as exemplified above. The aryl part is preferably phenyl. Specific examples of such groups include the phenylacetyl, 3-phenylpropionyl, 4-phenylbutyryl, 5-phenylvaleryl, 6-phenylhexanoyl, hydratropoyl, atropoyl and cinnamoyl groups, and such groups in which the phenyl group has at least one of substituents (a).

Where $R^1$ and/or $R^2$ represents an alkoxycarbonyl group, this may be a straight or branched chain group having, in total, from 2 to 7 carbon atoms and examples include the methoxycarbonyl, ethoxycarbonyl, propoxycarbonyl, isopropoxycarbonyl, butoxycarbonyl, isobutoxycarbonyl, t-butoxycarbonyl, sec-butoxycarbonyl, pentyloxycarbonyl, isopentyloxycarbonyl, neopentyloxycarbonyl, hexyloxycarbonyl and isohexyloxycarbonyl groups.

Where $R^1$ and/or $R^2$ represents an aryloxycarbonyl group, the aryl part may be substituted or unsubstituted and has from 6 to 14 carbon atoms in the aromatic ring. Examples include those in which the aryl group is any one of those aryl groups exemplified above in relation to the aryl groups which may be represented by $R^1$ and $R^2$, preferably phenyl or naphthyl. Specific examples of such groups include the phenoxycarbonyl, 1-naphthyloxycarbonyl and 2-naphthyl- oxycarbonyl groups, as well as such groups having at least one substituent selected from the group consisting of substituents (a), defined above and exemplified below.

Where $R^1$ and/or $R^2$ represents an aralkyloxycarbonyl group, this has, in total, from 8 to 20 carbon atoms, i.e. 1 carbon atom provided by the carbonyl group and from 7 to 19 provided by the aralkyl part. The aralkyl part may be substituted or unsubstituted and any one of those aralkyl groups having from 7 to 19 carbon atoms exemplified above in relation to the aralkyl groups which may be represented by $R^1$ and $R^2$. Specific examples of such groups include the benzyloxycarbonyl, 1-phenylethoxycarbonyl, 2-phenylethoxycarbonyl, 1-phenylpropoxycarbonyl, 4-phenylbutoxycarbonyl, 1-methyl-1-phenylethoxycarbonyl, 2-naphthylmethoxycarbonyl, 9-anthrylmethoxycarbonyl and diphenylmethoxycarbonyl groups.

Where $R^1$ and/or $R^2$ represents a group of formula —$CONR^6R^7$ or a group of formula —$CSNR^6R^7$, the groups represented by $R^6$ and $R^7$ include: hydrogen atoms, $C_1$–$C_6$ alkyl groups, $C_3$–$C_6$ alkenyl groups, $C_3$–$C_8$ cycloalkyl groups, $C_7$–$C_{19}$ aralkyl groups, $C_6$–$C_{14}$ aryl groups which may be substituted or unsubstituted, and, if substituted, have at least one substituent selected from the group consisting of substituents (c), $C_1$–$C_6$ alkylsulfonyl groups, $C_6$–$C_{14}$ arylsulfonyl groups which may be substituted or unsubstituted, and, if substituted, have at least one substituent selected from the group consisting of substituents (c), $C_1$–$C_6$ haloalkanesulfonyl groups, $C_1$–$C_{12}$ alkanoyl groups, $C_4$–$C_9$ cycloalkylcarbonyl groups, $C_7$–$C_{15}$ arylcarbonyl groups and substituted $C_7$–$C_{15}$ arylcarbonyl groups, which may be any of those groups exemplified in relation to the groups which may be represented by $R^1$ and $R^2$. Examples of such carbamoyl groups include the methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, 1-ethylpropylcarbamoyl, pentylcarbamoyl, hexylcarbamoyl, dimethylcarbamoyl, N-butyl-N-methylcarbamoyl, N-ethyl-N-hexylcarbamoyl, allylcarbamoyl, cyclohexylcarbamoyl, phenylcarbamoyl, 1-naphthylcarbamoyl, diphenylcarbamoyl, N-methyl-N-phenylcarbamoyl, o-, m- and p-nitrophenylcarbamoyl, o-, m- and p-fluorophenylcarbamoyl, o-, m- and p-chlorophenylcarbamoyl, o-, m- and p-bromophenylcarbamoyl, o-, m- and p-trifluoromethylphenylcarbamoyl, o-, m- and p-hydroxyphenylcarbamoyl, o-, m- and p-methoxyphenylcarbamoyl, o-, m- and p-ethoxyphenylcarbamoyl, o-, m- and p-phenoxyphenylcarbamoyl, o-, m- and p-formyloxyphenylcarbamoyl, o-, m-and p-acetoxyphenylcarbamoyl, o-, m- and p-carboxyphenylcarbamoyl, o-, m- and p-methylphenylcarbamoyl, o-, m- and p-ethylphenylcarbamoyl, o-, m- and p-isopropylphenylcarbamoyl, o-, m- and p-biphenylcarbamoyl, 2-bromo-4-methylphenylcarbamoyl, 2,4-difluorophenylcarbamoyl, 2,4-dibromophenylcarbamoyl, 4-fluoro-3-nitrophenylcarbamoyl, 2,6-dimethylphenylcarbamoyl, 2,4,6-trifluorophenylcarbamoyl, 2,4-6-tribromophenylcarbamoyl, 4-iodophenylcarbamoyl, 2,3-dimethoxyphenylcarbamoyl, 2,4-dimethoxyphenylcarbamoyl, 3,4-dimethoxyphenylcarbamoyl, 3,4,5-trimethoxyphenylcarbamoyl, 2,4-dichlorophenylcarbamoyl, 3,4-dichlorophenylcarbamoyl, 2,4,6-trichlorophenylcarbamoyl, 2-hydroxy-3,5-dibromophenylcarbamoyl, 2-hydroxy-3.5-di-t-butylphenylcarbamoyl, 4-hydroxy-3,5-di-t-butylphenylcarbamoyl, 4-hydroxy-3,5-dichlorophenylcarbamoyl, 3-hydroxy-2-naphthylcarbamoyl, benzylcarbamoyl, 4-phenylbutylcarbamoyl, 2-phenylethylcarbamoyl, 1-naphthylmethylcarbamoyl, methanesulfonylcarbamoyl, trifluoromethanesulfonylcarbamoyl, benzenesulfonylcarbamoyl, 4-methylbenzenesulfonylcarbamoyl, benzoylcarbamoyl, acetylcarbamoyl and cyclopentylcarbonylcarbamoyl groups.

Examples of such thiocarbamoyl groups include the methyl(thiocarbamoyl), ethyl(thiocarbamoyl), propyl(thiocarbamoyl), isopropyl(thiocarbamoyl), butyl(thiocarbamoyl), isobutyl(thiocarbamoyl), sec-butyl(thiocarbamoyl), t-butyl(thiocarbamoyl), 1-ethylpropyl(thiocarbamoyl), pentyl(thiocarbamoyl), hexyl(thiocarbamoyl), dimethyl(thiocarbamoyl), N-butyl-N-methyl(thiocarbamoyl), N-hexyl-N-ethyl(thiocarbamoyl), allyl(thiocarbamoyl), cyclohexyl(thiocarbamoyl), phenyl(thiocarbamoyl), 1-naphthyl(thiocarbamoyl), N,N-diphenyl(thiocarbamoyl), N-methyl-N-phenyl(thiocarbamoyl), o-, m- and p-nitrophenyl(thiocarbamoyl), o-, m- and p-fluorophenyl(thiocarbamoyl), o-, m- and p-chlorophenyl(thiocarbamoyl), o-, m-and p- bromophenyl(thiocarbamoyl), o-, m- and p-trifluoromethylphenyl(thiocarbamoyl), o-, m- and p-hydroxyphenyl(thiocarbamoyl), o-, m- and p-methoxyphenyl(thiocarbamoyl), o-, m- and p-ethoxyphenyl(thiocarbamoyl), o-, m- and p-phenoxyphenyl(thiocarbamoyl), o-, o- and p-formyloxyphenyl(thiocarbamoyl), o-, m- and p-acetoxyphenyl(thiocarbamoyl), o-, m- and p-carboxyphenyl(thiocarbamoyl), o-, m- and p-methylphenyl(thiocarbamoyl), o-, m- and p-ethylphenyl(thiocarbamoyl), o-, m- and p-isopropylphenyl(thiocarbamoyl), o-, m- and p-biphenyl(thiocarbamoyl), 2-bromo-4-methylphenyl(thiocarbamoyl), 2,4-difluorophenyl(thiocarbamoyl), 2,4-dibromophenyl(thiocarbamoyl), 2,4,6-trifluorophenyl(thiocarbamoyl), 2,4,6-tribromophenyl(thiocarbamoyl), 4-iodophenyl(thiocarbamoyl), 2,3-dimethoxyphenyl(thiocarbamoyl), 2,4-dimethoxyphenyl(thiocarbamoyl), 3,4-dimethoxyphenyl(thiocarbamoyl), 3,4,5-trimethoxyphenyl(thiocarbamoyl), 2,4-dichlorophenyl(thiocarbamoyl), 3,4-dichlorophenyl(thiocarbamoyl), 2,4,6-trichlorophenyl(thiocarbamoyl), 2-hydroxy-3,5-dibromophenyl(thiocarbamoyl), 2-hydroxy-3,5-di-t-butylphenyl(thiocarbamoyl), 4-hydroxy-3,5-di-t-butylphenyl(thiocarbamoyl), 4-hydroxy-3,5-dichlorophenyl(thiocarbamoyl), 3-hydroxy-2-naphthyl(thiocarbamoyl), benzyl(thiocarbamoyl), 4-phenylbutyl(thiocarbamoyl), 2-phenylethyl(thiocarbamoyl), 1-naphthylmethyl(thiocarbamoyl), methanesulfonyl(thiocarbamoyl), trifluoromethanesulfonyl(thiocarbamoyl), benzenesulfonyl(thiocarbamoyl), 4-methylbenzenesulfonyl(thiocarbamoyl), benzoyl(thiocarbamoyl), acetyl(thiocarbamoyl) and cyclopentylcarbonyl(thiocarbamoyl) groups.

Preferably, $R^6$ and $R^7$ represent hydrogen atoms, $C_1$–$C_6$ alkyl groups, $C_3$–$C_6$ alkenyl groups, $C_3$–$C_8$ cycloalkyl groups, $C_6$–$C_{14}$ aryl groups, substituted $C_6$–$C_{14}$ aryl groups having $C_1$–$C_4$ alkyl, $C_1$–$C_4$ alkoxy, halogen, trifluoromethyl and/or nitro groups as substituents, benzyl groups, benzenesulfonyl groups, toluenesulfonyl groups, $C_2$–$C_6$ alkanoyl groups or $C_7$–$C_{11}$ arylcarbonyl groups. More preferably, they represent hydrogen atoms, $C_1$–$C_6$ alkyl groups, allyl groups, cyclohexyl groups, $C_6$–$C_{10}$ aryl groups, substituted $C_6$–$C_{14}$ aryl groups having $C_1$–$C_4$ alkyl, $C_1$–$C_4$ alkoxy, halogen, trifluoromethyl and/or nitro groups as substituents, benzenesulfonyl groups, toluenesulfonyl groups or benzoyl groups.

The most highly preferred groups of formula —$CONR^6R^7$ and —$CSNR^6R^7$ are those wherein $R^6$ is a hydrogen atom and $R^7$ is a $C_6$–$C_{10}$ aryl group, or a $C_6$–$C_{10}$ aryl group substituted with $C_1$–$C_4$ alkyl, $C_1$–$C_4$ alkoxy, halogen, trifluoromethyl and/or nitro.

However, it is preferred that, when $R^6$ represents one of these sulfonyl or acyl groups, $R^7$ should represent a group or atom other than the sulfonyl or acyl group represented by $R^6$.

Where $R^1$ and/or $R^2$ represents a $C_1$–$C_6$ alkylsulfonyl group, a $C_1$–$C_6$ haloalkylsulfonyl group, a $C_6$–$C_{14}$ arylsulfonyl group or a substituted $C_6$–$C_{14}$ arylsulfonyl group, the alkyl, haloalkyl and aryl parts of these groups may be as exemplified for the corresponding groups represented by $R^1$ and $R^2$ or substituents (a). The haloalkyl group preferably has from 1 to 4 carbon atoms, and the aryl group preferably has from 6 to 10 carbon atoms. Specific examples of such sulfonyl groups include the methanesulfonyl, trifluoromethanesulfonyl, benzenesulfonyl and p-toluenesulfonyl groups.

Where $R^1$ and/or $R^2$ represents an alkylthio group or an arylthio group which may be substituted or unsubstituted, the alkyl and aryl parts are as generally exemplified above. The alkylthio group has from 1 to 6 carbon atoms and the aryl group preferably has from 6 to 10 carbon atoms. Examples of such groups include the methylthio, ethylthio, butylthio, hexylthio, phenylthio and tolylthio groups.

Where $R^1$ and $R^2$ together with the nitrogen atom to which they are attached form a nitrogen-containing heterocyclic group as defined above, this preferably has 5 or 6 ring atoms, and may be unsubstituted or may have at least one substituent selected from the substituents (b); and when they form such a heterocyclic group fused to at least one benzene or naphthalene ring system, this is preferably a benzene ring system, and may be unsubstituted or may have at least one substituent selected from the substituents (c). Examples of such heterocyclic groups include the 1-pyrrolidinyl, piperidino, hexamethyleneimino, heptamethyleneimino, morpholino, thiazolidin-3-yl, thiomorpholino, 1-homopiperazinyl, and 1-piperazinyl and 4-substituted-1-piperazinyl groups (wherein the 4-substituent is $C_1$–$C_4$ alkyl, phenyl, benzyl, benzoyl or $C_1$–$C_6$ alkanoyl), as well as groups of formula:

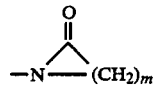

(wherein m is an integer of from 3 to 5), and groups of formula:

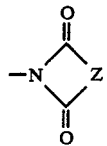

[wherein Z represents, for example, an ethylene, trimethylene, 1,2-phenylene, 4-carboxy-1,2-phenylene, 3,4,5,6-tetrabromo-1,2-phenylene, 1,8-naphthylene, 4-chloro-1,8-naphthylene, 2,2'-biphenyldiyl, vinylene or 1,2-dichlorovinylene group, or a group of formula —$C(CH_3)=C(CH_3)$—].

The preferred heterocyclic groups are the 1-pyrrolidinyl, piperidino, hexamethyleneimino, morpholino, thiomorpholino, 1-homopiperazinyl, 1-piperazinyl, and 1-piperazinyl groups substituted at the 4-position with $C_1$–$C_4$ alkyl, phenyl, acetyl or benzoyl groups.

However, it is preferred that $R^2$ should represent a group other than the above-mentioned acyl, sulfonyl and thio groups represented by $R^1$, when $R^1$ represents an alkanoyl, alkenoyl, cycloalkylcarbonyl, arylcarbonyl, substituted arylcarbonyl, arylalkanoyl, substituted arylalkanoyl, arylalkenoyl, substituted arylalkenoyl, alkoxycarbonyl, aryloxycarbonyl, substituted aryloxycarbonyl, aralkyloxycarbonyl, substituted aralkyloxycarbonyl, groups of formula —CONR$^6$R$^7$ and —CSNR$^6$R$^7$, alkylsulfonyl, arylsulfonyl, substituted arylsulfonyl, alkylthio, arylthio or substituted arylthio.

Where $R^a$ or $R^b$ represents an alkyl group, this may be a straight or branched chain alkyl group having from 1 to 6 carbon atoms, and examples include the methyl, ethyl, propyl, isopropyl, butyl, isobutyl, t-butyl, sec-butyl, pentyl, isopentyl, neopentyl, 2-methylbutyl, 1-ethylpropyl, hexyl, isohexyl, neohexyl, 1-methylpentyl, 2-methylpentyl, 3-methylpentyl, 1,3-dimethylbutyl and 2-ethylbutyl groups.

Where $R^a$ or $R^b$ represents a halogen atom, this may be a fluorine, chlorine, bromine or iodine atom, preferably a chlorine atom or a bromine atom.

However, we prefer that $R^a$ should represent a hydrogen atom, an alkyl group or a halogen atom and $R^b$ should represent a group of formula (II), and more prefer that $R^a$ should represent a hydrogen atom.

Where $R^4$ represents a protected carboxy group, this may be any such group commonly used in compounds of this type, e.g. to form a pharmaceutically acceptable ester group. The precise nature of such a group is not critical to the invention, except that, where the compound is to be used as a medicine, it should be pharmaceutically acceptable. Where the compound is to be used for some other purpose, e.g. as an intermediate in the preparation of another compound, even this limitation does not apply. Examples of such protected carboxy groups include:

- straight and branched chain alkoxycarbonyl groups in which the alkyl part is a $C_1$–$C_8$ alkyl group, more preferably a $C_1$–$C_4$ alkyl group. such as those exemplified in relation to $R^1$ and $R^2$, but most preferably the alkoxycarbonyl groups having from 2 to 5 carbon atoms, such as the methoxycarbonyl, ethoxycarbonyl, propoxycarbonyl, isopropoxycarbonyl, butoxycarbonyl, sec-butoxycarbonyl, isobutoxycarbonyl and t-butoxycarbonyl groups;
- halogenated $C_1$–$C_6$, preferably $C_1$–$C_4$, alkoxycarbonyl groups in which the alkyl part is as defined and exemplified in relation to the alkyl groups which may be represented by $R^1$ and $R^2$, and the halogen atom is chlorine, fluorine, bromine or iodine, such as the 2,2,2-trichloroethoxycarbonyl, 2-haloethoxycarbonyl (e.g. 2-chloroethoxycarbonyl, 2-fluoroethoxycarbonyl, 2-bromoethoxycarbonyl or 2-iodoethoxycarbonyl), 2,2-dibromoethoxycarbonyl and 2,2,2-tribromoethoxycarbonyl groups;
- straight and branched chain alkenyloxycarbonyl and alkadienyloxycarbonyl groups having from 4 to 7 carbon atoms, such as the allyloxycarbonyl, 3-methyl-2-butenyloxycarbonyl, 2-chloroallyloxycarbonyl, 2-methylallyloxycarbonyl and 2,4-hexadienyloxycarbonyl groups;
- cycloalkyloxycarbonyl groups having from 4 to 9 carbon atoms, such as the cyclopropyloxycarbonyl, cyclopentyloxycarbonyl, cyclohexyloxycarbonyl and cyclooctyloxycarbonyl groups;
- aryloxycarbonyl groups having from 7 to 15 carbon atoms, such as the phenoxycarbonyl, 1-naphthyloxycarbonyl, 2-naphthyloxycarbonyl and 1-anthryloxycarbonyl groups, and such groups having at least one substituent selected from the group consisting of carboxylic acylamino groups and the substituents (c) defined above, for example the p-chlorophenoxycarbonyl, p-bromophenoxycarbonyl, m-nitrophenoxycarbonyl, o-carboxyphenoxycarbonyl, p-carbamoylphenoxycarbonyl, p-formyloxyphenoxycarbonyl, 2,4-dichlorophenoxycarbonyl, 3,4-dichlorophenoxycarbonyl, 2,4-dibromophenoxycarbonyl, o-, m- or p-tolyloxycarbonyl and benzamidophenoxycarbonyl groups, of which phenoxycarbonyl groups which may be unsubstituted or substituted are preferred;
- aralkyloxycarbonyl groups in which the aralkyl group has from 7 to 19 carbon atoms, and whose alkyl moiety is straight or branched, which may be unsubstituted or may have at least one substituent selected from the group consisting of substituents (c) defined above, and methylenedioxy groups, such as the benzyloxycarbonyl, 2-phenylethoxycarbonyl, 4-phenylbutoxycarbonyl, 2-naphthylmethoxycarbonyl, 1-phenylbutoxycarbonyl, 1-phenylethoxycarbonyl, 3-phenylpropoxycarbonyl, 2-phenylpropoxycarbonyl, 1-naphthylmethoxycarbonyl, 2-naphthylmethoxycarbonyl, 2-(1-naphthyl)ethoxycarbonyl, 2-(2-naphthyl)ethoxycarbonyl, benzhydryloxycarbonyl (i.e. diphenylmethoxycarbonyl), triphenylmethoxycarbonyl, bis(o-nitrophenyl)methoxycarbonyl, 9-anthrylmethoxycarbonyl, 2,4,6-trimethylbenzyloxycarbonyl, 4-bromobenzyloxycarbonyl, 2-nitrobenzyloxycarbonyl, 4-nitrobenzyloxycarbonyl, 2-nitrobenzyloxycarbonyl, 4-methoxybenzyloxycarbonyl and piperonyloxycarbonyl groups, of which benzyloxycarbonyl groups which may be unsubstituted or substituted are preferred;
- phenacyloxycarbonyl groups, which may be unsubstituted or have at least one substituent selected from the group consisting of substituents (a) defined and exemplified above, for example the phenacyloxycarbonyl group itself or the p-bromophenacyloxycarbonyl group; geranyloxycarbonyl groups;
- 1-(aliphatic acyloxy)$C_1$–$C_4$ alkoxycarbonyl groups, in which the acyl group is preferably an alkanoyl or a cycloalkylcarbonyl group. and is more preferably a $C_2$–$C_6$ alkanoyl or a $C_4$–$C_7$ cycloalkylcarbonyl group, such as the acetoxymethoxycarbonyl, 1-acetoxyethoxycarbonyl, propionyloxymethoxycarbonyl, butyryloxymethoxycarbonyl, isobutyryloxymethoxycarbonyl, pivaloyloxymethoxycarbonyl, 1-pivaloyloxyethoxycarbonyl and cyclohexylcarbonyloxymethoxycarbonyl groups;
- 1-(alkoxycarbonyloxy)$C_1$–$C_4$ alkoxycarbonyl groups, in which the alkoxy part is $C_1$–$C_6$, preferably $C_1$–$C_4$, such as the methoxycarbonyloxymethoxycarbonyl, 1-methoxycarbonyloxyethoxycarbonyl, 1-ethoxycarbonyloxyethoxycarbonyl, 1-propoxycarbonyloxyethoxycarbonyl, 1-isopropoxycarbonyloxyethoxycarbonyl, 1-butoxycarbonyloxyethoxycarbonyl and 1-isobutoxycarbonyloxyethoxycarbonyl groups;
- alkoxymethoxycarbonyl groups, in which the alkoxy part is $C_1$–$C_6$, preferably $C_1$–$C_4$, and may itself be substituted by a single unsubstituted alkoxy group, such as the methoxymethoxycarbonyl, ethoxymethoxycarbonyl, propoxymethoxycarbonyl, isopropoxymethoxycarbonyl, butoxymethoxycarbonyl and methoxyethoxymethoxycarbonyl groups; and other groups capable of being hydrolyzed in vivo under physiological conditions (which include e.g. the pivaloyloxymethoxycarbonyl, acetoxymethoxycarbonyl and methoxymethoxycarbonyl groups referred to above) as well as, for example, the phthalidyl, phthalidyloxycarbonyl, indanyloxycarbonyl, (2-oxo-5-methyl-1,3-dioxolen-4-yl)methoxycarbonyl and (2-oxo-5-phenyl-1,3-dioxolen-4-yl)methoxycarbonyl groups.

Of the protected carboxy groups, alkoxycarbonyl groups and benzyloxycarbonyl groups are preferred, and alkoxycarbonyl groups are more preferred.

Where $R^4$ represents a group of formula $-CONR^8R^9$, this is a substituted or unsubstituted carbamoyl group, and the alkyl groups which may be represented by $R^8$ and $R^9$ may be any of those having from 1 to 6 carbon atoms exemplified above. Examples include the carbamoyl, methylcarbamoyl, ethylcarbamoyl, propylcarbamoyl, isopropylcarbamoyl, butylcarbamoyl, sec-butylcarbamoyl, isobutylcarbamoyl, t-butylcarbamoyl, pentylcarbamoyl, hexylcarbamoyl, dimethylcarbamoyl, diethylcarbamoyl and N-butyl-N-methylcarbamoyl.

However, $R^4$ most preferably represents a hydrogen atom or a protected carboxy group.

Where $R^5$ represents a carboxyalkyl group, the alkyl part of this may be a straight or branched chain alkyl group having from 1 to 6, preferably from 1 to 3, carbon atoms (and more preferably one carbon atom) and a carboxy substituent. and examples include the carboxymethyl, 1-carboxyethyl, 2-carboxyethyl, 3-carboxypropyl, 1-carboxy-1-methylethyl, 1-carboxypropyl, 2-carboxypropyl, 4-carboxybutyl, 3-carboxy-2-methylpropyl, 1-carboxypentyl, 5-carboxypentyl and 6-carboxyhexyl groups.

Where $R^5$ represents a protected carboxyalkyl group, the carboxyalkyl group itself may be as defined and exemplified above, and the protecting group for the carboxy group may be any of those protecting groups forming part of the protected carboxy group represented by $R^4$.

Of the protecting groups, the alkyl and aralkyl groups and the groups capable of being hydrolyzed in vivo are preferred.

Examples of the substituents (a) include:

$C_1$–$C_8$ alkyl groups, $C_6$–$C_{14}$ aryl groups, $C_7$–$C_{19}$ aralkyl groups, $C_1$–$C_{12}$ (or, as appropriate, $C_1$–$C_6$) alkanoyl groups, $C_7$–$C_{15}$ arylcarbonyl groups, $C_2$–$C_7$ alkoxycarbonyl groups, $C_7$–$C_{15}$ aryloxycarbonyl groups and $C_8$–$C_{20}$ aralkyloxycarbonyl groups, in all cases for example such as those exemplified above in relation to $R^1$ and $R^2$;

$C_1$–$C_6$ haloalkyl groups, in which the alkyl part is as defined and exemplified in relation to the alkyl groups which may be represented by $R^1$ and $R^2$, and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl group;

halogen atoms, such as chlorine, fluorine, bromine or iodine; and $C_1$–$C_6$ alkoxy groups, $C_6$–$C_{14}$ aryloxy groups, $C_1$–$C_{12}$ alkanoyloxy groups, $C_7$–$C_{15}$ arylcarbonyl)oxy groups, $C_2$–$C_7$ alkoxycarbonyloxy groups, $C_7$–$C_{15}$ aryloxycarbonyloxy groups and $C_8$–$C_{20}$ aralkyloxycarbonyloxy groups, respectively having a $C_1$–$C_6$ alkyl, $C_6$–$C_{14}$ aryl, $C_1$–$C_{12}$ alkanoyl, $C_7$–$C_{15}$ arylcarbonyl, $C_2$–$C_7$ alkoxycarbonyl, $C_7$–$C_{15}$ aryloxycarbonyl or $C_8$–$C_{20}$ aralkyloxycarbonyl portion for example such as those exemplified above in relation to $R^1$ and $R^2$;

and these examples also apply, when appropriate, to the groups $R^{10}$, $R^{11}$, $R^{12}$ and $R^{13}$.

The preferred substituents (a) are $C_1$–$C_8$ alkyl groups, trifluoromethyl groups, $C_6$–$C_{10}$ aryl groups, $C_7$–$C_{12}$ aralkyl groups, $C_1$–$C_6$ alkanoyl groups, $C_7$–$C_{11}$ arylcarbonyl groups, $C_2$–$C_7$ alkoxycarbonyl groups, carbamoyl groups, mono- or di-$C_2$–$C_7$ alkylcarbamoyl groups, mono- or di-$C_7$–$C_{11}$ arylcarbamoyl groups, thiocarbamoyl groups, mono- or di- $C_2$–$C_7$ alkylthiocarbamoyl groups, mono-or di- $C_7$–$C_{11}$ arylthiocarbamoyl groups, mono- or di-$C_1$–$C_6$ alkylamino groups, mono- or diphenylamino groups, mono- $C_1$–$C_6$ alkanoylamino groups, mono-benzoylamino groups, halogen atoms, nitro groups, cyano groups, hydroxy groups, $C_1$–$C_6$ alkoxy groups, phenoxy groups, $C_1$–$C_6$ alkanoyloxy groups, $C_2$–$C_7$ alkoxycarbonyloxy groups, benzoyloxy groups and carboxy groups. More preferred are $C_1$–$C_6$ alkyl groups, trifluoromethyl groups, phenyl groups, halogen atoms and $C_1$–$C_6$ alkoxy groups; and $C_1$–$C_4$ alkyl groups, $C_1$–$C_4$ alkoxy groups, halogen atoms and trifluoromethyl groups are most preferred.

Examples of the substituents (b) include $C_1$–$C_6$ alkyl groups, halogen atoms, $C_6$–$C_{14}$ aryl groups, $C_7$–$C_{19}$ aralkyl groups, $C_1$–$C_6$ alkanoyl groups and $C_7$–$C_{15}$ arylcarbonyl groups, in all cases for example such as those exemplified above in relation to $R^1$ and $R^2$, of which $C_1$–$C_4$ alkyl groups, phenyl groups, benzyl groups, $C_1$–$C_6$ alkanoyl groups and benzoyl groups are preferred.

Examples of the substituents (c) include:

$C_1$–$C_4$ alkyl, $C_6$–$C_{10}$ aryl, $C_6$–$C_{10}$ aryloxy and $C_1$–$C_6$ alkanoyloxy groups, for example such as those exemplified above in relation to $R^1$ and $R^2$ or substituents (a);

$C_1$–$C_4$ alkoxy groups, for example methoxy, ethoxy, propoxy, isopropoxy, butoxy, isobutoxy, t-butoxy and sec-butoxy groups and halogen atoms, such as chlorine, fluorine, bromine or iodine.

The preferred substituents (c) are $C_1$–$C_4$ alkyl groups, $C_1$–$C_4$ alkoxy groups, halogen atoms, triflouromethyl groups and nitro groups.

A preferred class of compounds of the present invention are those compounds of formula (I), in which:

$R^1$ and $R^2$ are independently selected from the group consisting of:

hydrogen atoms, $C_1$–$C_8$ alkyl groups, $C_3$–$C_6$ alkenyl groups, $C_3$–$C_8$ cycloalkyl groups, $C_6$–$C_{14}$ aryl groups, substituted $C_6$–$C_{14}$ aryl groups having at least one substituent selected from the group consisting of substituents ($a^1$) defined below, aralkyl and substituted aralkyl groups with from 1 to 3 aryl parts each of which is $C_6$–$C_{10}$ and an alkyl part which is $C_1$–$C_3$, and said substituted aralkyl groups having at least one substituent selected from the group consisting of substituents (a¹) defined below, C$_1$–C$_6$ alkanoyl groups, benzoyl groups, substituted benzoyl groups having at least one substituent selected from the group consisting of substituents (a¹) defined below, C$_2$–C$_7$ alkoxycarbonyl groups, groups of formula —CONR$^{6'}$R$^{7'}$, groups of formula —CSNR$^{6'}$R$^{7'}$, benzenesulfonyl groups, and toluenesulfonyl groups, or R$^1$ and R$^2$, together with the nitrogen atom to which they are attached, form a nitrogen-containing heterocyclic group having from 5 to 6 ring atoms, of which 0 or 1 are additional hetero-atoms selected from the group consisting of nitrogen, oxygen and sulfur hetero-atoms, said heterocyclic group being unsubstituted or having at least one substituent selected from the group consisting of substituents (b¹) defined below, or form such a heterocyclic group fused to at least one benzene ring system which ring system is unsubstituted or has at least one substituent selected from the group consisting of substituents (c¹) defined below;

one of R$^a$ and R$^b$ represents a hydrogen atom, and the other of R$^a$ and R$^b$ represents a group of formula (II), defined above;

R$^4$ represents a hydrogen atom, a C$_2$–C$_5$ alkoxycarbonyl group or a benzyloxycarbonyl group;

R$^5$ represents a hydrogen atom, a carboxymethyl group or a protected carboxymethyl group. in which the protecting group is a C$_1$–C$_4$ alkyl group, a benzyl group or the groups capable of being hydrolyzed in vivo;

n=0 or 1;

X represents a sulfur atom;

R$^{6'}$ and R$^{7'}$ are independently selected from the group consisting of:

hydrogen atoms,

C$_1$–C$_6$ alkyl groups,

C$_3$–C$_6$ alkenyl groups.

C$_3$–C$_8$ cycloalkyl groups,

C$_6$–C$_{14}$ aryl groups.

substituted C$_6$–C$_{14}$ aryl groups having at least one substituent selected from the group consisting of substituents (c¹) defined below, benzyl groups, benzenesulfonyl groups, toluenesulfonyl groups, C$_2$–C$_6$ alkanoyl groups, and C$_7$–C$_{11}$ arylcarbonyl groups, substituents (a¹):

C$_1$–C$_6$ alkyl groups, trifluoromethyl groups,

C$_6$–C$_{10}$ aryl groups,

C$_7$–C$_{12}$ aralkyl groups,

C$_1$–C$_6$ alkanoyl groups,

C$_7$–C$_{11}$ arylcarbonyl groups,

C$_2$–C$_7$ alkoxycarbonyl groups, groups of formula —CONR$^{10'}$R$^{11'}$, groups of formula —CSNR$^{10'}$R$^{11'}$, (where R$^{10'}$ and R$^{11'}$ are independently selected from the group consisting of hydrogen atoms, C$_1$–C$_6$ alkyl groups and C$_6$–C$_{10}$ aryl groups), groups of formula —NR$^{12'}$R$^{13'}$, (where R$^{12'}$ and R$^{13'}$ are independently selected from the group consisting of hydrogen atoms, C$_1$–C$_6$ alkyl groups, phenyl groups, C$_1$–C$_6$ alkanoyl groups and benzoyl groups).

halogen atoms, nitro groups, cyano groups, hydroxy groups,

C$_1$–C$_6$ alkoxy groups, phenoxy groups,

C$_1$–C$_6$ alkanoyloxy groups, benzoyloxy groups,

C$_2$–C$_7$ alkoxycarbonyloxy groups, and carboxy groups;

substituents (b¹):

oxygen atoms (i.e. to form an oxo group),

C$_1$–C$_4$ alkyl groups, phenyl groups, benzyl groups,

C$_1$–C$_6$ alkanoyl groups, and benzoyl groups;

substituents (c¹):

C$_1$–C$_4$ alkyl groups,

C$_1$–C$_4$ alkoxy groups, halogen atoms, trifluoromethyl groups, and nitro groups;

provided that, when R$^1$ represents said alkanoyl, benzoyl, substituted benzoyl, alkoxycarbonyl, benzenesulfonyl or toluenesulfonyl group or said group of formula —CONR$^{6'}$R$^{7'}$ or —CSNR$^{6'}$R$^{7'}$, then R$^2$ represents said hydrogen atom, or said alkyl, alkenyl, cycloalkyl, aryl, substituted aryl, aralkyl or substituted aralkyl group;

and pharmaceutically acceptable salts and esters thereof.

More preferred compounds of the present invention are those compounds of formula (Ia):

$$\begin{array}{c} R^2 \diagdown \quad \diagup S \diagdown \quad H \\ N-C \quad C-R^4 \\ R^1 \diagup \quad \| \quad \| \quad | \\ N \text{———} C-C=C \text{———} C=O \\ \diagdown S \diagup \quad | \\ \diagdown C \diagup N-R^5 \\ \| \\ S \end{array} \quad (Ia)$$

in which:

R$^1$ and R$^2$ are independently selected from the group consisting of:

hydrogen atoms,

C$_1$–C$_6$ alkyl groups,

C$_3$–C$_6$ alkenyl groups,

C$_3$–C$_6$ cycloalkyl groups, phenyl groups, naphthyl groups, substituted phenyl groups and substituted naphthyl groups having at least one substituent selected from the group consisting of substituents (a²) defined below, C$_7$–C$_{19}$ aralkyl groups, substituted C$_7$–C$_{19}$ aralkyl groups having at least one substituent selected from the group consisting of substituents (a²) defined below.

C$_2$–C$_6$ alkanoyl groups, benzoyl groups, substituted benzoyl groups having at least one substituent selected from the group consisting of substituents (a²) defined below,
groups of formula —CONR⁶″R⁷″, and
groups of formula —CSNR⁶″R⁷″,
or $R^1$ and $R^2$, together with the nitrogen atom to which they are attached, form a 1-pyrrolidinyl, piperidino, hexamethyleneimino, morpholino, thiomorpholino or 1-piperazinyl group which is unsubstituted or has at least one substituent selected from the group consisting of substituents (b²) defined below;

$R^4$ represents a hydrogen atom or a $C_2$-$C_5$ alkoxycarbonyl group;

$R^5$ represents a hydrogen atom, a carboxymethyl group or a protected carboxymethyl group, in which the protecting group is preferably a $C_1$-$C_4$ alkyl group, a benzyl group or the groups capable of being hydrolyzed in vivo;

$R^{6″}$ and $R^{7″}$ are independently selected from the group consisting of:
hydrogen atoms,
$C_1$-$C_6$ alkyl groups,
allyl groups,
cyclohexyl groups,
$C_6$-$C_{10}$ aryl groups,
substituted $C_6$-$C_{10}$ aryl groups having at least one substituent selected from the group consisting of substituents (c²) defined below,
benzenesulfonyl groups,
toluenesulfonyl groups, and
benzoyl groups, substituents (a²):
$C_1$-$C_6$ alkyl groups,
trifluoromethyl groups,
phenyl groups,
halogen atoms, and
$C_1$-$C_6$ alkoxy groups;

substituents (b²):
$C_1$-$C_4$ alkyl groups,
phenyl groups,
benzyl groups,
$C_1$-$C_6$ alkanoyl groups, and
benzoyl groups;

substituents (c²):
$C_1$-$C_4$ alkyl groups,
$C_1$-$C_4$ alkoxy groups,
halogen atoms,
nitro groups, and
trifluoromethyl groups;

provided that, when $R^1$ represents a hydrogen atom, $R^2$ represents the said groups other than a hydrogen atom, and when $R^1$ represents said alkanoyl, benzoyl or substituted benzoyl group or said group of formula —CONR⁶″R⁷″ or —CSNR⁶″R⁷″, then $R^2$ represents said hydrogen atom or said alkyl, alkenyl, cycloalkyl, phenyl, naphthyl, substituted phenyl, substituted naphthyl, aralkyl or substituted aralkyl group;

and pharmaceutically acceptable salts and esters thereof.

Still more preferred compounds of the present invention are those compounds of formula (Ia), defined above, in which:

$R^1$ and $R^2$ are independently selected from the group consisting of:
hydrogen atoms,
$C_1$-$C_4$ alkyl groups,
$C_3$-$C_6$ alkenyl groups.
$C_3$-$C_6$ cycloalkyl groups,
phenyl groups,
substituted phenyl groups having at least one substituent selected from the group consisting of $C_1$-$C_4$ alkyl groups, $C_1$-$C_4$ alkoxy groups, halogen atoms and trifluoromethyl groups,
monoarylcarbamoyl and monoaryl(thiocarbamoyl) groups in which the aryl group is a $C_6$-$C_{10}$ carbocyclic aryl group which is unsubstituted or has at least one substituent selected from the group consisting of $C_1$-$C_4$ alkyl groups, $C_1$-$C_4$ alkoxy groups, halogen atoms, trifluoromethyl groups and nitro groups, $R^4$ represents a hydrogen atom or a $C_2$-$C_5$ alkoxycarbonyl group;

$R^5$ represents a hydrogen atom, a carboxymethyl group or a protected carboxymethyl group, in which the protecting group is preferably a $C_1$-$C_4$ alkyl group, a benzyl group or one of the groups capable of being hydrolyzed in vivo;

provided that, when $R^1$ represents a hydrogen atom, $R^2$ represents the said groups other than a hydrogen atom, and when $R^1$ represents said monoarylcarbamoyl or monoarylthiocarbamoyl group, $R^2$ represents said hydrogen atom or said alkyl, alkenyl, phenyl or substituted phenyl group;

and pharmaceutically acceptable salts and esters thereof.

The most preferred compounds of the present invention are those compounds of formula (Ib):

$$\begin{array}{c}
R^2 \quad\quad\quad S \quad\quad H \\
\backslash \quad\quad / \quad \backslash \quad / \\
N-C \quad\quad C \quad R^4 \quad\quad O \\
/ \quad \parallel \quad\quad \parallel \quad | \quad\quad \parallel \\
H \quad\quad N\text{------}C-C=C\text{------}C \\
\quad\quad\quad\quad | \quad\quad\quad \backslash \quad / \\
\quad\quad\quad\quad S \quad\quad\quad N-R^5 \\
\quad\quad\quad\quad \backslash \quad / \\
\quad\quad\quad\quad\quad C \\
\quad\quad\quad\quad\quad \parallel \\
\quad\quad\quad\quad\quad S
\end{array} \quad (Ib)$$

in which:
$R^2$ represents a $C_1$-$C_4$ alkyl group, a $C_3$-$C_6$ alkenyl group, a phenyl group, a substituted phenyl group having at least one substituent selected from the group consisting of $C_1$-$C_4$ alkyl groups, $C_1$-$C_4$ alkoxy groups, halogen atoms and trifluoromethyl groups, a phenylcarbamoyl group or a phenyl(thiocarbamoyl) group in which the phenyl group is unsubstituted or has at least one substituent selected from the group consisting of $C_1$-$C_4$ alkyl groups, $C_1$-$C_4$ alkoxy groups, halogen atoms, trifluoromethyl groups and nitro groups, $R^4$ represents a hydrogen atom or a $C_2$-$C_5$ alkoxycarbonyl group;

$R^5$ represents a carboxymethyl group;

and pharmaceutically acceptable salts and esters thereof.

In the compounds of the present invention, from 1 to 3 double bonds are present between the thiazole ring and the thiazolidine or rhodanine ring; and the compounds of the present invention can, therefore, form various stereoisomers. These individual stereoisomers, as well as mixtures thereof, all form part of the present invention. Furthermore, when $R^5$ represents a hydrogen atom in the compound of formula (I), tautomerism occurs between the nitrogen atom and the adjacent carbonyl group, and such tautomers are also included in the present invention. The compounds of the invention may contain one or more carboxy groups and can, therefore, form salts which may, where the compounds are intended for therapeutic use, be pharmaceutically acceptable salts. Examples of such salts include:

salts with alkali or alkaline earth metals, such as the sodium, potassium, magnesium or calcium salts;

salts with other metals, such as the aluminum, iron and cobalt salts;

the ammonium salts;

quaternary ammonium salts, for example the tetramethylammonium, tetraethylammonium, benzyltriethylammonium and phenyltriethylammonium salts;

salts with alkylamines, cycloalkylamines or aralkylamines, such as the methylamine, ethylamine, dimethylamine, diethylamine, trimethylamine, triethylamine, N-methylhexylamine, cyclopentylamine, dicyclohexylamine, benzylamine, dibenzylamine, α-phenylethylamine and ethylenediamine salts;

salts with heterocyclic amines, wherein the heterocyclic group is unsubstituted or has at least one $C_1$–$C_4$ alkyl substituent, for example the piperidine, morpholine, pyrrolidine, piperazine, pyridine, 1-methylpiperazine and 4-ethylmorpholine salts; and salts with amines containing a hydrophilic group, such as the monoethanolamine, ethyldiethanolamine and 2-amino-1-butanol salts.

The compounds of the present invention may also be basic in character as they necessarily contain several nitrogen atoms; they may, therefore, also form acid addition salts with suitable acids. Examples of acids include: hydrochloric acid, sulfuric acid, nitric acid and phosphoric acid; and organic carboxylic and sulfonic acids, such as acetic acid, succinic acid, maleic acid, fumaric acid, malic acid, glutamic acid, aspartic acid, p-toluenesulfonic acid and methanesulfonic acid.

Examples of specific compounds of the invention are given in the following formulae (I-1) to (I-4), in which the substituents are as defined in the corresponding one of Tables 1 to 4 [i.e. Table 1 relates to formula (I-1), Table 2 relates to formula (I-2) and so on]. Formula (I-4) also relates to the compounds listed in Table 5, where $R^1$ and $R^2$ together form the group shown in the column headed $R^1$–$R^2$. In the Tables, the following abbreviations are used:

| | |
|---|---|
| Ac | acetyl |
| All | allyl |
| Ant | anthryl |
| Boz | benzoyl |
| Bu | butyl |
| cBu | cyclobutyl |
| iBu | isobutyl |
| tBu | t-butyl |
| Buc | butoxycarbonyl |
| iBuc | isobutoxycarbonyl |
| tBuc | t-butoxycarbonyl |
| Bz | benzyl |
| Bzc | benzyloxycarbonyl |
| Bzhy | benzhydryl |
| Bzs | benzenesulfonyl |
| Cam | carboxymethyl |
| Car | carbamoyl |
| Et | ethyl |
| Etc | ethoxycarbonyl |
| Hx | hexyl |
| cHx | cyclohexyl |
| Me | methyl |
| Mec | methoxycarbonyl |

-continued

| | |
|---|---|
| Mes | methanesulfonyl |
| Np | naphthyl |
| Npc | naphthyloxycarbonyl |
| Oc | octyl |
| Ph | phenyl |
| Phc | phenoxycarbonyl |
| Phy | phenylene. e.g. 1,2-Phy = 1,2-phenylene |
| Piv | pivaloyl |
| cPn | cyclopentyl |
| nPn | neopentyl |
| Pr | propyl |
| cPr | cyclopropyl |
| iPr | isopropyl |
| Prc | propoxycarbonyl |
| iPrc | isopropoxycarbonyl |
| iPre | isopropenyl |
| Prg | propargyl (= 2-propynyl) |
| Sam | sulfamoyl |
| Sty | styryl |
| Tfm | trifluoromethyl |
| Tol | tolyl |
| Tos | p-toluenesulfonyl |
| Vin | vinyl |

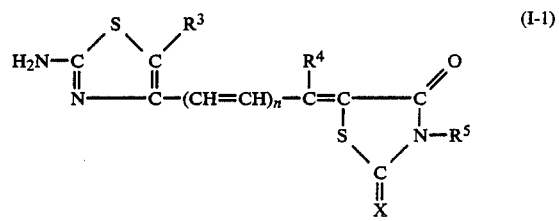

(I-1)

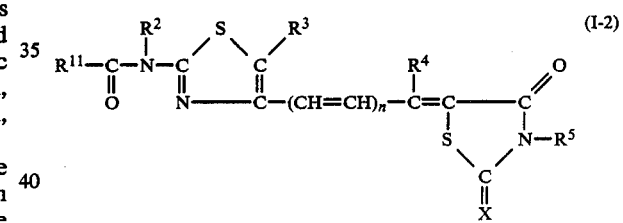

(I-2)

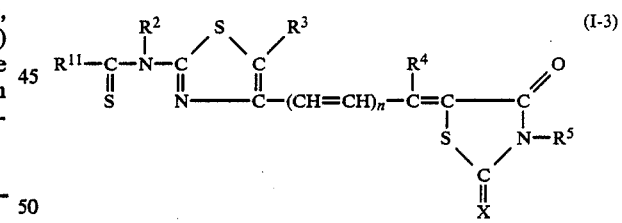

(I-3)

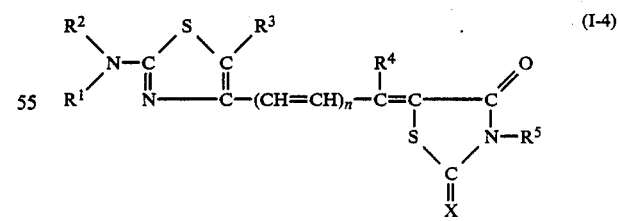

(I-4)

TABLE 1

| Cpd. No. | $R^3$ | $R^4$ | $R^5$ | n | X |
|---|---|---|---|---|---|
| 1-1 | H | H | H | 0 | O |
| 1-2 | H | H | H | 0 | S |
| 1-3 | H | H | Cam | 0 | O |
| 1-4 | H | H | Cam | 0 | S |
| 1-5 | H | H | Cam | 1 | S |

TABLE 1-continued

| Cpd. No. | R³ | R⁴ | R⁵ | n | X |
|---|---|---|---|---|---|
| 1-6 | H | H | (tBuc)Me | 0 | O |
| 1-7 | H | Etc | Cam | 0 | S |
| 1-8 | H | —COOH | Cam | 0 | S |
| 1-9 | H | iPrc | (tBuc)Me | 0 | S |
| 1-10 | H | Mec | Cam | 0 | S |
| 1-11 | H | diiPrCar | Cam | 0 | S |
| 1-12 | H | Etc | (Bzc)Me | 0 | S |

TABLE 2

| Cpd. No. | R¹¹ | R² | R³ | R⁴ | R⁵ | n | X |
|---|---|---|---|---|---|---|---|
| 2-1 | Me | H | H | Etc | Cam | 0 | S |
| 2-2 | tBu | H | H | iBuc | Cam | 0 | S |
| 2-3 | cPn | H | H | H | Cam | 1 | O |
| 2-4 | cHx | H | H | Etc | Cam | 0 | S |
| 2-5 | cHx | Ph | H | H | Cam | 0 | S |
| 2-6 | Vin | H | H | Etc | Cam | 1 | O |
| 2-7 | iPre | cHx | H | EtCar | Cam | 0 | S |
| 2-8 | Sty | H | H | Etc | Cam | 0 | S |
| 2-9 | Sty | H | H | H | Cam | 0 | O |
| 2-10 | Sty | H | H | Car | H | 0 | S |
| 2-11 | Me | H | H | Etc | Cam | 0 | O |
| 2-12 | Ph | H | H | Etc | Cam | 0 | S |
| 2-13 | Ph | H | H | Car | H | 0 | S |
| 2-14 | Ph | Ph | H | Etc | H | 0 | S |
| 2-15 | Ph | H | H | H | Cam | 1 | O |
| 2-16 | Ph | H | H | H | H | 0 | O |
| 2-17 | Ph | H | H | Car | Cam | 0 | O |
| 2-18 | 2-Np | H | H | Etc | Cam | 0 | S |
| 2-19 | 1-Np | Pr | H | diEtCar | Cam | 0 | S |
| 2-20 | 9-Ant | H | H | Car | Cam | 0 | S |
| 2-21 | 4-ClPh | H | H | Etc | Cam | 0 | S |
| 2-22 | 4-BrPh | H | H | H | Cam | 0 | O |
| 2-23 | 2-HOOCPh | Et | H | H | Cam | 0 | S |
| 2-24 | 3,5-diBrPh | H | H | Etc | Cam | 0 | S |
| 2-25 | 2,5-diClPh | H | H | Etc | Cam | 0 | S |
| 2-26 | 3,4-diClPh | H | H | H | Cam | 0 | O |
| 2-27 | pentaFPh | H | H | H | H | 0 | S |
| 2-28 | 4-PhOPh | H | H | Etc | Cam | 0 | S |
| 2-29 | —NHPh | H | H | Etc | Cam | 0 | S |
| 2-30 | —NHPh | H | H | Etc | H | 0 | S |
| 2-31 | —NHPh | H | H | —COOH | H | 0 | S |
| 2-32 | —NHPh | H | H | Phc | Cam | 0 | S |
| 2-33 | —NHPh | H | H | Car | Cam | 0 | S |
| 2-34 | —N(Me)Ph | H | H | BuCar | H | 0 | O |
| 2-35 | —NPh₂ | H | H | Etc | Cam | 0 | S |
| 2-36 | —NPh₂ | H | H | H | Cam | 1 | O |
| 2-37 | —NPh₂ | H | H | H | H | 0 | O |
| 2-38 | —N(All)Ph | H | H | EtCar | Cam | 0 | S |
| 2-39 | —NHPh | H | H | H | H | 0 | S |
| 2-40 | —NHPh | H | H | H | H | 0 | O |
| 2-41 | —NHPh | H | H | H | Cam | 0 | S |
| 2-42 | —NHPh | H | H | H | Cam | 0 | O |
| 2-43 | —NHPh | H | H | H | H | 1 | S |
| 2-44 | —NHPh | H | H | H | H | 1 | O |
| 2-45 | —NHPh | H | H | H | Cam | 1 | S |
| 2-46 | —NHPh | H | H | Etc | H | 1 | S |
| 2-47 | —NH-1-Np | H | H | Etc | Cam | 0 | S |
| 2-48 | —NH-1-Np | H | H | —COOH | H | 0 | S |
| 2-49 | —NH-1-Np | H | H | iPrc | Cam | 1 | S |
| 2-50 | —NH-1-Np | H | H | Car | Cam | 0 | O |
| 2-51 | —NH-1-Np | H | H | BuCar | (1-PivOETc)Me | 0 | S |
| 2-52 | —N(1-Np)cHx | H | H | Etc | Cam | 0 | S |
| 2-53 | —N(1-Np)All | H | H | Car | Cam | 0 | S |
| 2-54 | —N(1-Np)Hx | H | H | MeCar | H | 0 | S |
| 2-55 | —NHPh | H | H | iBuc | Cam | 0 | S |
| 2-56 | —NHPh | H | H | —COOH | Cam | 0 | S |
| 2-57 | —NHPh | H | H | Etc | (1-iPrcOEtc)Me | 0 | S |
| 2-58 | —NHPh | H | H | Etc | (Etc)Me | 0 | S |
| 2-59 | —NHPh | H | H | Etc | (NaOOC)Me | 0 | S |
| 2-60 | —NHPh | H | H | Etc | (Mec)Me | 0 | S |
| 2-61 | —NHPh | H | H | Etc | (iPrc)Me | 0 | S |
| 2-62 | —NHPh | H | H | H | (Buc)Me | 0 | S |
| 2-63 | —NHPh | H | H | Etc | (Bzc)Me | 0 | S |
| 2-64 | p-TosNH— | H | H | Etc | Cam | 0 | S |
| 2-65 | p-TosNH— | H | H | Car | Cam | 0 | S |
| 2-66 | p-TosNH— | H | H | H | H | 1 | O |
| 2-67 | —NHMe | iBu | H | MeCar | Cam | 0 | S |
| 2-68 | —NEt₂ | H | H | H | H | 0 | S |
| 2-69 | —NHtBu | H | H | Prc | Cam | 0 | S |
| 2-70 | —NHHx | H | H | Etc | H | 0 | O |

TABLE 2-continued

| Cpd. No. | R11 | R2 | R3 | R4 | R5 | n | X |
|---|---|---|---|---|---|---|---|
| 2-71 | —NHBz | H | H | Etc | Cam | 0 | S |
| 2-72 | —NH(4-ClPh) | H | H | Etc | Cam | 0 | S |
| 2-73 | —NH(4-ClPh) | H | H | iBuc | Cam | 1 | S |
| 2-74 | —NH(3,4-diClPH) | H | H | Etc | Cam | 0 | S |
| 2-75 | —NH(4-BrPh) | H | H | Etc | Cam | 0 | S |
| 2-76 | —NH(4-FPh) | H | H | Etc | Cam | 0 | S |
| 2-77 | —NH(3,5-diCl-4-(HOPh) | H | H | Etc | Cam | 0 | S |
| 2-78 | —NH(3-CNPh) | Hx | H | Car | Cam | 0 | O |
| 2-79 | —NH(4-PhOPh) | H | H | Etc | Cam | 0 | S |
| 2-80 | —NH(3,4,5-tri-MeOPh) | H | H | Etc | Cam | 0 | S |
| 2-81 | —NH(3,5-ditBu-4-HOPh) | H | H | Car | Cam | 0 | S |
| 2-82 | —NH(3-FPh) | H | H | Etc | Cam | 0 | S |
| 2-83 | —NH(2-FPh) | H | H | Etc | Cam | 0 | S |
| 2-84 | —NH(4-FPh) | H | H | iBuc | Cam | 0 | S |
| 2-85 | —NH(4-MeOPh) | H | H | Etc | Cam | 0 | S |
| 2-86 | —NH(3-MeOPH) | H | H | Etc | Cam | 0 | S |
| 2-87 | —NH(2-MeOPh) | H | H | Etc | Cam | 0 | S |
| 2-88 | —NH(4-F-3-NO2Ph) | H | H | Etc | Cam | 0 | S |
| 2-89 | —NH(4-TfmPh) | H | H | Etc | Cam | 0 | S |
| 2-90 | —NH(2,4-diFPh) | H | H | Etc | Cam | 0 | S |
| 2-91 | —NH(4-FPh) | H | H | Etc | Cam | 1 | S |
| 2-92 | —NH(2,4,6-triFPh) | H | H | Etc | Cam | 0 | S |
| 2-93 | —NH(4-NO2Ph) | H | H | Etc | Cam | 0 | S |
| 2-94 | —NH(2-TfmPh) | H | H | Etc | Cam | 0 | S |
| 2-95 | —NHcHx | H | H | Etc | Cam | 0 | S |
| 2-96 | —NHMe | H | H | Etc | Cam | 0 | S |
| 2-97 | —NH(2,6-diMePh) | H | H | Etc | Cam | 0 | S |
| 2-98 | —NH(2-ClPh) | H | H | Etc | Cam | 0 | S |
| 2-99 | —NH(4-BrPh) | H | H | H | Cam | 1 | S |
| 2-100 | —NH(4-FPh) | H | H | Etc | (NaOOC)Me | 0 | S |
| 2-101 | —NH(2-FPh) | H | H | (E)Etc | (Etc)Me | 0 | S |
| 2-102 | —NH(2-FPh) | H | H | (Z)Etc | (Etc)Me | 0 | S |
| 2-103 | —NH(4-FPh) | H | H | (E)Etc | (Etc)Me | 0 | S |
| 2-104 | —NH(4-FPh) | H | H | (Z)Etc | (Etc)Me | 0 | S |
| 2-105 | —NH(4-MePh) | H | H | Etc | Cam | 0 | S |
| 2-106 | —NH2 | H | H | Etc | Cam | 0 | S |
| 2-107 | —NH2 | H | H | H | Cam | 0 | S |
| 2-108 | —NHBoz | H | H | Etc | Cam | 0 | S |
| 2-109 | —NHBoz | H | H | H | Cam | 0 | S |

TABLE 3

| Cpd. No. | R11 | R2 | R3 | R4 | R5 | n | X |
|---|---|---|---|---|---|---|---|
| 3-1 | —NHPh | H | H | Etc | Cam | 0 | S |
| 3-2 | —NHPh | H | H | iBuc | Cam | 1 | O |
| 3-3 | —NHPh | H | H | —COOH | H | 0 | S |
| 3-4 | —N(Me)Ph | iPr | H | H | Cam | 0 | S |
| 3-5 | —N(Me)Ph | Et | H | Mec | H | 0 | O |
| 3-6 | —N(1-Np)Ph | H | H | Car | Cam | 0 | S |
| 3-7 | —NH-1-Np | H | H | Etc | Cam | 0 | S |
| 3-8 | —N(1-Np)Me | H | H | Etc | Cam | 0 | S |
| 3-9 | —NH-1-Np | H | H | Car | Cam | 1 | S |
| 3-10 | —NH(4-ClPh) | H | H | Etc | Cam | 0 | S |
| 3-11 | —NH(4-ClPh) | H | H | Car | Cam | 0 | S |
| 3-12 | —NH(4-ClPh) | Me | H | H | Cam | 1 | O |
| 3-13 | —NH(4-MeOPh) | H | H | EtCar | H | 0 | O |
| 3-14 | —NH(4-PhPh) | Et | H | H | Cam | 0 | S |
| 3-15 | —NH(4-iPrPh) | H | H | H | Cam | 0 | S |
| 3-16 | —NH(3-AcOPh) | H | H | H | Cam | 0 | S |
| 3-17 | —NH(4-FPh) | H | H | Etc | Cam | 0 | S |
| 3-18 | —NH(4-CNPh) | nPn | H | Car | Cam | 0 | O |
| 3-19 | —NH(4-EtOPh) | Pr | H | Etc | H | 0 | S |
| 3-20 | —NH(2-NO2Ph) | Hx | H | Etc | Cam | 0 | S |
| 3-21 | —NH(2-FPh) | H | H | Etc | Cam | 0 | S |
| 3-22 | —NH(2-TfmPh) | H | H | Etc | Cam | 0 | S |
| 3-23 | —NH(2,4,6-triFPh) | H | H | Etc | Cam | 0 | S |
| 3-24 | —NHPh | H | H | Etc | (Etc)Me | 0 | S |
| 3-25 | —NH(4-ClPh) | H | H | Etc | (Etc)Me | 0 | S |
| 3-26 | —NHBoz | H | H | Etc | Cam | 0 | S |
| 3-27 | —NHBoz | H | H | H | Cam | 0 | S |
| 3-28 | —NH2 | H | H | Etc | Cam | 0 | S |
| 3-29 | —NH2 | H | H | H | Cam | 0 | S |
| 3-30 | —NHBoz | H | H | —COOH | Cam | 0 | S |

TABLE 4

| Cpd. No. | R1 | R2 | R3 | R4 | R5 | n | X |
|---|---|---|---|---|---|---|---|
| 4-1 | Ph | H | H | Etc | Cam | 0 | S |
| 4-2 | 4-ClPh | H | H | Etc | Cam | 0 | S |
| 4-3 | 4-BrPh | H | H | Etc | Cam | 0 | S |
| 4-4 | 4-FPh | H | H | Etc | Cam | 0 | S |
| 4-5 | 4-CNPh | Ph | H | H | H | 1 | O |
| 4-6 | 2-MeOPh | H | H | Etc | Cam | 1 | S |
| 4-7 | 3-EtPh | Et | H | iBuc | Cam | 1 | S |
| 4-8 | 2,4-diClPh | H | H | Etc | Cam | 0 | S |
| 4-9 | 3,5-diBr-2-HOPh | H | H | H | Cam | 1 | S |

TABLE 4-continued

| Cpd. No. | R¹ | R² | R³ | R⁴ | R⁵ | $n$ | X |
|---|---|---|---|---|---|---|---|
| 4-10 | 3,5-ditBu-2-HOPh | H | H | H | H | 0 | S |
| 4-11 | 4-CarPh | iPr | H | H | Cam | 0 | S |
| 4-12 | 4-(BozNH)Ph | Hx | H | H | H | 1 | O |
| 4-13 | 4-PhPh | H | H | Etc | Cam | 0 | S |
| 4-14 | 1-Np | H | H | Car | Cam | 0 | O |
| 4-15 | Bz | H | H | Etc | Cam | 0 | S |
| 4-16 | —CPh₃ | H | H | H | H | 0 | S |
| 4-17 | —CPh₃ | H | H | H | H | 0 | O |
| 4-18 | —CPh₃ | H | H | H | Cam | 0 | S |
| 4-19 | —CPh₃ | H | H | H | Cam | 0 | O |
| 4-20 | —CPh₃ | H | H | H | H | 1 | S |
| 4-21 | —CPh₃ | H | H | H | H | 1 | O |
| 4-22 | —CPh₃ | H | H | H | Cam | 1 | S |
| 4-23 | —CPh₃ | H | H | H | Cam | 1 | O |
| 4-24 | —CPh₃ | H | H | —COOH | Cam | 1 | S |
| 4-25 | —CPh₃ | H | H | —COOH | Cam | 1 | O |
| 4-26 | —CPh₃ | H | H | Etc | Cam | 1 | S |
| 4-27 | —CPh₃ | H | H | Etc | Cam | 1 | O |
| 4-28 | Bz | Me | H | Etc | Cam | 0 | S |
| 4-29 | Bz | Ph | H | H | Cam | 1 | S |
| 4-30 | —CPh₃ | H | H | H | (tBuc)Me | 0 | O |
| 4-31 | Ph | H | H | H | Cam | 0 | S |
| 4-32 | Ph | H | H | H | (Etc)Me | 0 | S |
| 4-33 | Ph | H | H | H | (1-iPrcOEtc)Me | 0 | S |
| 4-34 | Ph | H | H | H | Cam | 1 | S |
| 4-35 | Ph | H | H | H | (NaOOC)Me | 0 | S |
| 4-36 | Ph | H | H | Etc | Cam | 0 | S |
| 4-37 | 4-FPh | H | H | H | Cam | 0 | S |
| 4-38 | 4-FPh | H | H | H | (NaOOC)Me | 0 | S |
| 4-39 | 4-FPh | H | H | H | (Etc)Me | 0 | S |
| 4-40 | 4-FPh | Et | H | H | Cam | 0 | S |
| 4-41 | 3-FPh | H | H | H | Cam | 0 | S |
| 4-42 | 2-FPh | H | H | H | Cam | 0 | S |
| 4-43 | Ph | Me | H | H | Cam | 0 | S |
| 4-44 | 2,4-diFPh | H | H | H | Cam | 0 | S |
| 4-45 | 2,4-diFPh | H | H | H | (1-iPrcOEtc)Me | 0 | S |
| 4-46 | 2,4,6-triFPh | H | H | H | Cam | 0 | S |
| 4-47 | 2,4,5-triFPh | H | H | H | Cam | 0 | S |
| 4-48 | 2-Cl-4-FPh | H | H | H | Cam | 0 | S |
| 4-49 | 4-F-2-TfmPh | H | H | H | (NaOOC)Me | 0 | S |
| 4-50 | 2-Br-4,6-diFPh | H | H | H | Cam | 1 | S |
| 4-51 | 2-EtO-4-F-6-NO₂Ph | H | H | H | (Etc)Me | 0 | S |
| 4-52 | 4-Cl-2-FPh | H | H | H | (Buc)Me | 0 | S |
| 4-53 | 4-TfmPh | H | H | H | Cam | 0 | S |
| 4-54 | 4-TfmPh | H | H | H | (NaOOC)Me | 0 | S |
| 4-55 | 4-TfmPh | H | H | H | (Etc)Me | 0 | S |
| 4-56 | 4-TfmPh | H | H | H | (1-iPrcOEtc)Me | 0 | S |
| 4-57 | 3-TfmPh | H | H | H | Cam | 0 | S |
| 4-58 | 2-TfmPh | H | H | H | Cam | 0 | S |
| 4-59 | 2-AcNH-5-TfmPh | H | H | H | Cam | 0 | S |
| 4-60 | 2-NO₂-4-TfmPh | H | H | H | Cam | 0 | S |
| 4-61 | 1-Np | H | H | H | Cam | 0 | S |
| 4-62 | 2-Np | H | H | H | Cam | 0 | S |
| 4-63 | 4-F-1-Np | H | H | H | Cam | 0 | S |
| 4-64 | 4-ClPh | H | H | H | Cam | 0 | S |
| 4-65 | 3-ClPh | H | H | H | Cam | 0 | S |
| 4-66 | 2-ClPh | H | H | H | Cam | 0 | S |
| 4-67 | 4-BrPh | H | H | H | Cam | 0 | S |
| 4-68 | 3-NO₂Ph | H | H | H | Cam | 0 | S |
| 4-69 | p-Tol | H | H | H | Cam | 0 | S |
| 4-70 | m-Tol | H | H | H | Cam | 0 | S |
| 4-71 | o-Tol | H | H | H | Cam | 0 | S |
| 4-72 | 4-iPrPh | H | H | H | Cam | 0 | S |
| 4-73 | 4-MeOPh | H | H | H | Cam | 0 | S |
| 4-74 | 3-MeOPh | H | H | H | Cam | 0 | S |
| 4-75 | 2-MeOPh | H | H | H | Cam | 0 | S |
| 4-76 | 3-EtNHPh | H | H | H | Cam | 0 | S |
| 4-77 | 4-PhNHPh | H | H | H | Cam | 0 | S |
| 4-78 | 4-PhPh | H | H | H | Cam | 0 | S |
| 4-79 | 4-PhOPh | H | H | H | Cam | 0 | S |
| 4-80 | 4-(NMe₂)Ph | H | H | H | Cam | 0 | S |
| 4-81 | 4-CNPh | H | H | H | Cam | 0 | S |
| 4-82 | 4-EtcPh | H | H | H | Cam | 0 | S |
| 4-83 | 2-HOOCPh | H | H | H | Cam | 0 | S |
| 4-84 | 4-HOPh | H | H | H | Cam | 0 | S |
| 4-85 | 3-HOPh | H | H | H | Cam | 0 | S |
| 4-86 | 2-HOPh | H | H | H | Cam | 0 | S |
| 4-87 | 3,5-ditBu-4-HOPh | H | H | H | Cam | 0 | S |
| 4-88 | 4-HO-3,5-diMEPh | H | H | H | Cam | 0 | S |

TABLE 4-continued

| Cpd. No. | R¹ | R² | R³ | R⁴ | R⁵ | $n$ | X |
|---|---|---|---|---|---|---|---|
| 4-89 | 4-(EtCar)Ph | H | H | H | Cam | 0 | S |
| 4-90 | 2-SamPh | H | H | H | Cam | 0 | S |
| 4-91 | 3-AcPh | H | H | H | Cam | 0 | S |
| 4-92 | 4-BozPh | H | H | H | Cam | 0 | S |
| 4-93 | 4-AcOPh | H | H | H | Cam | 0 | S |
| 4-94 | 4-BozOPh | H | H | H | Cam | 0 | S |
| 4-95 | 3,4,5-triMeOPh | H | H | H | Cam | 0 | S |
| 4-96 | Bzhy | H | H | H | Cam | 0 | S |
| 4-97 | Bzhy | H | H | H | (Etc)Me | 0 | S |
| 4-98 | Bzhy | H | H | H | (NaOOC)Me | 0 | S |
| 4-99 | 4,4'-diFBzhy | H | H | Etc | Cam | 0 | S |
| 4-100 | 4,4'-diFBzhy | H | H | H | Cam | 0 | S |
| 4-101 | di(2-Np)Me | H | H | H | Cam | 0 | S |
| 4-102 | (4-FPh)(2-Np)Me | H | H | H | Cam | 0 | S |
| 4-103 | Bz | H | H | H | Cam | 0 | S |
| 4-104 | Ph | Ph | H | H | Cam | 0 | S |
| 4-105 | Ph | Me | H | H | Cam | 0 | S |
| 4-106 | Phc | H | H | Etc | Cam | 0 | S |
| 4-107 | 1-Npc | H | H | Car | Cam | 0 | S |
| 4-108 | Phc | Me | H | iPrc | Cam | 0 | S |
| 4-109 | Mec | Ph | H | Etc | Cam | 0 | S |
| 4-110 | Etc | Ph | H | MeCar | Cam | 0 | S |
| 4-111 | iPrc | H | H | —COOH | (Mec)Me | 0 | S |
| 4-112 | Bzc | H | H | H | H | 0 | S |
| 4-113 | Bzc | Me | H | Etc | Cam | 0 | S |
| 4-114 | Bzc | Et | H | Etc | Cam | 0 | S |
| 4-115 | Bzc | Ph | H | Buc | (1-PivOEtc)Me | 0 | S |
| 4-116 | 1-Me-1-PhEtc | H | H | Etc | Cam | 0 | S |
| 4-117 | BzhyOCO- | H | H | Etc | Cam | 0 | S |
| 4-118 | Bzs | H | H | Etc | Cam | 0 | S |
| 4-119 | Bzs | H | H | Etc | H | 0 | S |
| 4-120 | Bzs | H | H | H | Cam | 0 | O |
| 4-121 | Mes | H | H | Etc | Cam | 0 | O |
| 4-122 | Mes | iBu | H | Etc | H | 0 | O |
| 4-123 | Tos | Hx | H | Car | Cam | 0 | O |
| 4-124 | Me | H | H | H | Cam | 0 | S |
| 4-125 | Et | H | H | H | Cam | 0 | S |
| 4-126 | iPr | H | H | H | Cam | 0 | S |
| 4-127 | Bu | H | H | H | Cam | 0 | S |
| 4-128 | tBu | H | H | H | Cam | 0 | S |
| 4-129 | Me | Me | H | Etc | Cam | 0 | S |
| 4-130 | Et | Me | H | H | Cam | 0 | S |
| 4-131 | cPn | Et | H | H | Cam | 0 | S |
| 4-132 | cHx | H | H | H | Cam | 0 | S |
| 4-133 | All | H | H | H | Cam | 0 | S |
| 4-134 | All | iBu | H | H | Cam | 0 | S |
| 4-135 | Oc | H | H | H | Cam | 0 | S |
| 4-136 | Et | Et | H | H | Cam | 0 | S |
| 4-137 | Prg | H | H | H | Cam | 0 | S |
| 4-138 | Prg | Me | H | H | Cam | 0 | S |
| 4-139 | α,α-diMePrg | H | H | H | Cam | 0 | S |
| 4-140 | Pr | H | H | H | Cam | 0 | S |
| 4-141 | cPr | H | H | H | Cam | 0 | S |
| 4-142 | cPr | H | H | Etc | Cam | 0 | S |
| 4-143 | cBu | H | H | H | Cam | 0 | S |
| 4-144 | cBu | H | H | Etc | Cam | 0 | S |
| 4-145 | cPn | H | H | H | Cam | 0 | S |
| 4-146 | cPn | H | H | Etc | Cam | 0 | S |

TABLE 5

| Cpd. No. | R¹-R² | R³ | R⁴ | R⁵ | $n$ | X |
|---|---|---|---|---|---|---|
| 5-1 | —(CH₂)₄— | H | H | Cam | 0 | S |
| 5-2 | —(CH₂)₅— | H | Mec | Cam | 0 | S |
| 5-3 | —CO(CH₂)₂CO— | H | Etc | H | 0 | S |
| 5-4 | —COCH = CHCO— | H | Etc | Cam | 0 | S |
| 5-5 | —COCCl = CClCO— | H | Etc | Cam | 0 | S |
| 5-6 | —COCCl = CClCO— | H | H | Cam | 0 | O |
| 5-7 | —CO(1,2-Phy)CO— | H | H | Cam | 0 | S |
| 5-8 | —CO(1,2-Phy)CO— | H | Etc | Cam | 0 | S |
| 5-9 | —(CH₂)₂-O-(CH₂)₂— | H | H | H | 0 | O |
| 5-10 | —(CH₂)₂-O-(CH₂)₂— | H | H | Cam | 0 | S |
| 5-11 | —(CH₂)₂-O-(CH₂)₂— | H | Etc | Cam | 0 | S |
| 5-12 | —(CH₂)₆— | H | H | Cam | 0 | S |
| 5-13 | —(CH₂)₂-NH-(CH₂)₂— | H | H | Cam | 0 | S |
| 5-14 | —(CH₂)₂-NME-(CH₂)₂— | H | H | Cam | 0 | S |
| 5-15 | —(CH₂)₂-NiBu-(CH₂)₂— | H | H | Cam | 0 | S |
| 5-16 | —(CH₂)₂-NPh-(CH₂)₂— | H | H | Cam | 0 | S |
| 5-17 | —(CH₂)₂-NBz-(CH₂)₂— | H | H | Cam | 0 | S |
| 5-18 | —(CH₂)₂-NAc-(CH₂)₂— | H | H | Cam | 0 | S |
| 5-19 | —(CH₂)₅— | H | H | Cam | 0 | S |
| 5-20 | —(CH₂)₂-S-(CH₂)₂— | H | H | Cam | 0 | S |
| 5-21 | —(CH₂)₂-NBoz-(CH₂)₂— | H | H | Cam | 0 | S |
| 5-22 | —CH₂-S-(CH₂)₂— | H | H | Cam | 0 | S |

Of the compounds listed above, the following are preferred, that is to say Compounds No. 2-12, 2-29, 2-30, 2-35, 2-39, 2-41, 2-42, 2-47, 2-59, 2-72, 2-74, 2-75, 2-76, 2-80, 2-82, 2-83, 2-85, 2-86, 2-87, 2-88, 2-89, 2-90, 2-92, 2-93, 2-94, 2-96, 2-97, 2-98, 2-99, 2-105, 3-1, 3-10, 3-17, 3-21, 3-30, 4-18, 4-19, 4-31, 4-34, 4-37, 4-57, 4-73, 4-99, 4-104, 4-125, 4-126, 4-129, 4-132, 4-133, 4-136, 4-141 and 5-10, of which the following are more preferred, that is to say Compounds No. 2-29, 2-41, 2-47, 2-72, 2-76, 2-80, 2-83, 2-88, 2-90, 2-92, 2-105, 3-1, 3-10, 3-17, 3-21, 3-30, 4-18, 4-31, 4-37, 4-57, 4-73, 4-99, 4-104, 4-125, 4-126, 4-132, 4-133, 4-136, 4-141 and 5-10; and the following are most preferred, that is to say;

2-29. 5-{1-ethoxycarbonyl-1-[2-(3-phenylureido)-thiazol-4-yl]methylene}rhodanine-3-acetic acid;

2-41. 5-[2-(3-phenylureido)thiazol-4-ylmethylene]rhodanine-3-acetic acid;

2-47. 5-{1-ethoxycarbonyl-1-[2-[3-(1-naphthyl)ureido]-thiazol-4-yl]methylene}rhodanine-3-acetic acid;

2-72. 5-{1-[2-(3-p-chlorophenylureido)thiazol-4-yl]-1-ethoxycarbonylmethylene}rhodanine-3-acetic acid;

2-76. 5-{1-[2-(3-p-fluorophenylureido)thiazol-4-yl]-1-ethoxycarbonylmethylene}rhodanine-3-acetic acid;

2-88. 5-{1-ethoxycarbonyl-1-[2-[3-(4-fluoro-3-nitrophenyl)ureido]thiazol-4-yl]methylene}rhodanine-3-acetic acid;

2-92. 5-{1-ethoxycarbonyl-1-[2-[3-(2,4,6-trifluorophenyl)ureido]thiazol-4-yl]methylene}rhodanine-3-acetic acid;

3-1. 5-{1-ethoxycarbonyl-1-[2-(3-phenylthioureido)-thiazol-4-yl]methylene}rhodanine-3-acetic acid;

3-10. 5-{1-[2-(3-p-chlorophenylthioureido)thiazol-4yl]-1-ethoxycarbonylmethylene}rhodanine-3-acetic acid;

4-125. 5-(2-ethylaminothiazol-4-ylmethylene)rhodanine-3-acetic acid;

4-126. 5-(2-isopropylaminothiazol-4-ylmethylene)rhodanine-3-acetic acid;

4-133. 5-(2-allylaminothiazol-4-ylmethylene)rhodanine-3-acetic acid;

4-141. 5-(2-cyclopropylaminothiazol-4-ylmethylene)rhodanine-3-acetic acid;

and pharmaceutically acceptable salts and esters thereof.

The compounds of the present invention can be prepared by a variety of methods well known for the preparation of compounds of this type. For example, they may be prepared by reacting a compound of formula (III):

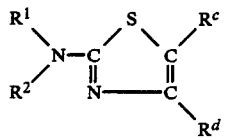

in which $R^1$ and $R^2$ are as defined above, and one of $R^c$ and $R^d$ represents a hydrogen atom, a $C_1$-$C_6$ alkyl group or a halogen atom, and the other of $R^c$ and $R^d$ represents a group of formula (IV):

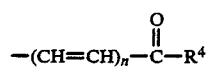

(in which $R^4$ and n are as defined above) with a compound of formula (V):

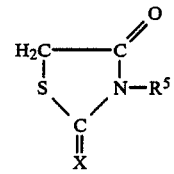

(in which $R^5$ and X are as defined above), and then, if required, converting any group represented by $R^1$, $R^2$, $R^4$ or $R^5$ to any other such group.

There is no particular restriction on the nature of the solvent, provided that it has no adverse effect on the reaction or on the reagents. Examples of suitable solvents include: organic carboxylic acids, such as acetic acid or trifluoroacetic acid; alcohols, such as methanol or ethanol; ethers, such as diethyl ether or tetrahydrofuran; or a mixture of any two or more thereof, or a mixture of any one or more thereof with water.

The reaction will take place over a wide range of temperatures, and the precise reaction temperature chosen is not critical to the invention. In general, we find it convenient to carry out the reaction either at room temperature, for a period of around from 1 to 5 days, or with heating (below about 100° C.) for from 5 minutes to 20 hours.

In order to accelerate the reaction, we prefer to carry it out in the presence of ammonia or an organic base, for example an amine such as methylamine, ethylamine, diethylamine, propylamine, diisopropylamine, piperidine, pyrrolidine or morpholine, and/or a salt, such as sodium acetate, ammonium acetate or ammonium chloride.

If required, a compound of formula (I) in which $R^5$ represents a hydrogen atom may be converted to a corresponding compound in which $R^5$ represents a protected carboxyalkyl group by reacting it with a compound of formula (VI):

(wherein Z represents a halogen atom, such as a chlorine atom or a bromine atom, D represents a straight or branched chain alkylene group having from 1 to 6, preferably from 1 to 3, carbon atoms, and more preferably one carbon atom; and E represents a carboxy-protecting group, e.g. as exemplified in relation to $R^4$).

The reaction is usually effected in a solvent (for example a ketone such as acetone or an amide such as dimethylformamide), in the presence or absence of a base (for example a carbonate such as sodium hydrogen carbonate or potassium carbonate), at a temperature from 0° to 50 ° C., for a period of from 0.5 to 10 hours.

Of the compounds of formula (I), those wherein $R^1$ or $R^2$ represents a hydrogen atom can be converted to other corresponding compounds by alkylation, carbamoylation, acylation, thiocarbamoylation, sulfonylation and sulphenylation, as desired, by reaction with the corresponding halide, such as an alkyl halide, or the corresponding isocyanate or isothiocyanate, such as an arylisocyanate or arylisothiocyanate. The reaction with halides is usually effected in a solvent (for example an ether such as tetrahydrofuran or an amide such as dimethylformamide), in the presence or absence of a base (for example an organic amine such as triethylamine or pyridine), at a temperature from 0° to 50 ° C., for a period of from 10 minutes to 1 day. The reaction with isocyanates is usually effected in a solvent, for example an amide such as dimethylformamide or hexamethyl phosphoric triamide, at a temperature from room temperature to 100° C., for a period of from 1 hour to 20 hours.

Where the compound of the present invention thus prepared contains a carboxy group or an alkoxycarbonyl group in the group represented by $R^4$ and/or $R^5$, the compound can be converted to a corresponding ester compound by an esterification reaction or an ester exchange reaction, or they may be converted to a corresponding amide compound by an amidation reaction, all of which are well known in the art and may be carried out by well known techniques. Furthermore, such esters and amides can be converted to the corresponding carboxylic acid by hydrolysis, which, again, may be carried out by well known means.

The esterification is usually carried out by reaction with a halide or alcohol corresponding to the desired ester group. The reaction with halides is usually effected in a solvent (for example an amide such as dimethylformamide or hexamethyl phosphoric triamide), in the presence of a base (for example an organic amine such as triethylamine or pyridine, or an alkali such as sodium hydroxide), at a temperature of from 0° to 100° C., for a period of from 5 hours to 3 days. The reaction with alcohols is usually effected in a solvent (for example an ether such as tetrahydrofuran or dioxane, or an excess of the alcohol itself which is used in the reaction), in the presence of an acid (for example a mineral acid such as hydrochloric acid or a sulfonic acid such as p-toluenesulfonic acid), at a temperature of from 0° to 50° C. for a period of from 5 hours to 3 days.

At the end of any of the above-mentioned steps in the sequence of reactions for preparing the compounds of the invention, the desired compound may be isolated or purified by known separation or purification methods, such as concentration, concentration under reduced pressure, extraction with solvents, crystallization and recrystallization, solvent substitution, or the various chromatography techniques, notably preparative thin layer chromatography or column chromatography.

The thiazole compound of formula (III) which contains a carbonyl group, which is used as a starting material in the process of the present invention, can be prepared by the method described in Heterocyclic Compounds, 34 (No. 1 to 3) John Wiley & Sons, New York.

A compound of formula (III) in which one of $R^c$ and $R^d$ represents a group of formula —CHO, that is to say an aldehyde, can be prepared by reducing a corresponding compound in which one of $R^c$ and $R^d$ represents a group of formula —CO—COO-alkyl or —COO-alkyl with a metal hydride, such as sodium borohydride or lithium aluminium hydride, and then oxidizing the resulting 1,2-diol with a metal salt of a metaperhalogenic acid such as sodium metaperiodide, or oxidizing the resulting primary alcohol with an oxidizing agent such as manganese dioxide or sulfur trioxide pyridine complex.

In the compounds of formula (I), when $R^5$ represents a hydrogen atom and/or when the compound of formula (I) contains an acidic group, such as a carboxy or sulfo group, the compound of formula (I) can be converted to a pharmaceutically acceptable non-toxic salt by conventional means. Examples of such salts have been given above; and preferred examples include: alkali metal salts, such as the sodium and potassium salts; alkaline earth metal salts, such as the calcium salt; salts of trivalent metals, such as the aluminum salt; and salts of organic bases, such as the morpholine, piperidine, lysine and arginine salts.

The compounds having basicity may also be converted to acid addition salts by methods well known in the art to form, for example, an inorganic acid salt, such as the hydrochloride, sulfate, nitrate or phosphate; or an organic carboxylic or sulfonic acid salt, such as the acetate, succinate, maleate, fumarate, malate, glutamate, aspartate, p-toluenesulfonate or methanesulfonate.

The compounds of the invention are inhibitors of the enzyme aldose reductase, which is implicated in many of the complications of diabetes, and are therefore of value as medicaments in the treatment and prevention of such complications. For instance, this inhibitory activity is exhibited in vitro by the compounds of the invention in tests using an isolated rat or bovine ocular lens, or human erythrocytes or placental tissue. They also show notable activity in vivo, in lowering the sorbitol content in the nervous tissues of a model diabetic animal. They seem to have low toxicity and, in particular, produce very low hepatomegaly in test animals such as mice or rats.

The enzyme-inhibiting activity and low toxicity of the compounds of the invention are demonstrated in the following experiments.

Inhibition of Aldose Reductase

Human placental aldose reductase was separated and partially purified by the method of Kador et al. [Anal. Biochem., 114, 53–58 (1981)]; and its activity was determined photometrically by the method of Varma et al. [Biochem. Pharmac., 25, 2505 (1976)]. Inhibition of enzyme activity was measured for the seven compounds of the invention and the control compound shown in Table 6, using each test compound at a concentration of $1 \times 10^{-5}$M.

The results obtained are shown in Table 6, in which the seven compounds of the invention are identified by the numbers used in Tables 1–5 above, and also by the numbers of the corresponding Examples below which illustrate the preparation of these compounds. The control compound, Compound A, is 5-(thiophen-2-ylmethylene)rhodanine-3-acetic acid, which is disclosed in European Patent Publication No. 47,109.

TABLE 6

| Compound Number | Example Number | Percentage Inhibition |
|---|---|---|
| 2-29 | 1 | 83.1% |
| 2-72 | 14 | 85.2% |
| 2-76 | 13 | 87.1% |
| 2-88 | 44 | 100.0% |
| 2-92 | 45 | 85.6% |
| 3-1 | 6 | 90.4% |
| 3-10 | 7 | 93.9% |
| Compound A | | 34.4% |

Toxicity

The test animals were male mice of the ddy strain, used in six groups, each group consisting of three animals. A single test compound was administered orally to the animals in each group, at a dose of 300 mg/kg body weight. The compounds employed were those identified in Tables 1–5 above as Compounds Nos. 2-29, 2-72, 2-76, 2-92, 3-1 and 3-10. The animals were then observed for one week after administration, during which time they showed no abnormalities which could be attributed to the test compounds. All the animals were alive at the end of the one week observation period.

In view of the substantial dose administered to each animal, the zero mortality indicates that the compounds of the invention have a very low toxicity.

Accordingly, the compounds of the invention may be expected to be effective in the treatment of complications of human diabetes, such as diabetic cataract, diabetic neuropathy and diabetic nephropathy. Their mode of administration will depend on individual circumstances, such as the type of condition under treatment. For example, they may be administered orally, in pharmaceutical formulations such as tablets, capsules, powders, granules and the like, or parenterally in pharmaceutical formulations such as injections (intravenous, subcutaneous or intramuscular), suppositories and the like. For administration to the ocular mucosa, an ophthalmic solution or ophthalmic ointment may preferably be used. These pharmaceutical preparations can be prepared by conventional means and may contain known excipients and adjuvants of a type commonly used in this field, for example vehicles, binders, disintegrators, lubricants, correctives, etc., depending upon the intended use and form of the preparation. The dose of active compound will depend upon the condition, age, and body weight of the patient, as well as upon the nature and severity of the disorder to be treated; but for therapy of diabetic complications the adult daily dose, though depending on the method of administration, may be expected to be in the range of from 0.01 mg to 2 g administered orally or parenterally, and preferably from 100 mg to 1 g for oral administration.

The invention is further described with reference to the following non-limiting Examples and preparations, which show, respectively, the synthesis of compounds in accordance with the present invention and of starting materials useful in preparing such compounds.

EXAMPLE 1

5-{1-Ethoxycarbonyl-1-[2-(3-phenylureido)thiazol-4-yl]methylene}rhodanine-3-acetic acid A mixture comprising 1 g of ethyl 2-(3-phenylureido)thiazol-4-ylglyoxylate, 0.59 g of rhodanine-3-acetic acid 0.4 g of ammonium chloride, 0.4 ml of 28% v/v aqueous ammonia and 4 ml of ethanol was stirred at an external temperature of 80° C. for one hour. The reaction mixture was then acidified with dilute hydrochloric acid and extracted with ethyl acetate. The extract was dried over anhydrous magnesium sulfate, and the solvent was evaporated off under reduced pressure. The residue thus obtained was purified by silica gel column chromatography, using as eluent a 50:1:1:1 by volume mixture of benzene, ethyl acetate, ethanol and acetic acid. The product thus obtained was recrystallized from acetic acid, giving 0.74 g of the desired compound as a yellow powder.

Melting point: 246° to 250 ° C.

Nuclear Magnetic Resonance Spectrum (hexadeuterated dimethyl sulfoxide) $\delta$ ppm: 1.34 (3H, triplet, J=7 Hz), 4.42 (2H, quartet, J=7 Hz), 4.70 (2H, broad singlet), 7.07 (1H, broad triplet, J=7 Hz), 7.35 (2H, broad triplet, J=7 Hz), 7.49 (2H, broad doublet, J=7 Hz), 7.70 (1H, singlet), 8.96 (1H, broad singlet), 11.02 (1H, broad singlet).

EXAMPLE 2

5-{1-Ethoxycarbonyl-1-[2-[3-(1-naphthyl)ureido]-thiazol-4-yl]methylene}rhodanine-3-acetic acid Following a procedure similar to that described in Example 1, 0.45 g of the desired compound was prepared from 3.7 g of ethyl 2-[3-(1-naphthyl)ureido]-thiazol-4-ylglyoxylate, 1.53 g of 3-rhodanineacetic acid, 1 g of ammonium chloride. 1 ml of a 28% v/v aqueous ammonia and 20 ml of ethanol. The product was a yellow powder having the following physical properties.

Melting Point: 263° to 265° C.

Nuclear Magnetic Resonance Spectrum (hexadeuterated dimethyl sulfoxide) $\delta$ ppm: 1.34 (3H, triplet, J=7 Hz), 4.43 (2H, quartet, J=7 Hz), 4.70 (2H, singlet), 7.49–7.76 (4H, multiplet), 7.72 (1H, singlet), 7.95–8.13 (3H, multiplet), 9.15 (1H, broad singlet), 11.36 (1H, broad singlet).

EXAMPLE 3

5-[1-(2-Acetylaminothiazol-4-yl)-1-ethoxycarbonylmethylene]rhodanine-3-acetic acid 1/3 hydrate A mixture comprising 4.35 g of ethyl 2-aminothiazol-4-ylglyoxylate, 5 g of rhodanine-3-acetic acid, 2.7 g of sodium acetate and 50 ml of acetic acid was heated under reflux for 2 days. The reaction mixture was then worked up as in Example 1, to give the desired compound as a yellow powder.

Melting point: 292° to 296° C.

Nuclear Magnetic Resonance Spectrum (hexadeuterated dimethyl sulfoxide) $\delta$ ppm: 1.33 (3H, triplet, J=7 Hz), 2.22 (3H, singlet), 4.42 (2H, quartet, J=7 Hz), 4.68 (2H, singlet), 7.73 (1H, singlet), 12.47 (1H, broad singlet).

EXAMPLE 4

5-[1-(2-Aminothiazol-4-yl)-1-ethoxycarbonylmethylene]rhodanine-3-acetic acid monohydrate The desired compound was prepared by reacting at room temperature, for 15 minutes, 20 g of ethyl 2-aminothiazol-4-ylglyoxylate, 22.9 g of rhodanine-3-acetic acid, 11 g of ammonium chloride, 15 ml of 28% v/v aqueous ammonia and 200 ml of ethanol, following a procedure similar to that described in Example 1. The resulting orange product had the following physical properties.

Melting point: 250° to 254° C.

Nuclear Magnetic Resonance Spectrum (hexadeuterated dimethyl sulfoxide) $\delta$ ppm: 1.31 (3H, triplet, J=7 Hz), 4.37 (2H, quartet, J=7 Hz), 4.66 (2H, singlet), 7.20 (1H, singlet), 7.64 (2H, broad singlet).

EXAMPLE 5

5-{1-Ethoxycarbonyl-1-[2-(3-p-toluenesulfonylureido)-thiazol-4-yl]methylene}rhodanine-3-acetic acid monohydrate Following a procedure similar to that described in Example 1, the desired compound was prepared from 4 g of ethyl 2-(3-p-toluenesulfonylureido)thiazol-4-ylglyoxylate, 2 g of rhodanine-3-acetic acid, 1 g of ammonium chloride, 1 ml of 28% v/v aqueous ammonia and 10 ml of ethanol. The resulting product was a yellow powder having the following physical properties.

Melting point: 207° to 209° C.

Nuclear Magnetic Resonance Spectrum (hexadeuterated dimethyl sulfoxide) $\delta$ ppm: 1.31 (3H, triplet, J=7 Hz), 2.40 (3H, singlet). 4.40 (2H, quartet, J=7 Hz), 4.68 (2H, singlet), 7.43 (2H, doublet. J=8 Hz), 7.70 (1H, singlet), 7.87 (2H, doublet, J=8 Hz), 11.32 (1H, broad singlet).

EXAMPLE 6

5-{1-Ethoxycarbonyl-1-[2-(3-phenylthioureido)thiazol-4-yl]methylenerhodanine-3-acetic acid Following a procedure similar to that described in Example 1, 0.60 g of the desired compound was prepared from 3.35 g of ethyl 2-(3-phenylthioureido)-thiazol-4-ylglyoxylate. 1.7 g of rhodanine-3-acetic acid, 1 g of ammonium chloride. 1 ml of 28% v/v aqueous ammonia and 30 ml of ethanol. The resulting product was a yellow powder having the following physical properties.

Melting point: 240° to 248° C.
Nuclear Magnetic Resonance Spectrum (hexadeuterated dimethyl sulfoxide) δ ppm: 1.34 (3H, triplet, J=7 Hz), 4.42 (2H, quartet, J=7 Hz), 4.70 (2H, singlet), 7.22 (1H, broad triplet, J=8 Hz), 7.41 (2H, broad triplet, J=8 Hz), 7.63 (2H, broad doublet, J=8 Hz), 7.65 (2H, singlet), 10.33 (1H, broad singlet), 11.8–12.2 (1H, broad singlet), 12.9–13.6 (1H, broad singlet).

EXAMPLE 7

5-{1-[2-(3-p-Chlorophenylthioureido)thiazol-4-yl]-1-ethoxycarbonylmethylene}rhodanine-3-acetic acid Following a procedure similar to that described in Example 1, 0.39 g of the desired compound was prepared from 0.93 g of ethyl 2-(3-p-chlorophenylthioureido)thiazol-4-ylglyoxylate, 0.48 g of rhodanine-3-acetic acid, 0.25 g of ammonium chloride, 0.25 ml of 28s% v/v aqueous ammonia and 5 ml of ethanol. The resulting product was a yellow powder having the following physical properties.

Melting point: 225° to 235° C.
Nuclear Magnetic Resonance Spectrum (hexadeuterated dimethyl sulfoxide) δ ppm: 1.34 (3H, triplet, J=7 Hz), 4.42 (2H, quartet, J=7 Hz), 4.70 (2H, singlet), 7.47 (2H, broad doublet), 7.65 (2H, broad doublet), 7.67 (1H, singlet), 10.38 (1H, broad singlet), 12.06 (1H, broad singlet), 13.0–13.7 (1H, broad singlet).

EXAMPLE 8

5-[1-(2-Benzamidothiazol-4-yl)-1-ethoxycarbonylmethylene]rhodanine-3-acetic acid Following a procedure similar to that described in Example 1, the desired compound was prepared from 3.04 g of ethyl 2-benzamidothiazol-4-ylglyoxylate, 1.91 g of rhodanine-3-acetic acid, 1 g of ammonium chloride, 1 ml of 28% v/v aqueous ammonia and 20 ml of ethanol. The resulting product was a yellow powder having the following physical properties.

Melting point: 278° to 281° C.
Nuclear Magnetic Resonance Spectrum (hexadeuterated dimethyl sulfoxide) δ ppm: 1.35 (3H, triplet, J=7 Hz), 4.44 (2H, quartet, J=7 Hz), 4.70 (2H, singlet), 7.57–7.72 (3H, multiplet), 7.83 (1H, singlet), 8.12 (2H, broad doublet, J=7 Hz), 12.91 (1H, broad singlet), 13.1–13.6 (1H, broad singlet).

EXAMPLE 9

5-{1-Ethoxycarbonyl-1-[2-(3-phenylureido)thiazol-4-yl]methylene}rhodanine acetic acid adduct Following a procedure similar to that described in Example 1, the desired compound was prepared from 3 g of ethyl 2-(3-phenylureido)thiazol-4-ylglyoxylate, 1.25 g of rhodanine, 1 g of ammonium chloride 1 ml of 28% v/v aqueous ammonia and 10 ml of ethanol. The resulting product was a yellow powder having the following physical properties.

Melting point: circa 257° C. (with decomposition).
Nuclear Magnetic Resonance Spectrum (hexadeuterated dimethyl sulfoxide) δ ppm: 1.32 (3H, triplet, J=7 Hz), 1.91 (3H, singlet), 4.39 (2H, quartet, J=7 Hz), 7.07 (1H, broad triplet, J=7 Hz), 7.34 (2H, broad triplet, J=7 Hz), 7.48 (2H, broad doublet, J=7 Hz), 7.58 (1H, singlet), 8.93 (1H, broad singlet), 10.94 (1H. broad singlet), 11.7–12.2 (1H, broad singlet), 13.73 (1H, broad singlet).

EXAMPLE 10

≡-{1-[2-(3-o-Methoxyphenylureido)thiazol-4-yl]-1-ethoxycarbonylmethylene}rhodanine-3-acetic acid monohydrate Following a procedure similar to that described in Example 1, the desired compound was prepared from 1.75 g of ethyl 2-(3-o-methoxyphenylureido)thiazol-4-ylglyoxylate, 0.95 g of rhodanine-3-acetic acid, 0.5 g of ammonium chloride, 0.5 ml of 28% v/v aqueous ammonia and 25 ml of ethanol. The resulting product was a yellow powder having the following physical properties.

Melting point: circa 230° C. (with decomposition).
Nuclear Magnetic Resonance Spectrum (hexadeuterated dimethyl sulfoxide) δ ppm: 1.34 (3H, triplet, J=7 Hz), 3.91 (3H, singlet), 4.42 (2H, quartet, J=7 Hz), 4.69 (2H, singlet), 6.9–7.0 (1H, multiplet), 7.0–7.1 (2H, multiplet), 7.69 (1H, singlet), 8.1–8.15 (1H, multiplet), 8.76 (1H, broad singlet, disappeared on adding deuterium oxide), 11.54 (1H, broad singlet, disappeared on adding deuterium oxide).

EXAMPLE 11

5-{1-[2-(3-m-Methoxyphenylureido)thiazol-4-yl]-1-ethoxycarbonylmethylene}rhodanine-3-acetic acid monohydrate Following a procedure similar to that described in Example 1, the desired compound was prepared from 1.75 g of ethyl 2-(3-m-methoxyphenylureido)thiazol-4-ylglyoxylate, 0.95 g of rhodanine-3-acetic acid, 0.5 g of ammonium chloride, 0.5 ml of 28% v/v aqueous ammonia and 20 ml of ethanol. The resulting product was a yellow powder having the following physical properties.

Melting point: 208° to 212° C. (with decomposition).
Nuclear Magnetic Resonance Spectrum (hexadeuterated dimethyl sulfoxide) δ ppm: 1.34 (3H, triplet, J=7 Hz), 3.76 (3H, singlet), 4.42 (2H, quartet, J=7 Hz), 4.69 (2H, singlet), 6.65 (1H, dd, J=2 and 8 Hz), 6.98 (1H, dd, J=2 and 8 Hz), 7.18 (1H, triplet, J=2 Hz), 7.24 (1H, triplet. J=8 Hz). 7.70 (1H, singlet), 8.97 (1H, broad singlet, disappeared on adding deuterium oxide), 11.02 (1H, broad singlet, disappeared on adding deuterium oxide), 13.1–13.7 (1H, broad, disappeared on adding deuterium oxide).

EXAMPLE 12

5-{1-[2-(3-p-Methoxyphenylureido)thiazol-4-yl]-1-ethoxycarbonylmethylene}rhodanine-3-acetic acid Following a procedure similar to that described in Example 1, the desired compound was prepared from 1.75 g of ethyl 2-(3-p-methoxyphenylureido)thiazol-4-ylglyoxylate, 0.95 g of rhodanine-3-acetic acid, 0.5 g of ammonium chloride, 0.5 ml of 28% v/v aqueous ammonia and 20 ml of ethanol. The resulting product was a yellow powder having the following physical properties.

Melting point: 230° to 235° C. (with decomposition).
Nuclear Magnetic Resonance Spectrum (hexadeuterated dimethyl sulfoxide) δ ppm: 1.33 (3H, triplet, J=7 Hz), 3.74 (3H, singlet), 4.41 (2H, quartet, J=7 Hz), 4.69 (2H, singlet), 6.91 (2H, doublet, J=9 Hz), 7.39 (2H, doublet, J=9 Hz), 7.67 (1H, singlet), 8.79 (1H, broad singlet), 10.99 (1H, broad singlet), 13.1–13.7 (1H, broad).

EXAMPLE 13

5-{1-[2-(3-p-Fluorophenylureido)thiazol-4-yl]-1-ethoxycarbonylmethylene}rhodanine-3-acetic acid Following a procedure similar to that described in Example 1, 1.91 g of the desired compound was prepared from 3.4 g of ethyl 2-(3-p-fluorophenylureido)-thiazol-4-ylglyoxylate, 1.9 g of rhodanine-3-acetic acid, 1 g of ammonium chloride, 1 ml of 28% v/v aqueous ammonia and 50 ml of ethanol. The resulting product was a yellow powder having the following physical properties.

Melting point: 228° to 253° C. (with decomposition).
Nuclear Magnetic Resonance Spectrum (hexadeuterated dimethyl sulfoxide) δ ppm: 1.34 (3H, triplet, J=7 Hz), 4.42 (2H, quartet, J=7 Hz), 4.70 (2H, singlet), 7.18 (2H, triplet, J=9 Hz), 7.50 (2H, doublet of doublets, J=5 and 9 Hz), 7.70 (1H, singlet), 8.97 (1H, broad singlet, disappeared on adding deuterium oxide), 1.05 (1H, broad singlet, disappeared on adding deuterium oxide), 13.1–13.7 (1H, broad singlet, disappeared on adding deuterium oxide).

EXAMPLE 14

5-{1-2-(3-p-Chlorophenylureido)thiazol-4-yl]-1-ethoxycarbonylmethylene}rhodanine-3-acetic acid Following a procedure similar to that described in Example 1, 0.77 g of the desired compound was prepared from 3.54 g of ethyl 2-(3-p-chlorophenylureido)-thiazol-4-ylglyoxylate, 1.9 g of rhodanine-3-acetic acid, 1 g of ammonium chloride, 1 ml of 28% v/v aqueous ammonia and 30 ml of ethanol. The resulting product was a yellow powder having the following physical properties.

Melting point: 238° to 242° C.
Nuclear Magnetic Resonance Spectrum (hexadeuterated dimethyl sulfoxide) δ ppm: 1.34 (3H, triplet, J=7 Hz), 4.42 (2H, quartet, J=7 Hz), 4.70 (2H, singlet), 7.39 (2H, doublet, J=9 Hz), 7.52 (2H, doublet, J=9 Hz), 7.71 (1H, singlet), 9.08 (1H, broad singlet, disappeared on adding deuterium oxide), 11.08 (1H, broad singlet, disappeared on adding deuterium oxide).

EXAMPLE 15

5-{1-[2-(3-p-Bromophenylureido)thiazol-4-yl]-1-ethoxycarbonylmethylene}rhodanine-3-acetic acid Following a procedure similar to that described in Example 1, the desired compound was prepared from 4 g of ethyl 2-(3-p-bromophenylureido)thiazol-4-ylglyoxylate, 2 g of rhodanine-3-acetic acid, 1 g of ammonium chloride, 1 ml of 28% v/v aqueous ammonia and 50 ml of ethanol. The resulting product was a yellow powder having the following physical properties.

Melting point: 251° to 258° C. (with decomposition).
Nuclear Magnetic Resonance Spectrum (hexadeuterated dimethyl sulfoxide) δ ppm: 1.33 (3H. triplet, J=7 Hz), 4.42 (2H, quartet, J=7 Hz), 4.69 (2H, singlet), 7.47 (2H, doublet, J=9 Hz), 7.52 (2H, doublet, J=9 Hz), 7.70 (1H, singlet), 9.11 (1H, broad singlet, disappeared on adding deuterium oxide), 11.11 (1H, broad singlet, disappeared on adding deuterium oxide), 13.1–13.7 (1H, broad singlet, disappeared on adding deuterium oxide).

EXAMPLE 16

5-{1-[2-[3-(3,4-Dichlorophenyl)ureido]thiazol-4-yl]-1-ethoxycarbonylmethylene}rhodanine-3-acetic acid hemihydrate Following a procedure similar to that described in Example 1, the desired compound was prepared from 3.9 g of ethyl 2-[3-(3,4-dichlorophenyl)ureido]thiazol-4-ylglyoxylate, 1.9 g of rhodanine-3-acetic acid, 1 g of ammonium chloride, 1 ml of 28% v/v aqueous ammonia and 60 ml of ethanol. The resulting product was a yellow powder having the following physical properties.

Melting point: 223° to 224° C.
Nuclear Magnetic Resonance Spectrum (hexadeuterated dimethyl sulfoxide) δ ppm: 1.34 (3H, triplet, J=7 Hz), 4.42 (2H, quartet, J=7 Hz), 4.70 (2H, singlet), 7.40 (1H, doublet of doublets J=2 and 9 Hz), 7.58 (1H, doublet, J=9 Hz), 7.73 (1H, singlet), 7.88 (1H, doublet, J=2 Hz), 9.22 (1H, broad singlet), 11.21 (1H, broad singlet), 13.0–13.8 (1H, broad).

EXAMPLE 17

Piperidinium 5-(2-Tritylaminothiazol-4-ylmethylene)rhodanine-3-acetate

A mixture comprising 2.5 g of 2-tritylaminothiazole-4-carbaldehyde, 0.81 g of rhodanine-3-acetic acid, 1.1 g of piperidine and 25 ml of ethanol was stirred at room temperature for 7 hours. The crystalline product which precipitated out was collected by filtration and washed with methanol, to obtain 2.7 g of the desired compound as a yellowish-brown powder.

Melting point: 210° to 215° C. (with decomposition).
Nuclear Magnetic Resonance Spectrum (hexadeuterated dimethyl sulfoxide) δ ppm: 1.52–1.61 (6H, multiplet), 2.92 (4H, broad triplet, J=5 Hz), 4.24 (2H, singlet), 7.16–7.42 (17H, multiplet), 8.97 (1H, singlet).

EXAMPLE 18

Piperidinium 2,4-Dioxo-5-(2-tritylaminothiazol-4-ylmethylene)-thiazolidine-3-acetate Following a procedure similar to that described in Example 17, the desired compound was prepared from 2.3 g of 2-tritylaminothiazole-4-carbaldehyde, 0.9 g of 2,4-dioxothiazolidine-3-acetic acid, 0.9 g of piperidine and 20 ml of ethanol. The resulting product was a pale yellow powder having the following physical properties.

Melting point: 205° to 210° C. (with decomposition).
Nuclear Magnetic Resonance Spectrum (hexadeuterated dimethyl sulfoxide) δ ppm: 1.53–1.62 (6H, multiplet), 2.94 (4H, broad triplet, J=5 Hz), 3.82 (2H, singlet), 7.16–7.41 (17H, multiplet), 8.91 (1H, singlet).

EXAMPLE 19 t-Butyl 2,4-dioxo-5-(2-tritylaminothiazol-4-ylmethylene)-thiazolidine-3-acetate

Following a procedure similar to that described in Example 17, the desired compound was prepared from 2 g of 2-tritylaminothiazole-4-carbaldehyde, 1.2 g of t-butyl 2,4-dioxothiazolidine-3-acetate, 0.88 g of piperidine and 20 ml of ethanol. The resulting product was a yellow powder having the following physical properties.

Softening point: 103° to 106° C.
Nuclear Magnetic Resonance Spectrum (hexadeuterated dimethyl sulfoxide) δ ppm: 1.40 (9H, singlet), 4.21 (2H, singlet), 7.16–7.4 (17H, multiplet), 8.96 (1H, singlet).
Mass spectrum (m/e): 583 (M+).

EXAMPLE 20

5-(2-Tritylaminothiazol-4-ylmethylene)thiazolidine-2,4-dione

Following a procedure similar to that described in Example 17, the desired compound was prepared from 2 g of 2-tritylaminothiazole-4-carbaldehyde, 0.7 g of 2,4-thiazolidinedione, 1 g of piperidine and 20 ml of ethanol. The resulting product was a pale brown powder having the following physical properties.

Melting point: 225° to 228° C.
Nuclear Magnetic Resonance Spectrum (hexadeuterated dimethyl sulfoxide) δ ppm: 7.15–7.40 (17H, multiplet), 8.88 (1H, singlet), 11.99 (1H, broad singlet).
Mass spectrum (m/e): 469 (M+).

EXAMPLE 21

5-(2-Aminothiazol-4-ylmethylene)rhodanine-3-acetic acid ⅓ hydrate

A mixture comprising 2.2 g of piperidinium 5-(2-tritylaminothiazol-4-ylmethylene)rhodanine-3-acetate and 30 ml of a 4N dioxane solution of hydrogen chloride was stirred at room temperature for 30 minutes, and the resulting mixture was left to stand overnight. The crystalline product which precipitated out was collected by filtration and washed with dioxane, giving the desired compound as a brownish-orange powder.

Melting point: 244° to 246° C. (with decomposition).
Nuclear Magnetic Resonance Spectrum (hexadeuterated dimethyl sulfoxide) δ ppm: 3–4 (2H, broad), 4.70 (2H, singlet), 7.50 (1H, singlet), 7.51 (1H, singlet).

EXAMPLE 22

5-(2-Aminothiazol-4-ylmethylene)thiazolidine-2,4-dione hydrochloride

Following a procedure similar to that described in Example 21, the desired compound was prepared from 1.4 g of 5-(2-tritylaminothiazole-4-ylmethylene)thiazolidine-2,4-dione and 25 ml of a 4N dioxane solution of hydrogen chloride. The resulting product was a pale brown powder having the following physical properties.

Melting point: 280° to 288° C. (with decomposition).
Nuclear Magnetic Resonance Spectrum (hexadeuterated dimethyl sulfoxide) δ ppm: 4.8–6.9 (2H, broad, disappeared on adding deuterium oxide), 7.28 (1H, singlet), 7.41 (1H, singlet), 12.2 (1H, broad singlet, disappeared on adding deuterium oxide).

EXAMPLE 23

5-(2-Aminothiazol-4-ylmethylene)-2,4-dioxothiazolidine-3-acetic acid hydrochloride

Method A

A mixture comprising 2 g of t-butyl 2,4-dioxo-5-(2-tritylaminothiazol-4-ylmethylene)thiazolidine-3-acetate, 30 ml of a 4N dioxane solution of hydrogen chloride and 100 ml of acetic acid was heated at 80° C. for 3 hours. The resulting mixture was cooled to room temperature and the crystalline product which precipitated out was collected by filtration to give the desired compound in the form of a powder.

Method B

Following a procedure similar to that described in Example 21, the desired compound was prepared from 2.7 g of piperidinium 2,4-dioxo-5-(2-tritylaminothiazol-4-ylmethylene)thiazolidine-3-acetate and 30 ml of a 4N dioxane solution of hydrogen chloride. The resulting product was a pale brown powder having the following physical properties.

Melting point: 295° to 298° C. (with decomposition).
Nuclear Magnetic Resonance Spectrum (hexadeuterated dimethyl sulfoxide) δ ppm: 3.7–5.7 (2H, broad), 4.32 (2H, singlet), 7.39 (1H, singlet), 7.60 (1H, singlet).

EXAMPLE 24

5-[2-(3-phenylureido)thiazol-4-ylmethylene]rhodanine-3-acetic acid

A mixture comprising 1 g of 2-(3-phenylureido)-thiazole-4-carbaldehyde, 0.85 g of rhodanine-3-acetic acid, 0.76 g of piperidine and 15 ml of ethanol was stirred at room temperature for 2 hours, and the resulting mixture was left to stand overnight. The crystals which precipitated out were collected by filtration dispersed in dilute aqueous hydrochloric acid, and washed with stirring for 30 minutes. The resulting crystalline product was recrystallized from a mixture of acetic acid and ethyl acetate, giving 0.78 g of the desired compound as an orange powder.

Melting point: 251° to 256° C. (with decomposition).
Nuclear Magnetic Resonance Spectrum (hexadeuterated dimethyl sulfoxide) δ ppm: 4.72 (2H, singlet), 7.07 (1H, triplet, J=8 Hz), 7.34 (2H, triplet, J=8 Hz), 7.48 (2H, doublet, J=8 Hz), 7.73 (1H, singlet), 7.95 (1H, singlet), 8.94 (1H, broad singlet), 10.87 (1H, broad singlet), 13–13.7 (1H, broad).

EXAMPLE 25

2,4-Dioxo-5-[2-(3-phenylureido)thiazol-4-ylmethylene]-thiazolidine-3-acetic acid

Method A

Following a procedure similar to that described in Example 24, the desired compound was prepared from 1 g of 2-(3-phenylureido)thiazole-4-carbaldehyde, 0.78 g of 2,4-dioxothiazolidine-3-acetic acid, 0.76 g of piperidine and 20 ml of ethanol. The resulting product was a yellow powder having the physical properties set out below.

Method B

Following a procedure similar to that described in Preparation 1, the desired compound was prepared from 0.6 g of 5-(2-aminothiazol-4-ylmethylene)-2,4-dioxothiazolidine-3-acetic acid hydrochloride, 0.75 g of phenyl isocyanate and 20 ml of hexamethylphosphoric triamide. The resulting product was a yellow powder having the following physical properties.

Melting point: 230° to 235° C. (with decomposition).

Nuclear Magnetic Resonance Spectrum (hexadeuterated dimethyl sulfoxide) δ ppm: 4.35 (2H, singlet), 7.06 (1H, triplet, J=8 Hz), 7.34 (2H, triplet, J=8 Hz), 7.48 (2H, doublet, J=8 Hz), 7.83 (1H, singlet), 7.87 (1H, singlet), 8.98 (1H, singlet), 10.76 (1H, singlet), 13–13.7 (1H, broad).

EXAMPLE 26

5-[2-(3-phenylureido)thiazol-4-ylmethylene]rhodanine

Following a procedure similar to that described in Example 24, the desired compound was prepared from 1 g of 2-(3-phenylureido)thiazole-4-carbaldehyde, 0.6 g of rhodanine, 0.75 g of piperidine and 15 ml of ethanol. The resulting product was a yellow-brown powder having the following physical properties.

Melting point: over 300° C. (with decomposition).

Nuclear Magnetic Resonance Spectrum (hexadeuterated dimethyl sulfoxide) δ ppm: 7.06 (1H, triplet, J=8 Hz), 7.34 (2H, triplet, J=8 Hz), 7.48 (2H, doublet, J=8 Hz), 7.50 (1H, singlet), 7.85 (1H, singlet), 8.93 (1H, singlet), 10.80 (1H, singlet, disappeared on adding deuterium oxide), 13.55 (1H, broad singlet, disappeared on adding deuterium oxide).

EXAMPLE 27

Benzyl 5-[1-(2-aminothiazol-4-yl)-1-ethoxycarbonylmethylene]rhodanine-3-acetate

A mixture comprising 2 g of 5-[1-(2-aminothiazol-4-yl)-1-ethoxycarbonylmethylene]rhodanine-3-acetic acid monohydrate, 3 g of benzyl bromide, 1.1 g of triethylamine and 10 ml of hexamethylphosphoric triamide was stirred at room temperature for 16 hours. The reaction mixture was acidified with dilute hydrochloric acid and then extracted with ethyl acetate. The extract was dried over anhydrous magnesium sulfate and the solvent was evaporated off under reduced pressure. The residue was purified by silica gel column chromatography using as eluent a 8:2:1 by volume mixture of hexane, ethyl acetate and acetic acid, giving the desired compound as yellow crystals.

Melting point: 177° to 179° C.

Nuclear Magnetic Resonance Spectrum (hexadeuterated dimethyl sulfoxide) δ ppm: 1.30 (3H, triplet, J=7 Hz), 4.37 (2H, quartet, J=7 Hz), 4.84 (2H, singlet), 5.19 (2H, singlet), 7.21 (1H, singlet), 7.36 (5H, singlet), 7.64 (1H, broad singlet, disappeared on adding deuterium oxide).

EXAMPLE 28

5-[1-(2-Acetylaminothiazol-4-yl)-1-ethoxycarbonylmethylene]-2,4-dioxothiazolidine-3-acetic acid A mixture comprising 0.6 g of crude 5-{1-ethoxycarbonyl-1-hydroxy-1-[2-(3-phenylureido)thiazol-4-yl]methyl}-2,4-dioxothiazolidine-3-acetic acid [prepared from 2.6 g of ethyl 2-(3-phenylureido)thiazol-4-ylglyoxylate, 1.2 g of 2,4-dioxothiazolidine-3-acetic acid, 1.2 g of piperidine and 30 ml of ethanol by a procedure similar to that of Example 24], 0.5 g of acetic anhydride and 4 ml of pyridine was heated at 60° C. for 17 hours. The reaction mixture was poured into water and extracted with ethyl acetate. The extract was dried over anhydrous sodium sulfate, and the solvent was evaporated off under reduced pressure. The resulting oil was purified by silica gel column chromatography, using as eluent a 8:2:0.5 to 7:3:0.5 by volume mixture of benzene, ethyl acetate and acetic acid, giving the desired compound as a yellow powder having the following physical properties.

Melting point: 288° to 290° C.

Nuclear Magnetic Resonance Spectrum (hexadeuterated dimethyl sulfoxide) δ ppm: 1.32 (3H, triplet, J=7 Hz), 2.22 (3H, singlet), 4.31 (2H, singlet), 4.39 (2H, quartet, J=7 Hz), 7.63 (1H, singlet), 12.38 (1H, broad singlet, disappeared on adding deuterium oxide).

EXAMPLE 29

5-{1-[2-(3-Benzoylthioureido)thiazol-4-yl]-1-ethoxycarbonylmethylene}rhodanine-3-acetic acid ½ acetic acid ½ ammonia adduct The reaction described in Example 1 was repeated, but using 1.5 g of ethyl 2-(3-benzoylthioureido)thiazol-4-ylglyoxylate, 0.79 g of rhodanine-3-acetic acid, 0.1 g of ammonium chloride, 0.4 ml of 28% v/v aqueous ammonia, and 20 ml of ethanol, giving the title compound as a yellow powder.

Melting point: 233°–235° C.

Nuclear Magnetic Resonance Spectrum (hexadeuterated dimethyl sulfoxide) δ ppm: 1.34 (3H, triplet, J=7 Hz), 1.91 (1.5H, singlet), 4.43 (2H, quartet, J=7 Hz), 4.67 (2H, singlet), 7.53 (2H, triplet. J=7 Hz), 7.65 (1H, triplet, J=7 Hz), 7.69 (1H, singlet). 8.01 (2H, doublet, J=7 Hz).

EXAMPLE 30

Methyl 5-{1-ethoxycarbonyl-1-[2-(3-phenylureido)thiazol-4-yl]methylene}rhodanine-3-acetate A mixture comprising 5 g of 5-{1-ethoxycarbonyl-1-2-(3-phenylureido)thiazol-4-yl]methylene}rhodanine-3-acetic acid, 10 g of methanol and 75 ml of a 4N dioxane solution of hydrogen chloride was left to stand at room temperature for about 20 hours. The reaction mixture was then poured into water and extracted with ethyl acetate. The extract was dried over anhydrous sodium sulfate, and the solvent was evaporated off under reduced pressure. The residue was purified by silica gel column chromatography using as eluent a 3:1 to 1:1 by volume mixture of hexane and ethyl acetate. The resulting yellow crystalline product had the following physical properties.

Melting point: 228° to 233° C.

Nuclear Magnetic Resonance Spectrum (hexadeuterated dimethyl sulfoxide) δ ppm: 1.33 (3H, triplet, J=7 Hz), 3.70 (3H, singlet), 4.42 (2H, quartet, J=7 Hz), 4.81 (2H, singlet), 7.07 (1H, triplet, J=8 Hz), 7.34 (2H, triplet, J=8 Hz), 7.49 (2H, doublet, J=8 Hz), 7.71 (1H, singlet), 8.95 (1H, singlet disappeared on adding deuterium oxide), 11.03 (1H, broad singlet, disappeared on adding deuterium oxide).

EXAMPLE 31

Ethyl 5-{1-ethoxycarbonyl-1-[2-(3-phenylureido)thiazol-4-yl]methylene}rhodanine-3-acetate monohydrate Following a procedure similar to that described in Example 30, the desired compound was prepared from 2 g of 5-{1-ethoxycarbonyl-1-[2-(3-phenylureido)-thiazol-4-yl]methylene}rhodanine-3-acetic acid, 3 g of ethanol and 30 ml of a 4N dioxane solution of hydrogen chloride. The resulting product was a yellow powder having the following physical properties.

Melting point: 94° to 98° C.

Nuclear Magnetic Resonance Spectrum (hexadeuterated dimethyl sulfoxide) δ ppm: 1.18 (3H, triplet J=7 Hz) 1.21 (3H, triplet, J=7 Hz), 4.14 (2H, quartet, J=7 Hz), 4.29 (2H, quartet, J=7 Hz), 4.74 (2H, singlet), 7.05 (1H, triplet, J=7 Hz), 7.28 (1H, singlet), 7.33 (2H, triplet, J=7 Hz), 7.48 (2H, doublet, J=7 Hz), 8.98 (1H, broad singlet, disappeared on adding deuterium oxide), 10.62 (1H, broad singlet, disappeared on adding deuterium oxide).

EXAMPLE 32

Isopropyl 5-{1-ethoxycarbonyl-1-[2-(3-phenylureido)thiazol-4-yl]methylene}rhodanine-3-acetate sesquihydrate Following a procedure similar to that described in Example 27, the desired compound was prepared from 1 g of 5-{1-ethoxycarbonyl-1-[2-(3-phenylureido)-thiazol-4-yl]methylene}rhodanine-3-acetic acid, 0.5 g of isopropyl bromide, 0.25 g of triethylamine and 10 ml of hexamethylphosphoric triamide. The resulting yellow crystalline product had the following physical properties.

Melting point: 113° to 116° C.

Nuclear Magnetic Resonance Spectrum (hexadeuterated dimethyl sulfoxide) δ ppm: 1.21 (6H, doublet, J=6 Hz), 1.33 (3H, triplet, J=7 Hz), 4.42 (2H, quartet, J=7 Hz), 4.75 (2H, singlet), 4.96 (1H, septet, J=6 Hz), 7.07 (1H, triplet, J=8 Hz), 7.34 (2H, triplet, J=8 Hz), 7.49 (2H, doublet, J=8 Hz), 7.71 (1H, singlet), 8.95 (1H, broad singlet, disappeared on adding deuterium oxide), 11.03 (1H, broad singlet, disappeared on adding deuterium oxide).

EXAMPLE 33

Benzyl 5-{1-ethoxycarbonyl-1-[2-(3-phenylureido)thiazol-4-yl]methylene}rhodanine-3-acetate A mixture comprising 1 g of 5-{1-ethoxycarbonyl-1-[2-(3-phenylureido)thiazol-4-yl]methylene}rhodanine-3-acetic acid, 0.25 g of triethylamine, 0.7 g of benzyl bromide and 10 ml of hexamethylphosphoric triamide was stirred at room temperature overnight. The reaction mixture was then poured into water and extracted with ethyl acetate. The extract was dried over anhydrous sodium sulfate, and the solvent was evaporated off under reduced pressure. The residue was purified by silica gel column chromatography, using as eluent a 2:1 by volume mixture of hexane and ethyl acetate. The resulting product was a yellow powder having the following physical properties.

Melting point: 209° to 216° C.

Nuclear Magnetic Resonance Spectrum (hexadeuterated dimethyl sulfoxide) δ ppm: 1.33 (3H, triplet, J=7 Hz), 4.42 (2H, quartet, J=7 Hz), 4.87 (2H, singlet), 5.20 (2H, singlet), 7.07 (1H, triplet, J=7Hz), 7.3–7.4 (7H, not defined), 7.49 (2H, multiplet), 7.72 (1H, singlet), 8.95 (1H, broad singlet, disappeared on adding deuterium oxide), 11.02 (1H, broad singlet, disappeared on adding deuterium oxide).

EXAMPLE 34

1-Isopropoxyarbonyloxyethyl 5-{1-ethoxycarbonyl-1-[2-(3-phenylureido)thiazol-4-yl]methylene}rhodanine-3-acetate 1 g of 5-{1-ethoxycarbonyl-1-[2-(3-phenylureido)-thiazol-4-yl]methylene}rhodanine-3-acetic acid and 0.65 g of 1,8-diazabicyclo[5.4.0]undec-7-ene were dissolved in 16 ml of dimethylacetamide, and 8 ml of 1-iodoethyl isopropyl carbonate were added dropwise thereto with stirring under ice-cooling. The resulting mixture was stirred for 4 hours under ice-cooling, and then at room temperature for 2 days. The reaction mixture was then poured into water and extracted with ethyl acetate. The extract was dried over anhydrous magnesium sulfate, the solvent was evaporated off under reduced pressure, and the residue was purified by silica gel column chromatography, using as eluent a 3:1 by volume mixture of hexane and ethyl acetate. The powdery product obtained after evaporating off the solvent was washed with a small amount of the above eluent mixture, giving the desired compound as a yellow powder.

Melting point: 188° to 190° C.

Nuclear Magnetic Resonance Spectrum (hexadeuterated dimethyl sulfoxide) δ ppm: 1.30 (3H, doublet, J=6 Hz), 1.31 (3H, doublet, J=6 Hz), 1.40 (3H, triplet, J=7 Hz), 1.54 (3H, doublet, J=5.5 Hz), 4.48 (2H, quartet, J=7 Hz), 4.72 and 4.84 (2H, AB, J=17 Hz), 4.90 (1H, septet, J=6 Hz), 6.81 (1H, quartet, J=5.5 Hz), 7.16 (1H, triplet, J=7 Hz), 7.19 (1H, singlet), 7.36 (2H, triplet, J=7 Hz), 7.48 (2H, doublet, J=7 Hz), 7.8–8.0 (1H, broad, disappeared on adding deuterium oxide), 9.07 (1H, broad singlet, disappeared on adding deuterium oxide).

EXAMPLE 35

Sodium 5-{1-ethoxycarbonyl-1-[2-(3-phenylureido)thiazol-4-yl]met hylene]rhodanine-3-acetate tetrahydrate A mixture comprising 2.46 g of 5-{1-ethoxycarbonyl-1-[2-(3-phenylureido)thiazol-4-yl]methylene]rhodanine-3-acetic acid, 0.54 g of sodium methoxide and 30 ml of absolute ethanol was stirred for 1 hour under ice-cooling, then treated by ultrasonication at room temperature for 30 minutes. The reaction mixture was then poured into anhydrous ether and the crystalline product which precipitated out was collected by filtration, giving the desired compound as a reddish-brown powder.

Melting point: over 300° C.

Nuclear Magnetic Resonance spectrum (hexadeuterated dimethyl sulfoxide) δ ppm: 1.32 (3H, triplet, J=7 Hz), 4.29 (2H, singlet), 4.35 (2H, quartet, J=7 Hz), 6.75 (1H, triplet, J=8 Hz), 7.04 (1H, singlet), 7.14 (2H, triplet, J=8 Hz), 7.59 (2H, doublet, J=8 Hz), 8.79 (1H, broad singlet, disappeared on adding deuterium oxide).

EXAMPLE 36

5{1-Isobutoxycarbonyl-1-[2-(3-phenylureido)thiazol-4-yl]methylene}rhodanine-3-acetic acid Following a procedure similar to that described in Example 1, the desired compound was prepared from 160 mg of isobutyl 2-(3-phenylureido)thiazol-4-ylglyoxylate, 90 mg of rhodanine-3-acetic acid, 50 mg of ammonium chloride, 0.05 ml of 28% v/v aqueous ammonia and 2 ml of ethanol. The resulting product was a yellow powder having the following physical properties.

Melting point: 235° to 239° C. (with decomposition).

Nuclear Magnetic Resonance Spectrum (hexadeuterated dimethyl sulfoxide) δ ppm: 0.93 (6H, doublet, J=7 Hz), 2.03 (1H, septet. J=7 Hz), 4.15 (2H, doublet, J=7 Hz), 4.69 (2H, broad singlet), 7.07 (1H, triplet, J=8 Hz), 7.34 (2H, triplet, J=8 Hz), 7.49 (2H, doublet, J=8 Hz), 7.66 (1H, singlet), 8.96 (1H, broad singlet, disappeared on adding deuterium oxide), 11.03 (1H, broad singlet, disappeared on adding deuterium oxide), 13–13.7 (1H, broad, disappeared on adding deuterium oxide).

EXAMPLE 37

5-{1-Carboxy-1-[2-(3-phenylureido)thiazol-4-yl]methylene}rhodanine-3-acetic acid ¼ hydrate Following a procedure similar to that described in Preparation 1, the desired compound was prepared from 1 g of 5-[1-(2-aminothiazol-4-yl)-1-carboxymethylene]rhodanine-3-acetic acid, 3.9 g of phenyl isocyanate and 10 ml of hexamethylphosphoric triamide. The resulting product was a ellow powder having the following physical properties.

Melting point: circa 225° C. (with decomposition).

Nuclear Magnetic Resonance Spectrum (hexadeuterated dimethyl sulfoxide) δ ppm: 4.63 (2H, singlet), 7.04 (1H, triplet, J=8 Hz), 7.23 (1H, singlet), 7.32 (2H, triplet, J=8 Hz), 7.48 (2H, doublet, J=8 Hz), 8.92 (1H, singlet, disappeared on adding deuterium oxide), 10.3–10.8 (1H, broad, disappeared on adding deuterium oxide), 10.99 (1H, singlet, disappeared on adding deuterium oxide), 13.0–13.8 (1H, broad, disappeared on adding deuterium oxide).

EXAMPLE 38

5-{1-Ethoxycarbonyl-1-[2-(3-o-fluorophenylureido)-thiazol-4-yl]methylene}rhodanine-3-acetic acid 2/5 acetic acid adduct Following a procedure similar to that described in Example 1, the desired compound was prepared from 1.7 g of ethyl 2-(3-o-fluorophenylureido)thiazol-4-ylglyoxylate, 0.96 g of rhodanine-3-acetic acid, 0.5 g of ammonium chloride, 0.5 ml of 28% v/v aqueous ammonia and 20 ml of ethanol. The resulting product was a yellow powder having the following physical properties.

Melting point: 220° C. (with decomposition).

Nuclear Magnetic Resonance Spectrum (hexadeuterated dimethyl sulfoxide) δ ppm: 1.34 (3H, triplet, J=7 Hz), 1.91 (1.2H, singlet), 4.42 (2H, quartet, J=7 Hz), 4.69 (2H, broad singlet), 7.13 (1H, doublet of doublets of doublets, J=8, 5, and 2 Hz), 7.21 (1H, broad triplet, J=8 Hz), 7.30 (1H, doublet of doublets of doublets, J=11, 8, and 1.5 Hz), 7.72 (1H, singlet), 8.12 (1H, doublet of triplets, J=2 and 8 Hz), 8.93 (1H, broad singlet), 11.30 (1H, broad singlet).

EXAMPLE 39

E and Z isomers of Ethyl 5-{1-ethoxycarbonyl-1-[2-(3-o-fluorophenylureido)-thiazol-4-yl]methylenerhodanine-3-acetate A mixture comprising 5 g of 5-{1-ethoxycarhonyl-[1-[2-(3-o-fluorophenylureido)thiazol-4-yl]methylene}rhodanine-3-acetic acid, 10 g of ethanol and 75 ml of a 4N dioxane solution of hydrogen chloride was left to stand at room temperature for 5 days. The reaction mixture was then poured into water and extracted with ethyl acetate. The extract was dried over anhydrous sodium sulfate, and the solvent was evaporated off under reduced pressure. The residue was recrystallized from a mixture of hexane and ethyl acetate (about 1:1 by volume). The resulting crystals were purified by silica gel column chromatography, using as eluent by volume mixture of hexane and ethyl acetate. giving the desired compound (a) as an orange powder.

Melting point: 93° to 100° C.

Thin-layer chromatography: Rf=circa 0.29 (developing solvent: 3:1 mixture of hexane and ethyl acetate).

Nuclear Magnetic Resonance Spectrum (hexadeuterated dimethyl sulfoxide) δ ppm: 1.18 (3H, triplet, J=7 Hz), 1.21 (3H, triplet, J=7 Hz), 4.14 (2H, quartet, J=7 Hz), 4.29 (2H, quartet, J=7 Hz), 4.74 (2H, singlet), 7.05–7.3 (3H, multiplet), 7.31 (1H, singlet), 8.08–8.16 (1H, multiplet), 8.93 (1H, broad singlet), 10.84 (1H, broad singlet).

The mother liquor from the recrystallization of the compound (a) was then concentrated under reduced pressure and the residue was purified by silica gel column chromatography, using as eluent a 5:1 by volume mixture of hexane and ethyl acetate, giving the desired compound (b) as a yellow powder.

Melting point: 230° to 235 ° C. (with decomposition).

Thin-layer chromatograpy: Rf=circa 0.53 (developing solvent: 3:1 mixture of hexane and ethyl acetate).

Nuclear Magnetic Resonance Spectrum (hexadeuterated dimethyl sulfoxide) δ ppm: 1.20 (3H, triplet, J=7 Hz), 1.33 (3H, triplet, J=7 Hz), 4.17 (2H, guartet. J=7 Hz), 4.42 (2H, quartet, J=7 Hz), 4.79 (2H, singlet), 7.05–7.35 (3H, multiplet), 7.73 (1H, singlet), 8.08–8.16 (1H, multiplet), 8.91 (1H, broad singlet, disappeared on adding deuterium oxide), 11.31 (1H, broad singlet, disappeared on adding deuterium oxide).

EXAMPLE 40

5{1-Ethoxycarbonyl-1-[2-(3-m-fluorophenylureido)-thiazol-4-yl]methylene}rhodanine-3-acetic acid hemihydrate Following a procedure similar to that described in Example 1, the desired compound was prepared from 1.7 g of ethyl 2-(3-m-fluorophenylureido)thiazol-4-ylglyoxylate, 0.96 g of rhodanine-3-acetic acid, 0.5 g of ammonium chloride, 0.5 ml of 28% v/v aqueous ammonia and 20 ml of ethanol. The resulting product was an orange powder having the following physical properties.

Melting point: 193° to 197° C.

Nuclear Magnetic Resonance Spectrum (hexadeuterated dimethyl sulfoxide) δ ppm: 1.34 (3H, triplet, J=7 Hz), 4.42 (2H, quartet, J=7 Hz), 4.70 (2H, singlet), 6.90 (1H, doublet of triplets, J=2 and 8 Hz), 7.19 (1H, doublet of triplets, J=7 and 1 Hz), 7.38 (1H, doublet of triplets, J=7 and 8 Hz), 7.48 (1H, doublet of triplets, J=11 and 2 Hz). 7.71 (1H, singlet), 9.16 (1H, broad singlet disappeared on adding deuterium oxide), 11.11 (1H, broad singlet, disappeared on adding deuterium oxide), 13.0–13.7 (1H, broad singlet, disappeared on adding deuterium oxide).

EXAMPLE 41

E and Z isomers of Ethyl 5-{1-ethoxycarbonyl-1-2-(3-p-fluorophenylureido)-thiazol-4-yl]methylene}rhodanine-3-acetate Following reaction and separation procedures similar to those described in Examples 30 and 39, the desired compounds (a) and (b) were prepared from 4.04 g of 5-[1-ethoxycarbonyl-1-[2-(3-p-fluorophenylureido)-thiazol-4-yl]methylene rhodanine-3-acetic acid, 8 g of ethanol and 60 ml of a 4N dioxane solution of hydrogen chloride. Compound (a) was a yellow powder having the following physical properties.

Softening point: 115° to 125° C.
Thin-layer chromatograpy: Rf=circa 0.70 (developing solvent: 1:1 mixture of hexane and ethyl acetate).
Nuclear Magnetic Resonance Spectrum (hexadeuterated acetone) δ ppm: 1.26 (3H, triplet, J=7 Hz), 1.38 (3H, triplet, J=7 Hz), 4.21 (2H, quartet, J=7 Hz), 4.47 (2H, quartet, J=7 Hz), 4.83 (2H, singlet), 7.13 (2H, triplet, J=9 Hz), 7.59 (1H, singlet), 7.61 (2H, doublet of doublets, J=9 and 5 Hz), 8.61 (1H, broad singlet), 10.45 (1H, broad singlet).

Compound (b) was a reddish-brown powder having the following physical properties.

Softening point: 110° to 115° C.
Thin-layer chromatograpy: Rf=circa 0.41 (developing solvent: 1:1 mixture of hexane and ethyl acetate).
Nuclear Magnetic Resonance Spectrum (hexadeuterated acetone) δ ppm: 1.23 (3H, triplet, J=7 Hz), 1.26 (3H, triplet, J=7 Hz), 4.18 (2H, quartet, J=7 Hz), 4.32 (2H, quartet, J=7 Hz), 4.76 (2H, singlet), 7.10 (2H, triplet, J=9 Hz), 7.28 (1H, singlet), 7.58 (2H, doublet of doublets, J=9 and 5 Hz), 8.75 (1H, broad singlet), 9.85 (1H, broad singlet).

EXAMPLE 42

Sodium 5-{1-ethoxycarbonyl-1-[2-(3-p-fluorophenylureido)-thiazol-4-yl]methylene}rhodanine-3-acetate Following a procedure similar to that described in Example 35, the desired compound was prepared from 1 g of 1-ethoxycarbonyl-1-[2-(3-p-fluorophenylureido)-thiazol-4-yl]methylene}rhodanine-3-acetic acid, 0.24 g of sodium methoxide and 20 ml of absolute ethanol. The resulting product was a reddish-brown powder having the following physical properties.

Melting point: 187° to 200° C. (with decomposition).
Nuclear Magnetic Resonance Spectrum (hexadeuterated dimethyl sulfoxide) δ ppm: 1.31 (3H, triplet, J=7 Hz), 4.25 (2H, singlet), 4.35 (2H, quartet, J=7 Hz), 6.96 (2H, triplet, J=9 Hz), 7.03 (1H, singlet), 7.59 (2H, doublet of doublets, J=9 and 5 Hz), 8.86 (1H, broad singlet).

EXAMPLE 43

5-{1-[2-[3-(2,4-Difluorophenyl)ureido]-thiazol-4-yl]-1-ethoxycarbonvlmethylene)rhodanine-3-acetic acid hemihydrate Following a procedure similar to that described in Example 1, the desired compound was prepared from 1.8 g of ethyl 2-[3-(2,4-difluorophenyl)ureido]thiazol-4-ylglyoxylate, 0.96 g of rhodanine-3-acetic acid, 0.5 g of ammonium chloride, 0.5 ml of 28% v/v aqueous ammonia and 30 ml of ethanol. The resulting product was a yellow powder having the following physical properties.

Melting point: 235° to 243° C. (with decomposition).
Nuclear Magnetic Resonance Spectrum (hexadeuterated dimethyl sulfoxide) δ ppm: 1.34 (3H, triplet, J=7 Hz), 4.42 (2H, quartet, J=7 Hz), 4.69 (2H, broad singlet), 7.10 (1H, broad triplet, J=9 Hz), 7.37 (1H, doublet of doublets of doublets, J=3, 9, and 11 Hz), 7.71 (1H, singlet), 8.06 (1H, doublet of triplets, J=6 and 9 Hz), 8.87 (1H, broad doublet, J=1 Hz, disappeared on adding deuterium oxide), 11.30 (1H, broad singlet, disappeared on adding deuterium oxide).

EXAMPLE 44

5-{1-Ethoxycarbonyl-1-[2-[3-(4-fluoro-3-nitrophenyl)ureido]thiazol-4-yl]methylene}rhodanine-3-acetic acid hemihydrate ½ acetic acid adduct Following a procedure similar to that described in Example 1, 1.13 g of the desired compound was prepared from 2.3 g of ethyl 2-[3-(4-fluoro-3-nitrophenyl)ureido]thiazol-4-ylglyoxylate, 0.95 g of rhodanine-3-acetic acid, 0.5 g of ammonium chloride, 0.5 ml of 28% v/v aqueous ammonia and 30 ml of ethanol. The resulting product was a yellow powder having the following physical properties.

Melting point: circa 250° C. (with decomposition).
Nuclear Magnetic Resonance Spectrum (hexadeuterated dimethyl sulfoxide) δ ppm: 1.34 (3H, triplet, J=7 Hz), 1.91 (1.5H, singlet), 4.42 (2H, quartet, J=7 Hz), 4.69 (2H, broad singlet), 7.58 (1H, doublet of doublets, J=9 and 11 Hz). 7.74 (1H, singlet). 7.75–7.80 (1H, multiplet), 8.43 (1H, doublet of doublets, J=6 and 3 Hz), 9.40 (1H, broad singlet disappeared on adding deuterium oxide), 11.35 (1H, broad singlet, disappeared on adding deuterium oxide).

EXAMPLE 45

5-{1-Ethoxycarbonyl-1-[2-[3-(2,4,6-trifluorophenyl)ureido]thiazol-4-yl]methylene}rhodanine-3-acetic acid dihydrate Following a procedure similar to that described in Example 1, 0.58 g of the desired compound was prepared from 700 mg of ethyl 2-[3-(2,4,6-trifluorophenyl)ureido]thiazol-4-yl-glyoxylate, 350 mg of rhodanine-3-acetic acid, 190 mg of ammonium chloride, 0.2 ml of 28% v/v aqueous ammonia and 10 ml of ethanol. The resulting product was a yellow powder having the following physical properties.

Melting point: 183° to 187° C. (with decomposition).
Nuclear Magnetic Resonance Spectrum (hexadeuterated dimethyl sulfoxide) δ ppm: 1.33 (3H, triplet, J=7 Hz), 4.41 (2H, quartet, J=7 Hz), 4.69 (2H, broad singlet), 7.32 (2H, doublet of doublets, J=9 and 8 Hz), 7.69 (1H, singlet), 8.38 (1H, broad singlet, disappeared on adding deuterium oxide), 11.60 (1H, broad singlet, disappeared on adding deuterium oxide), 13.0–13.7 (1H, broad, disappeared on adding deuterium oxide).

EXAMPLE 46

5-{1-Ethoxycarbonyl-1-[2-[3-(3,4,5-trimethoxyphenyl)ureido]thiazol-4-yl]methylene}rhodanine-3-acetic acid sesquihydrate Following a procedure similar to that described in Example 1, the desired compound was prepared from 1.1 g of ethyl 2-[3-(3,4,5-trimethoxyphenyl)ureido]thiazol-4-ylglyoxylate. 0.48 9 of rhodanine-3-acetic acid. 0.25 g of ammonium chloride. 0.25 ml of 28% v/v aqueous ammonia and ml of ethanol, in the form of brown prismatic crystals having the following physical properties.

Melting point: 173° to 180 ° C.

Nuclear Magnetic Resonance Spectrum (hexadeuterated dimethyl sulfoxide) δ ppm: 1.34 (3H, triplet, J=7 Hz), 3.63 (3H, singlet), 3.78 (6H. singlet). 4.42 (2H, quartet, J=7 Hz), 4.69 (2H, broad singlet), 6.81 (2H, singlet), 7.70 (1H, singlet), 8.92 (1H, broad singlet, disappeared on adding deuterium oxide), 11.04 (1H, broad singlet, disappeared on adding deuterium oxide), 13.1–13.8 (1H, broad, disappeared on adding deuterium oxide).

EXAMPLE 47

5-{-[1-2-(3-o-Chlorophenylureido)thiazol-4-yl]-1-ethoxycarbonylmethylene}rhodanine-3-acetic acid monohydrate Following a procedure similar to that described in Example 1, the desired compound was prepared from 1.77 g of ethyl 2-(3-o-chlorophenylureido)thiazol-4-ylglyoxylate, 0.95 g of rhodanine-3-acetic acid, 0.5 g of ammonium chloride, 0.5 ml of 28% v/v aqueous ammonia and 25 ml of ethanol. The resulting product was a yellow powder having the following physical properties.

Melting point 230° to 238° C. (with decomposition).

Nuclear Magnetic Resonance Spectrum (hexadeuterated dimethyl sulfoxide) δ ppm: 1.34 (3H, triplet, J=7 Hz), 4.42 (2H, quartet, J=7 Hz), 4.69 (2H, broad singlet), 7.13 (1H, doublet of triplets, J=8 and 1.5 Hz), 7.36 (1H, doublet of triplets, J=8 and 1.5 Hz). 7.52 (1H, doublet of doublets, J=8 and 1.5 Hz). 7.72 (1H, singlet), 8.17 (1H, doublet of doublets, J=8 and 1.5 Hz), 8.78 (1H, broad singlet, disappeared on adding deuterium oxide), 11.64 (1H, broad singlet, disappeared on adding deuterium oxide), 13–14 (1H, broad, disappeared on adding deuterium oxide).

EXAMPLE 48

5-{1-Ethoxycarbonyl-1-[2-(3-p-tolylureido)thiazol-4-yl]methylene}rhodanine-3-acetic acid Following a procedure similar to that described in Example 1, the desired compound was prepared using 4.8 g of ethyl 2-(3-p-tolylureido)thiazol-4-ylglyoxylate, 2.5 g of rhodanine-3-acetic acid, 1.5 g of ammonium chloride, 1.5 ml of 20% v/v aqueous ammonia and 50 ml of ethanol. The resulting product was a yellow powder having the following physical properties.

Melting point; 240° to 245° C. (with decomposition).

Nuclear Magnetic Resonance Spectrum (hexadeuterated dimethyl sulfoxide) δ ppm: 1.34 (3H, triplet. J=7 Hz). 2.27 (3H, singlet), 4.42 (2H, quartet, J=7 Hz), 4.69 (2H, broad singlet). 7.15 (2H, doublet. J=8 Hz). 7.37 (2H, doublet, J=8 Hz), 7.69 (1H, singlet), 8.86 (1H, broad singlet, disappeared on adding deuterium oxide), 10.99 g (1H, broad singlet, disappeared on adding deuterium oxide), 13.0–13.8 (1H, broad singlet, disappeared on adding deuterium oxide).

EXAMPLE 49

5-{1-Ethoxycarbonyl-1-[2-[3-(2,6-xylyl)ureido]thiazol-4-yl]-methylene}rhodanine-3-acetic acid Following a procedure similar to that described in Example 1, the desired compound was prepared using 1.74 g of ethyl 2-[3-(2,6-xylyl)ureido]thiazol-4-ylglyoxylate, 0.96 g of rhodanine-3-acetic acid, O.5 g of ammonium chloride. 0.5 ml of 28% v/v aqueous ammonia and 20 ml of ethanol. The resulting product was a yellow powder having the following physical properties.

Melting point: 240° to 245° C. (with decomposition).

Nuclear Magnetic Resonance Spectrum (hexadeuterated dimethyl sulfoxide) δ ppm: 1.33 (3H, triplet, J=7 Hz), 2.21 (6H, singlet), 4.41 (2H, quartet. J=7 Hz). 4.69 (2H, broad singlet), 7.12 (3H, singlet), 7.65 (1H, singlet), 8.14 (1H, broad singlet, disappeared on adding deuterium oxide), 11.24 (1H, broad singlet, disappeared on adding deuterium oxide), 12.9–13.9 (1H, broad, disappeared on adding deuterium oxide).

EXAMPLE 50

5{-[1-Ethoxycarbonyl-1-[2-(3-p-nitrophenylureido)-thiazol-4-yl]methylene}rhodanine-3-acetic acid bis(dimethylformamide) adduct Following a procedure similar to that described in Example 1, the desired compound was prepared from 3.7 g of ethyl 2-(3-p-nitrophenylureido)thiazol-4-ylglyoxylate, 1.9 g of rhodanine-3-acetic acid, 1 g of ammonium chloride, 1 ml of 28% v/v aqueous ammonia and 40 ml of ethanol. The resulting product was a yellow powder having the following physical properties.

Melting point: 285° to 290 ° C. (with decomposition).

Nuclear Magnetic Resonance Spectrum (hexadeuterated dimethyl sulfoxide) δ ppm: 1.34 (3H, triplet, J=7 Hz), 2.73 (6H, singlet), 2.89 (6H, singlet), 4.42 (2H, quartet, J=7 Hz), 4.70 (2H, broad singlet), 7.75 (2H. doublet, J=9 Hz). 7.75 (1H, singlet), 7.95 (2H, singlet), 8.25 (2H, doublet, J=9 Hz), 9.64 (1H, broad singlet, disappeared on adding deuterium oxide), 11.30 (1H, broad singlet, disappeared on adding deuterium oxide), 13.0–13.8 (1H, broad singlet, disappeared on adding deuterium oxide).

EXAMPLE 51

5-{1-Ethoxycarbonyl-1-[2-(3-o-trifluoromethylphenylureido)thiazol-4-yl]-methylene}rhodanine-3-acetic acid Following a procedure similar to that described in Example 1, the desired compound was prepared using 3.9 g of ethyl 2-(3-o-trifluoromethylphenylureido)-thiazol-4-ylglyoxylate, 1.9 g of rhodanine-3-acetic acid, 1 g of ammonium chloride, 1 ml of 28% v/v aqueous ammonia and 50 ml of ethanol. The resulting product was a yellow powder having the following physical properties.

Melting point: 245° to 250° C. (with decomposition).

Nuclear Magnetic Resonance Spectrum (hexadeuterated dimethyl sulfoxide) δ ppm: 1.34 (3H, triplet, J=7 Hz), 4.42 (2H, quartet, J=7 Hz), 4.70 (2H, broad singlet), 7.39 (1H, triplet, J=8 Hz), 7.65–7.75 (1H, not defined), 7.72 (1H, singlet), 7.75 (1H, doublet, J=8 HZ),

EXAMPLE 52

5-{1-Ethoxycarbonyl-1-[2-(3-p-trifluoromethyl-phenylureido)thiazol-4-yl]methylene}rhodanine-3-acetic acid Following a procedure similar to that described in Example 1, the desired compound was prepared from 3.9 g of ethyl 2-(3-p-trifluoromethylphenylureido)-thiazol-4-ylglyoxylate, 1.9 g of rhodanine-3-acetic acid, 1 g of ammonium chloride, 1 ml of 28% v/v aqueous ammonia and 30 ml of ethanol. The resulting product was a yellow powder having the following physical properties.

Melting point: 160° to 170 ° C. (with decomposition).
Nuclear Magnetic Resonance Spectrum (hexadeuterated dimethyl sulfoxide) δ ppm: 1.34 (3H, triplet, J=7 Hz), 4.42 (2H, quartet, J=7 Hz), 4.70 (2H, broad singlet), 7.70 (4H, singlet), 7.73 (1H, singlet), 9.34 (1H, broad singlet. disappeared on adding deuterium oxide), 11.17 (1H, broad singlet, disappeared on adding deuterium oxide).

EXAMPLE 53

5{-1-[2-(3,3-Diphenylureido)thiazol-4-yl]-1-ethoxy-carbonylmethylene}rhodanine-3-acetic acid Following a procedure similar to that described in Example 1, the desired compound was prepared from 130 mg of ethyl 2-(3,3-diphenylureido)thiazol-4-ylglyoxylate, 60 mg of rhodanine-3-acetic acid, 30 mg of ammonium chloride, 0.03 ml of 28% v/v aqueous ammonia and 5 ml of ethanol. The resulting product was a yellow powder having the following physical properties.

Melting point: 205° to 230 ° C. (with decomposition).
Nuclear Magnetic Resonance Spectrum (hexadeuterated dimethyl sulfoxide) δ ppm: 1.32 (3H, triplet, J=7 Hz), 4.40 (2H, quartet, J=7 Hz), 4.66 (2H, broad singlet), 7.27-7.34 (6H, multiplet), 7.44 (4H, triplet, J=8 Hz), 7.69 (1H, singlet), 11.18(1H, broad singlet. disappeared on adding deuterium oxide), 12.5-14.0 (1H, broad, disappeared on adding deuterium oxide).

EXAMPLE 54

5{-Ethoxycarbonyl-1-[2-(3-methylureido)thiazol-4-yl]methylene}rhodanine-3-acetic acid Following a procedure similar to that described in Example 1, the desired compound was prepared from 3.17 g of ethyl 2-(3-methylureido)thiazol-4-ylglyoxylate, 2.2 g of rhodanine-3-acetic acid, 1.2 g of ammonium chloride, 1.2 ml of 28% v/v aqueous ammonia and 50 ml of ethanol. The resulting product was a yellow powder having the following physical properties.

Melting point: 241° to 245 ° C. (with decomposition).
Nuclear Magnetic Resonance Spectrum (hexadeuterated dimethyl sulfoxide) δ ppm: 1.32 (3H, triplet, J=7 Hz). 2.73 (3H, doublet, J=5 Hz, converted to singlet on adding deuterium oxide), 4.40 (2H, quartet, J=7 Hz). 4.68 (2H, broad singlet), 6.47 (1H, broad doublet, J=5 Hz, disappeared on adding deuterium oxide), 7.60 (1H, singlet), 11.03 (1H, broad singlet, disappeared on adding deuterium oxide), 13.0-13.7 (1H, broad, disappeared on adding deuterium oxide).

EXAMPLE 55

5-{1-[2-(3-Benzylureido)thiazol-4-yl]-1-ethoxycarbonylmethylene}rhodanine-3-acetic acid dihydrate Following a procedure similar to that described in Example 1, the desired compound was prepared from 1.67 g of ethyl 2-(3-benzylureido)thiazol-4-ylglyoxylate, 0.95 g of rhodanine-3-acetic acid, 0.5 g of ammonium chloride, 0.5 ml of 28% v/v aqueous ammonia and 25 ml of ethanol. The resulting product was a yellow powder having the following physical properties.

Melting point: 220° to 225 ° C. (with decomposition).
Nuclear Magnetic Resonance Spectrum (hexadeuterated dimethyl sulfoxide) δ ppm: 1.32 (3H, triplet, J=7 Hz), 4.35-4.45 (2H, not defined), 4.39 (2H, broad singlet), 4.68 (2H, broad singlet), 7.08 (1H, broad triplet, J=6 Hz, disappeared on adding deuterium oxide), 7.2-7.4 (5H, multiplet), 7.62 (1H, singlet), 11.06 (1H, broad singlet, disappeared on adding deuterium oxide), 13.0-13.8 (1H, broad, disappeared on adding deuterium oxide).

EXAMPLE 56

5-{-1-[2-(3-Cyclohexylureido)thiazol-4-yl]-1-ethoxycarbonylmethylene}rhodanine-3-acetic acid Following a procedure similar to that described in Example 1, the desired compound was prepared using 1 g of ethyl 2-(3-cyclohexylureido)thiazol-4-ylglyoxylate, 0.58 g of rhodanine-3-acetic acid, 0.3 g of ammonium chloride, 0.3 ml of 28% v/v aqueous ammonia and 10 ml of ethanol. The resulting product was a yellow powder having the following physical properties.

Melting point: 245° to 248 ° C. (with decomposition).
Nuclear Magnetic Resonance Spectrum (hexadeuterated dimethyl sulfoxide) δ ppm: 1.15-1.45 (5H, multiplet), 1.32 (3H, triplet, J=7 Hz). 1.45-1.6 (1H, multiplet), 1.6-1.75 (2H, multiplet), 1.75-1.9 (2H, multiplet), 3.42-3.62 (1H, multiplet). 4.40 (2H, quartet, J=7 Hz). 4.68 (2H, singlet), 6.56 (1H, broad doublet, J=8 Hz), 7.60 (1H, singlet), 10.65 (1H, broad singlet), 12.9-13.9 (1H, broad).

EXAMPLE 57

5-{(2E)-3-[2-(3-p-bromophenylureido)thiazol-4-yl)-allylidene}rhodanine-3-acetic acid hemihydrate Following a procedure similar to that described in Example 1, the desired compound was prepared using 0.4 g of (E)-3-[2-(3-p-bromophenylureido)thiazol-4-yl]acrylaldehyde, 0.2 g of rhodanine-3-acetic acid, 0.15 g of ammonium chloride, 0.15 ml of 28% v/v aqueous ammonia and 10 ml of ethanol. The resulting product was a brownish-orange powder having the following physical properties.

Melting point: 215° to 220 ° C. (with decomposition).
Nuclear Magnetic Resonance Spectrum (hexadeuterated dimethyl sulfoxide) δ ppm: 4.70 (2H, broad singlet), 6.89 (1H, doublet of doublets, J=15 and 12 Hz). 7.34 (1H, doublet, J=15 Hz), 7.47 and 7.50 (4H, $A_2B_2$, J=9 Hz), 7.55 (1H, singlet), 7.64 (1H, doublet, J=12 Hz), 9.06 (1H, broad singlet, disappeared on adding deuterium oxide), 10.8-11.2 (1H, broad, disappeared on adding deuterium oxide), 13.0-13.8 (1H, broad, disappeared on adding deuterium oxide).

EXAMPLE 58

5-[2-(3-Phenylureido)thiazol-4-ylmethylene]thiazolidine-2,4-dione ⅓ hydrate

Following a procedure similar to that described in Example 1, the desired compound was prepared from 1.1 g of 2-(3-phenylureido)thiazole-4-carbaldehyde, 0.52 g of 2,4-thiazolidinedione, 0.6 g of ammonium chloride, 0.6 ml of 28% v/v aqueous ammonia and 20 ml of ethanol. The resulting product was a yellow powder having the following physical properties.

Melting point: over 300 °C.

Nuclear Magnetic Resonance Spectrum (hexadeuterated dimethyl sulfoxide) δ ppm: 7.06 (1H, triplet, J=8 Hz), 7.33 (2H, triplet, J=8 Hz), 7.48 (2H, doublet of doublets, J=8 and 1 Hz), 7.63 (1H, singlet), 7.78 (1H, singlet), 8.96 (1H, broad singlet, disappeared on adding deuterium oxide), 10.70 (1H, broad singlet, disappeared on adding deuterium oxide), 12.32 (1H, broad singlet, disappeared on adding deuterium oxide).

EXAMPLE 59

5-[1-(2-Dimethylaminothiazol-4-yl)-1-ethoxycarbonyl methylene]rhodanine-3-acetic acid The reaction described in Example 1 was repeated, but using 0.5 g of ethyl 2-dimethylaminothiazol-4-ylglyoxylate, 0.35 g of rhodanine-3-acetic acid, 0.26 g of ammonium chloride, 0.3 ml of 28% v/v aqueous ammonia. and 5 ml of giving the title compound as orange needles.

Melting point: 275° to 278° C. (with decomposition).

Nuclear Magnetic Resonance Spectrum (hexadeuterated dimethyl sulfoxide) δ ppm: 1.32 (3H, triplet, J=7 Hz), 3.15 (6H, singlet), 4.39 (2H, quartet, J=7 Hz), 4.67 (2H, singlet), 7.34 (1H, singlet), 13.2-13.6 (1H, broad).

EXAMPLE 60

5-(2-Diethylaminothiazol-4-ylmethylene)-rhodanine-3-acetic acid

The reaction described in Example 1 was repeated, but using 1.2 g of 2-diethylaminothiazole-4-carbaldehyde, 1 g of rhodanine-3-acetic acid. 0.8 g of ammonium chloride. 0.8 ml of 28% v/v aqueous ammonia, and 25 ml of ethanol, giving the title compound as yellowish-brown needles.

Melting point: 257° to 260° C. (with decomposition).

Nuclear Magnetic Resonance Spectrum (hexadeuterated dimethyl sulfoxide) δ ppm: 1.23 (6H, triplet, J=7 Hz). 3.52 (4H, quartet, J=7 Hz), 4.70 (2H, singlet), 7.56 (1H, singlet). 7.59 (1H, singlet), 13.2-13.5 (1H, broad).

EXAMPLE 61

Ethyl 5-{1-ethoxycarbonyl-1-[2-(3-phenylthioureido)-thiazol-4-yl]methylene}rhodanine-3 -acetate A mixture comprising 10 g of 5-{1-ethoxycarbonyl-1-[2-(3-phenylthioureido)thiazol-4-yl]methylene}rhodanine-3acetic acid 20 g of ethanol and 150 ml of a 4N dioxane solution of hydrogen chloride was left to stand at room temperature for 4.5 days. The reaction mixture was then poured into water and extracted with ethyl acetate. The extract was washed with aqueous potassium carbonate solution and then with aqueous sodium chloride solution, and was then dried over anhydrous sodium sulfate. The solvent was evaporated off under reduced pressure, and the residue was purified by silica gel column chromatography, using as eluent a 1:1 by volume mixture of hexane and ethyl acetate. The resulting crystalline product was recrystallised from a 1:5 by volume mixture of hexane and ethyl acetate, giving a yellow powder having the following physical properties.

Melting point: 195° to 200 °C.

Nuclear Magnetic Resonance Spectrum (hexadeuterated dimethyl sulfoxide) δ ppm: 1 17 (3H, triplet, J=7 Hz), 1.21 (3H, triplet, J=7 Hz), 4.13 (2H, quartet, J=7 Hz), 4.29 (2H, quartet, J=7 Hz), 4.75 (2H, broad singlet), 6.8-7.9 (6H, multiplet).

EXAMPLE 62

Ethyl 5-{1-[2-(3-p-chlorophenylthioureido)thiazol-4-yl]-1-ethoxycarbonylmethylene}rhodanine-3-acetate A mixture comprising 4.8 g of 5-{1-[2-(3-p-chlorophenylthioureido)thiazol-4-yl]-1-ethoxycarbonylmethylene}-rhodanine-3-acetic acid, 10 g of ethanol and 50 ml of a 4N dioxane solution of hydrogen chloride was left to stand at room temperature for 4.5 days. The reaction mixture was then poured into water and extracted with ethyl acetate. The extract was washed with aqueous sodium chloride solution, and was then dried over anhydrous sodium sulfate. The solvent was evaporated off under reduced pressure, and the residue was recrystallized from a circa 1:1 by volume mixture of hexane and ethyl acetate. The resulting product was an orange powder having the following physical properties.

Melting point: 175° to 177° C.

Nuclear Magnetic Resonance Spectrum (hexadeuterated dimethyl sulfoxide) δ ppm: 1.17 (6H, triplet, J=7 Hz), 4.13 (2H, quartet, J=7 Hz). 4.30 (2H, quartet, J=7 Hz), 4.76 (2H, broad singlet), 7.0-7.9 (5H, multiplet).

EXAMPLE 63

5-{1-Ethoxycarbonyl-1-[2-(3-o-fluorophenylthioureido)-thiazol-4-yl]methylene}rhodanine-3-acetic acid ¼ hydrate Following a procedure similar to that described in Example 1, the desired compound was prepared from 7 g of ethyl 2-(3-o-fluorophenylthioureido)thiazol-4-ylglyoxylate, 3.8g of rhodanine-3-acetic acid, 2 g of ammonium chloride, ml of 28% v/v aqueous ammonia and 100 ml of ethanol. The resulting product was a yellow powder having the following physical properties.

Melting point: 187° to 200 °C. (with decomposition).

Nuclear Magnetic Resonance Spectrum (hexadeuterated dimethyl sulfoxide) δ ppm: 1.34 (3H, triplet, J=7 Hz), 4.42 (2H, quartet, J=7 Hz), 4.69 (2H, broad singlet), 7.2-7.37 (3H, multiplet), 7.67 (1H, singlet), 7.87 (1H, broad triplet, J=8 Hz), 0.05 (1H, broad singlet, disappeared on adding deuterium oxide), 12.1-12.5 (1H, broad, disappeared on adding deuterium oxide).

EXAMPLE 64

5-{1-Ethoxycarbonyl-1-[2-(3-p-fluorophenylthioureido)-thiazol-4-yl]methylene}rhodanine-3-acetic acid Following a procedure similar to that described in Example 1, the desired compound was prepared from 550 mg of ethyl 2-(3-p-fluorophenylthioureido)thiazol-4-ylglyoxylate, 29 mg of rhodanine-3-acetic acid, 150 mg of ammonium chloride, 0.15 ml of 28% v/v aqueous ammonia and 10 ml of ethanol. The resulting product was in the form of yellow acicular crystals having the following physical properties.

Melting Point: 220° to 225 ° C. (with decomposition).

Nuclear Magnetic Resonance Spectrum (hexadeuterated dimethyl sulfoxide) δ ppm: 1.34 (3H, triplet, J=7 Hz), 4.42 (2H, quartet. J=7 Hz), 4.70 (2H, broad singlet), 7.25 (2H, triplet, J=9 Hz), 7.61 (2H, doublet of doublets, J=5 and 9 Hz), 7.66 (1H, singlet), 10.29 (1H, broad singlet, disappeared on adding deuterium oxide), 11.9–12.2 (1H, broad, disappeared on adding deuterium oxide), 13.15–13.7 (1H, broad, disappeared on adding deuterium oxide).

EXAMPLE 65

5-(2-Anilinothiazol-4-ylmethylene)rhodanine-3-acetic acid

Following a procedure similar to that described in Example 24, the desired compound was prepared from 440 mg of 2-anilinothiazole-4-carbaldehyde, 412 mg of rhodanine-3-acetic acid, 0.5 ml of piperidine and 10 ml of ethanol. The resulting product was a yellowish-brown powder having the following physical properties.

Melting Point: 242° to 246 ° C.

Nuclear Magnetic Resonance Spectrum (hexadeuterated dimethyl sulfoxide) δ ppm: 4.87 (2H, broad singlet). 7.10 (1H, triplet, J=8 Hz). 7.42 (2H, triplet, J=8 Hz), 7.59 (1H, singlet), 7.63 (1H, singlet), 7.78 (2H, doublet, J=8 Hz), 9.63 (1H, broad singlet).

EXAMPLE 66

Ethyl 5-(2-anilinothiazol-4-ylmethylene)rhodanine-3-acetate

Following a procedure similar to that described in Example 30, the desired compound was prepared from 1 g of 5-(2-anilinothiazol-4-ylmethylene)rhodanine-3-acetic acid, 2 g of ethanol and 10 ml of a 4N dioxane solution of hydrogen chloride. The resulting product was a yellow powder having the following physical properties.

Melting Point: 212° to 215 ° C.

Nuclear Magnetic Resonance Spectrum (hexadeuterated dimeIhyl sulfoxide) δ ppm: 1.21 (3H, triplet, J=7 Hz). 4.17 (2H, quartet, J=7 Hz), 4.81 (2H, singlet), 7.05 (1H, triplet, J=8 Hz), 7.37 (2H, triplet, J=8 Hz), 7.68 (1H, singlet). 7.71 (2H, doublet, J=8 Hz), 7.80 (1H, singlet), 10.54 (1H, singlet, disappeared on adding deuterium oxide).

EXAMPLE 67

1-lsopropoxycarbonyloxyethyl 5-(2-anilinothiazol-4-yl-methylene)rhodanine-3-acetate Following a procedure similar to that described in Example 34, the desired compound was prepared from 1 g of 5-(2-anilinothiazol-4-ylmethylene)rhodanine-3-acetic acid, 0.5 g of 1.8-diazabicyclo[5.4.0]undec-7-ene, 4.5 g of 1-iodoethyl isopropyl carbonate and 16 ml of dimethylacetamide. The resulting product was a yellowish-green powder having the following physical properties.

Melting Point: 166° to 169° C.

Nuclear Magnetic Resonance Spectrum (hexadeuterated dimethyl sulfoxide) δ ppm: 1.24 (6H, doublet, J=6 Hz), 1.46 (3H, doublet, J=5 Hz), 4.79 (1H, septet, J=6 Hz), 4.8–4.95 (2H, not defined), 6.67 (1H, quartet, J=5 Hz), 7.05 (1H, triplet, J=8 Hz). 7.36 (2H, triplet, J=8 Hz), 7.68 (1H, singlet), 7.71 (2H, doublet. J=8 Hz), 7.81 (1H, singlet), 10.55 (1H, broad singlet, disappeared on adding deuterium oxide).

EXAMPLE 68

Sodium 5-(2-anilinothiazol-4-ylmethylene)rhodanine-3-acetate

Following a procedure similar to that described in Example 35, the desired compound was prepared from 1 g of 5-(2-anilinothiazol-4-ylmethylene)rhodanine-3-acetic acid, 280 mg of sodium methoxide and 20 ml of ethanol. The resulting product was a yellow powder having the following physical properties.

Melting Point: 280° to 295 ° C. (with decomposition).

Nuclear Magnetic Resonance Spectrum (hexadeuterated dimethyl sulfoxide) δ ppm: 4.31 (2H, singlet), 7.03 (1H, triplet, J=8 Hz). 7.35 (2H, triplet, J=8 Hz), 7.51 (1H, singlet). 7.69 (1H, singlet), 7.74 (2H, doublet, J=8 Hz), 10.70 (1H, broad singlet, disappeared on adding deuterium oxide).

EXAMPLE 69

5-[2-(o-toluidino)thiazol-4-ylmethylene]-rhodanine-3-acetic acid

Following a procedure similar to that described in Example 1, the desired compound was prepared from 1.12 g of 2-(o-toluidino)thiazole-4-carbaldehyde, 0.87 g of rhodanine-3-acetic acid, 0.5 g of ammonium chloride, 0.5 ml of 28% v/v aqueous ammonia and 15 ml of ethanol. The resulting product was an orange powder having the following physical properties.

Melting Point: 247° to 249.5 ° C. (with decomposition).

Nuclear Magnetic Resonance Spectrum (hexadeuterated dimethyl sulfoxide) δ ppm: 2.30 (3H, singlet), 4.70 (2H, singlet), 7.08 (1H, broad triplet, J=8 Hz). 7.24 (2H, broad triplet, J=8 Hz), 7.62 (1H, singlet), 7.72 (1H, singlet), 7.95 (1H, broad doublet, J=8 Hz). 9.67 (1H, broad singlet), 3.1 ∝ 13.6 (1H, broad).

EXAMPLE 70

5-[(2E)-3-(2-Anilinothiazol-4-yl)allylidene]-rhodanine-3-acetic acid

Following a procedure similar to that described in Example 1, the desired compound was prepared from 0.4 g of (2E)-3-(2-anilinothiazol-4-yl)acrylaldehyde, 0.29 g of rhodanine-3-acetic acid, 0.22 g of ammonium chloride, 0.2 ml of 28% v/v aqueous ammonia and 10 ml of ethanol. The resulting product was a reddish-brown powder having the following physical properties.

Melting point: 244° to 248 ° C. (with decomposition).

Nuclear Magnetic Resonance Spectrum (hexadeuterated dimethyl sulfoxide) δ ppm: 4.70 (2H, broad singlet), 6.91 (1H, doublet of doublets, J=15 and 12 Hz), 7.00 (1H, triplet, J=7 Hz), 7.28 (1H, doublet, J=15 Hz), 7.37 (1H, singlet), 7.37 (2H, triplet, J=7 Hz), 7.64 (1H, doublet, J=12 Hz), 7.67 (2H, doublet, J=7 Hz), 10.38 (1H, broad singlet, disappeared on adding deuterium oxide).

EXAMPLE 71

5-(2-Diphenylmethylaminothiazol-4-ylmethylene)-rhodanine-3-acetic acid

Following a procedure similar to that described in Example 1, the desired compound was prepared from 1.95 g of 2-diphenylmethylaminothiazole-4-carbaldehyde. 1.32 g of rhodanine-3-acetic acid, 0.4 g of ammonium chloride, 0.4 ml of 28% v/v aqueous ammonia and 20 ml of ethanol. The resulting product was a reddish-brown powder having the following physical properties.

Melting Point: 227° to 230° C. (with decomposition).

Nuclear Magnetic Resonance Spectrum (hexadeuterated dimethyl sulfoxide) δ ppm: 4.66 (2H, singlet), 6.13 (1H, doublet, J=7 Hz, converted to 6.13 (1H, singlet) on adding deuterium oxide), 7.2–7.4 (10H, multiplet), 7.48 (1H, singlet), 7.54 (1H, singlet), 8.99 (1H, doublet, J=7 Hz, disappeared on adding deuterium oxide), 13.0–13.7 (1H, broad, disappeared on adding deuterium oxide).

EXAMPLE 72

Ethyl 5-(2-diphenylmethylaminothiazol-4-ylmethylene)-rhodanine-3-acetate

Following a procedure similar to that described in Example 30, the desired compound was prepared from 0.6 g of 5-(2-diphenylmethylaminothiazol-4-ylmethylene)rhodanine–acetic acid, 7.7 g of ethanol and 15 ml of a 4N dioxane solution of hydrogen chloride. The resulting product was a greenish-yellow powder having the following physical properties.

Melting Point: 196° to 199 ° C. (with decomposition).

Nuclear Magnetic Resonance Spectrum (hexadeuterated dimethyl sulfoxide) δ ppm: 1.19 (3H, triplet, J=7 Hz), 4.15 (2H, quartet, J=7 Hz), 4.76 (2H, singlet), 6.13 (1H, doublet. J=7 Hz, converted to 6.12 (1H, singlet) on adding deuterium oxide), 7.22–7.43 (10H, multiplet), 7.50 (1H, singlet), 7.55 (1H, singlet), 8.99 (1H, doublet, J=7 Hz, disappeared on adding deuterium oxide).

EXAMPLE 73

Sodium 5-(2-diphenylmethylaminothiazol-4-ylmethylene)rhodanine-3-acetate monohydrate Following a procedure similar to that described in Example 35, the desired compound was prepared from 200 mg of 5-(2-diphenylmethylaminothiazol-4-ylmethylene)rhodanine-3-acetic acid, 24.5 mg of sodium methoxide and 6 ml of ethanol. The resulting product was a yellow powder having the following physical properties.

Melting Point: 181° to 194° C. (with decomposition).

Nuclear Magnetic Resonance Spectrum (hexadeuterated dimethyl sulfoxide) δ ppm: 4.20 (2H, singlet), 6.15 (1H, doublet, J=8 Hz), 7.22–7.45 (12H, multiplet), 8.95 (1H, doublet, J=8 Hz).

EXAMPLE 74

-{1-2-Bis(p-fluorophenyl)methylaminothiazol-4-yl]-1-ethoxycarbonylmethylene}rhodanine-3-acetic acid Following a procedure similar to that described in Example 1, the desired compound was prepared from 342 mg of ethyl 2-bis(p-fluorophenyl)methyaminothiazol-4-glglyoxylate, 164 mg of rhodanine-3-acetic acid, 0.11 g of ammonium chloride, 0.2 ml of 28% v/v aqueous ammonia and 2 ml of ethanol, as red prismatic crystals. The product had the following physical properties.

Melting point: 245° to 247° C.

Nuclear Magnetic Resonance Spectrum (hexadeuterated dimethyl sulfoxide) δ ppm: 1.29 (3H, triplet, J=7 Hz), 4.35 (2H, quartet, J=7 Hz), 4.63 (2H, singlet), 6.08 (1H, doublet, J=6 Hz), 7.14–7.23 (4H, multiplet), 7.26 (1H, singlet), 7.37–7.45 (4H, multiplet), 9.03 (1H, doublet, J=6 Hz).

EXAMPLE 75

5-[1-Ethoxycarbonyl-1-(2-phthalimidothiazol-4-Y1)methylene]rhodanine-3-acetic acid hemihydrate 0.7 g of phthaloyl dichloride was added dropwise under ice-cooling to a solution of 1.19 g of 5-[1-(2-aminothiazol-4-yl)-1-ethoxycarbonylmethylene]rhodanine-3-acetic acid in 8 ml of tetrahydrofuran. The resulting mixture was stirred for 6 hours under ice-cooling and then heated at 60° C. for 4 hours. The crystals which precipitated out after cooling were collected by filtration and recrystallized from ethanol. The resulting product was a yellow powder having the following physical properties.

Melting point: circa 300° C. (with decomposition).

Nuclear Magnetic Resonance Spectrum (hexadeuterated dimethyl sulfoxide) δ ppm: 1.36 (3H, triplet, J=7 Hz), 4.46 (2H, quartet, J=7 Hz), 4.71 (2H, broad singlet). 7.98 (2H, doublet of doublets, J=5 and 3 Hz), 8.05–8.15 (2H, not defined), 8.10 (1H, singlet), 12.9–13.8 (1H, broad, disappeared on adding deuterium oxide).

EXAMPLE 76

5-[2-(p-Fluoroanilino)thiazol-4-ylmethylene]rhodanine-3-acetic acid

The reaction described in Example 1 was repeated, but using 1 g of 2-(p-fluoroanilino)thiazole-4-carbaldehyde, 0.85 g of rhodanine-3-acetic acid, 0.5 g of ammonium chloride, 0.5 ml of 28% v/v aqueous ammonia, and 10 ml of ethanol, giving the title compound as an orange powder.

Melting point: 263.5° to 226° C. (with decomposition).

Nuclear Magnetic Resonance Spectrum (hexadeuterated dimethyl sulfoxide) δ ppm: 4.71 (2H, singlet), 7.19 (2H, triplet, J=9 Hz). 7.65 (1H, singlet), 7.71 (2H, doublet of doublets, J=9 and 5 Hz), 7.78 (1H, singlet), 10.54 (1H, broad singlet, disappeared on adding deuterium oxide), 13.0–13.8 (1H, broad, disappeared on adding deuterium oxide).

EXAMPLE 77

5-[2-(p-Anisidino)thiazol-4-ylmethylene]rhodanine-3-acetic acid

The reaction described in Example 1 was repeated, but using 1 g of 2-(p-anisidino)thiazole-4-carbaldehyde, 0.8 g of rhodanine-3-acetic acid 0.5 g of ammonium chloride, 0.5 ml of 28% v/v aqueous ammonia, and 10 ml of ethanol, giving the title compound as an orange powder.

Melting Point: 197° to 202° C.

Nuclear Magnetic Resonance Spectrum (hexadeuterated dimethyl sulfoxide) δ ppm: 3.76 (3H, singlet), 4.72 (2H, singlet), 6.93 (2H, doublet, J=9 Hz), 7.60 (2H, doublet, J=9 Hz), 7.63 (1H, singlet), 7.72 (1H, singlet), 10.32 (1H, broad singlet, disappeared on adding deuterium oxide), 13.1–13.7 (1H, broad, disappeared on adding deuterium oxide).

EXAMPLE 78

5-[2-(m-trifluoromethylanilino)thiazol-4-ylmethylene]rhodanine-3-acetic acid

The reaction described in Example 1 was repeated, but using 1 g of 2-(m-trifluoromethylanilino)thiazole-4-carbaldehyde, 0.7 g of rhodanine-3-acetic acid, 0.5 g of ammonium chloride, 0.5 ml of 28% v/v aqueous ammonia, and 10 ml of ethanol, giving the title compound as yellowish-orange prisms.

Melting point: 249° to 252° C. (with decomposition).
Nuclear Magnetic Resonance Spectrum (hexadeuterated dimethyl sulfoxide) δ ppm: 4.72 (2H, singlet), 7.37 (1H, broad doublet, J=8 Hz), 7.58 (1H, broad triplet, J=8 Hz). 7.65 (1H, broad doublet, J=8 Hz). 7.69 (1H, singlet), 7.88 (1H, singlet), 8.43 (1H, broad singlet), 10.90 (1H, broad singlet, disappeared on adding deuterium oxide), 13.2–13.6 (1H, broad, disappeared on adding deuterium oxide.

EXAMPLE 79

5-(2-Ethylaminothiazol-4-ylmethylene)rhodanine-3-acetic acid

The reaction described in Example 1 was repeated, but using 1.27 g of 2-ethylaminothiazole-4-carbaldehyde, 1.3 g of rhodanine-3-acetic acid, 1 g of ammonium chloride, 1 ml of 28% v/v aqueous ammonia and 30 ml of ethanol, giving 1.9 g of the title compound as yellow needles.

Melting Point: 248° to 250° C. (with decomposition).
Nuclear Magnetic Resonance Spectrum (hexadeuterated dimethyl sulfoxide) δ ppm: 1.23 (3H, triplet, J=7 Hz), 3.3–3.45 (2H, multiplet), 4.70 (2H, singlet), 7.52 (1H, singlet). 7.54 (1H, singlet), 8.05 (1H, broad triplet, J=5 Hz), 13.33 (1H, broad singlet).

EXAMPLE 80

5-(2-Allylaminothiazol-4-ylmethylene)rhodanine-3-acetic acid

The reaction described in Example 1 was repeated, but using 3.0 g of 2-allylaminothiazole-4-carbaldehyde, 2.8 g of rhodanine-3-acetic acid, 2.1 g of ammonium chloride, 2.1 ml of 28% v/v aqueous ammonia and 70 ml of ethanol giving 3.3 g of the title compound as brown needles.

Melting point: 234° to 236° C. (with decomposition).
Nuclear Magnetic Resonance Spectrum (hexadeuterated dimethyl sulfoxide) δ ppm: 3.98–4.03 (2H, multiplet), 4.70 (2H, singlet), 5.16 (1H, doublet of doublets of doublets, J=10, 3 and 1.5 Hz), 5.29 (1H, doublet of doublets of doublets, J=17, 3, and 1.5 Hz), 5.90–6.05 (1H, multiplet), 7.54 (2H, singlet), 8.23 (1H, broad triplet, J=5 Hz), 13.1–13.6 (1H, broad).

EXAMPLE 81

5-(2-Cyclohexylaminothiazol-4-ylmethylene)rhodanine-3-acetic acid

The reaction described in Example 1 was repeated, but using 3.0 g of 2-cyclohexylaminothiazole-4-carbaldehyde, 2.27 g of rhodanine-3-acetic acid, 1.7 g of ammonium chloride, 1.7 ml of 28% v/v aqueous ammonia and 60 ml of ethanol giving the title compound as yellowish-brown needles.

Melting Point: 220° to 222° C. (with decomposition).
Nuclear Magnetic Resonance Spectrum (hexadeuterated dimethyl sulfoxide) δ ppm: 1.15–1.5 (5H, multiplet), 1.55–1.85 (3H, multiplet), 2.0–2.1 (2H, multiplet), 3.55–3.7 (1H, multiplet), 4.70 (2H, singlet), 7.49 (1H, singlet), 7.52 (1H, singlet), 8.02 (1H, doublet, J=7 Hz, disappeared on adding deuterium oxide), 13.2–13.45 (1H, broad disappeared on adding deuterium oxide).

EXAMPLE 82

5-(2-Diphenylaminothiazol-4-ylmethylene)rhodanine-3-acetic acid

The reaction described in Example 1 was repeated, but using 3 g of 2-diphenylaminothiazole-4-carbaldehyde, 1.7 g of rhodanine-3-acetic acid, 1.3 g of ammonium chloride, 1.3 ml of 28% v/v aqueous ammonia and 60 ml of ethanol, giving the title compound as orange needles.

Melting point: circa 305° to 310° C. (with decomposition).
Nuclear Magnetic Resonance Spectrum (hexadeuterated dimethyl sulfoxide) δ ppm: 4.69 (2H, singlet), 7.3–7.48 (2H, multiplet), 7.49 (4H, broad singlet), 7.51 (4H, broad singlet), 7.64 (1H, singlet), 7.75 (1H, singlet), 13.1–13.5 (1H, broad).

EXAMPLE 83

5(2-Morpholinothiazol-4-ylmethylene)rhodanine-3-acetic acid

The reaction described in Example 1 was repeated, but using 1.65 g of 2-morpholinothiazole-4-carbaldehyde, 1.3 g of rhodanine-3-acetic acid, 1g of ammonium chloride, 1 ml of 28% v/v aqueous ammonia and 35 ml of ethanol, giving the title compound as yellow needles.

Melting point: 287° to 290° C. (with decomposition).
Nuclear Magnetic Resonance Spectrum (hexadeuterated dimethyl sulfoxide) δ ppm: 3.50 (4H, broad triplet, J=5 Hz), 3.76 (4H, broad triplet, J=5 Hz), 4.70 (2H, singlet), 7.61 (1H, singlet), 7.72 (1H, singlet), 13.1–13.6 (1H, broad).

EXAMPLE 84

5-(2-piperidinothiazol-4-ylmethylene)rhodanine-3-acetic acid

The reaction described in Example 1 was repeated. but using 1.8 g of 2-piperidinothiazole-4-carbaldehyde, 1.4 g of rhodanine-3-acetic acid, 1.0 g of ammonium chloride, 1 ml of 28% v/v aqueous ammonia and 40 ml of ethanol, giving the title compound as yellow needles.

Melting Point: 277° to 280° C. (with decomposition).
Nuclear Magnetic Resonance Spectrum (hexadeuterated dimethyl sulfoxide) δ ppm: 1.64 (6H, broad singlet), 3.52 (4H, broad singlet), 4.70 (2H, singlet), 7.57 (1H, singlet), 7.65 (1H, singlet), 13.0–13.7 (1H, broad).

EXAMPLE 85

5-[2-(Thiomorpholin-4-yl)thiazol-4-ylmethylene]rhodanine-3-acetic acid

The reaction described in Example 1 was repeated, but using 0.85 g of 2-(thiomorpholin-4-yl)thiazole-4-carbaldehyde, 0.76 g of rhodanine-3-acetic acid, 0.4 g of ammonium chloride, 0.4 ml of 28% v/v aqueous ammonia and 30 ml of ethanol, giving the title compound as yellow crystals.

Melting Point: 267 to 270° C.(with decomposition).
Nuclear Magnetic Resonance Spectrum (hexadeuterated dimethyl sulfoxide) δ ppm: 2.7–2.8 (4H, multiplet), 3.8–3.9 (4H. multiplet), 4.71 (2H, singlet), 7.59 (1H, singlet), 7.70 (1H, singlet), 3.0–13.6 (1H, broad).

EXAMPLE 86

5-[2-(3-Benzoylthioureido)thiazol-4-ylmethylene]rhodanine-3-acetic acid 2.6 g of benzoyl isothiocyanate were added dropwise, at room temperature, to a solution of 4 g of 5-(2-aminothiazol-4-ylmethylene)rhodanine-3-acetic acid in 70 ml of dimethylformamide. The reaction mixture was stirred at room temperature for 6 hours. then ethyl acetate was added and precipitated solids were filtered off. The ethyl acetate solution was washed with water and concentrated under reduced pressure, and the crystalline solid thus obtained was separated by filtration and recrystallized from acetic acid, giving the title compound as a yellow powder.
Melting Point: 248° to 250° C. (with decomposition).
Nuclear Magnetic Resonance Spectrum (hexadeuterated dimethyl sulfoxide) δ ppm: 4.73 (2H, singlet), 7.57 (2H, broad triplet, J=8 Hz), 7.71 (2H, broad triplet, J=8 Hz), 7.84 (1H, singlet), 8.06 (2H, broad doublet, J=8 Hz). 8.09 (1H, singlet), 12.27 (1H, singlet, disappeared on adding deuterium oxide), 13.0–13.7 (1H, broad, disappeared on adding deuterium oxide), 14.30 (1H, singlet, disappeared on adding deuterium oxide),

EXAMPLE 87

5-[2-(4-Methyl-1-piperazinyl)thiazol-4-ylmethylene]rhodanine-3-acetic acid

The reaction described in Example 1 was repeated, but using 1.8 g of 2-(4-methyl-1-piperazinyl)thiazole-4-carbaldehyde, 1.2 g of rhodanine-3-acetic acid, 0.9 g of ammonium chloride, 0.9 ml of 28% v/v aqueous ammonia, and 40 ml of ethanol, giving the title compound as dark yellow needles.
Melting Point: over 300° C.
Nuclear Magnetic Resonance Spectrum (CF$_3$COOD) δ ppm: 3.24 (3H, singlet), 3.63 (2H, broad doublet of triplets, J=13 and 3 Hz), 4.04 (2H, broad doublet, J=13 Hz), 4.22 (2H, broad triplet, J=13 Hz), 4.39 (2H, broad doublet, J=13 Hz), 5.11 (2H, singlet), 7.60 (1H, singlet).

EXAMPLE 88

-(2-Octylaminothiazol-4-ylmethylene)rhodanine-3-acetic acid ⅓ ethanol adduct

The reaction described in Example 1 was repeated, but using 1.1 g of 2-octylaminothiazole-4-carbaldehyde, 0.66 g of rhodanine-3-acetic acid. 0.5 g of ammonium chloride, 0.5 ml of 28% v/v aqueous ammonia and 30 ml of ethanol, giving the title compound as pale brown needles.
Melting Point: 147° to 149° C.
Nuclear Magnetic Resonance Spectrum (hexadeuterated dimethyl sulfoxide) δ ppm: 0.85 (3H, broad triplet, J=7 Hz), 1.06 (1H, triplet, J=7 Hz), 1.15–1.45 (10 H, multiplet), 1.55–1.7 (2H, multiplet), 3.2–3.5 (2.67H, not defined), 4.25–4.4 (0.33H, multiplet), 4.70 (2H, singlet), 7.50 (1H, singlet). 7.53 (1H, singlet), 8.06 (1H, triplet, J=5 Hz), 3.0–13.6 (1H, broad).

EXAMPLE 89

5-(2-Isopropylaminothiazol-4-ylmethylene)rhodanine-3-acetic acid

The reaction described in Example 1 was repeated, but using 2.7 g of 2-isopropylaminothiazole-4-carbaldehyde, 2.3 g of rhodanine-3-acetic acid, 1.7 g of ammonium chloride, 1.7 ml of 28% v/v aqueous ammonia and 50 ml of ethanol, giving the title compound as dark red needles.
Melting Point: 227° to 229° C. (with decomposition).
Nuclear Magnetic Resonance Spectrum (hexadeuterated dimethyl sulfoxide) δ ppm: 1.25 (6H, doublet, J=7 Hz), 3.85–4.0 (1H, multiplet), 4.70 (2H, singlet), 7.51 (1H, singlet), 7.53 (1H, singlet), 7.98 (1H, doublet, J=7 Hz), 3.0–13.8 (1H, broad).

EXAMPLE 90

5-(2-Benzylaminothiazol-4-ylmethylene)rhodanine-3-acetic acid

The reaction described in Example 1 was repeated, but using 0.58 g of 2-benzylaminothiazol-4-carbaldehyde, 0.5 g of rhodanine-3-acetic acid 0.3 g of ammonium chloride. 0.3 ml of 28% v/v aqueous ammonia and 40 ml of ethanol, giving the title compound as yellow needles.
Melting point: 207° to 210° C.
Nuclear Magnetic Resonance Spectrum (hexadeuterated dimethyl sulfoxide) δ ppm: 4.58 (2H, doublet, J=6 Hz), 4.69 (2H, singlet), 7.2–7.45 (5H, multiplet). 7.53 (2H, singlet), 8.57 (1H, triplet, J=6 Hz, disappeared on adding deuterium oxide), 13.0–13.6 (1H, broad, disappeared on adding deuterium oxide),

EXAMPLE 91

5-{1-[2-(3-Benzoylthioureido)thiazol-4-yl]-1-carboxymethylene}rhodanine-3-acetic acid monohydrate The reaction described in Example 1 was repeated, but using 1.0 g of crude sodium 2-(3-benzoylthioureido)thiazol-4-ylglyoxylate. 0.75 g of rhodanine-3-acetic acid, 0.2 g of ammonium chloride, 0.5 ml of 28% v/v aqueous ammonia and 20 ml of ethanol, giving the title compound as a yellow powder.
Melting Point: 255° to 265° C.
Nuclear Magnetic Resonance Spectrum (hexadeuterated dimethyl sulfoxide) δ ppm: 4.71 (2H, singlet), 7.58 (2H, broad triplet, J=8 Hz), 7.71 (1H, broad triplet, J=8 Hz), 7.77 (1H, singlet), 8.06 (2H, broad doublet, J=8 Hz), 12.3 (1H, broad singlet, disappeared on adding deuterium oxide), 13.0–13.9 (1H, broad, disappeared on adding deuterium oxide), 13.9–14.7 (2H, broad, disappeared on adding deuterium oxide).

EXAMPLE 92

5-(2-Cyclopropylaminothiazol-4-ylmethylene)rhodanine-3-acetic acid

The reaction described in Example 1 was repeated, but using 0.53 g of 2-cyclopropylaminothiazole-4-carbaldehyde. 0.46 g of rhodanine-3-acetic acid, 0.3 g of ammonium chloride, 0.3 ml of 28% v/v aqueous ammonia and 20 ml of ethanol, giving the title compound as an orange powder.
Melting Point: 255° to 257° C.
Nuclear Magnetic Resonance Spectrum (hexadeuterated dimethyl sulfoxide) δ ppm: 0.54–0.6 (2H, multiplet). 0.74–0.81 (2H, multiplet), 2.6–2.7 (1H, multiplet). 4.69 (2H, singlet), 7.56 (1H, singlet), 7.58 (1H, singlet), 8.38 (1H, doublet, J=1 Hz), 13.1–13.6 (1H, broad).

PREPARATION 1

Ethyl 2-(3-phenylureido)thiazol-4-ylglyoxylate 10 g of ethyl 2-aminothiazol-4-ylglyoxylate were dissolved in 100 ml of dimethylformamide, and 7.14 g of phenyl isocyanate were added dropwise to the resulting solution under ice-cooling. The mixture was left to stand overnight, and the dimethylformamide was then evaporated off under reduced pressure. The crystals thus obtained were washed with water, dried and recrystallized from ethyl acetate, giving the desired compound as yellow crystals.

Melting Point: 217° to 220° C.

Nuclear Magnetic Resonance Spectrum (hexadeuterated dimethyl sulfoxide) δ ppm: 1.34 (3H, triplet, J=7 Hz), 4.38 (2H, quartet, J=7 Hz), 6.95–7.6 (5H, multiplet), 8.41 (1H, singlet), 8.93 (1H, broad singlet), 10.8–11.3 (1H, broad singlet).

PREPARATION 2

Ethyl 2-(3-o-methoxyphenylureido)thiazol-4-ylglyoxylate

Following a procedure similar to that described in preparation 1, the desired compound was prepared from 5 g of ethyl 2-aminothiazol-4-ylglyoxylate, 4.5 g of o-methoxyphenyl isocyanate and 40 ml of dimethylformamide. The resulting product was a yellow powder having the following physical properties.

Melting point: 223° to 227° C.

Nuclear Magnetic Resonance Spectrum (hexadeuterated dimethyl sulfoxide) δ ppm: 1.34 (3H, triplet, J=7 Hz), 3.88 (3H, singlet), 4.38 (2H, quartet, J=7 Hz), 6.9–7.0 (1H, multiplet), 7.0–7.1 (2H, multiplet), 8.05–8.15 (1H, multiplet), 8.39 (1H, singlet), 8.65 (1H, broad singlet, disappeared on adding deuterium oxide), 11.46 (1H, broad subject, disappeared on adding deuterium oxide).

PREPARATION 3

Ethyl 2-(3-m-methoxyphenylureido)thiazol-4-ylglyoxylate

Following a procedure similar to that described in Preparation 1, the desired compound was prepared from 5 g of ethyl 2-aminothiazol-4-ylglyoxylate, 4.5 g of m-methoxyphenyl isocyanate and 40 ml of dimethylformamide, as yellow crystals having the following physical properties.

Melting Point: 182° to 185° C.

Nuclear Magnetic Resonance Spectrum (hexadeuterated dimethyl sulfoxide) δ ppm: 1.33 (3H, triplet, J=7 Hz), 3.75 (3H, singlet), 4.37 (2H, quartet, J=7 Hz), 6.64 (1H, doublet of doublets, J=2 and 8 Hz), 6.95–7.0 (1H, multiplet), 7.16 (1H, triplet, J=2 Hz), 7.23 (1H, triplet, J=8 Hz), 8.41 (1H, singlet), 8.90 (1H, broad singlet, disappeared on adding deuterium oxide), 10.99 (1H, broad singlet, disappeared on adding deuterium oxide).

PREPARATION 4

Ethyl 2-(3-p-methoxyphenylureido)thiazol-4-ylglyoxylate

Following the procedures in preparation 1, the desired compound was prepared using 10 g of ethyl 2-aminothiazol-4-ylglyoxylate, 9 g of p-methoxyphenyl isocyanate and 80 ml of dimethylformamide as yellow powders. The product has the following physical properties.

Melting Point: 193° to 196° C.

Nuclear Magnetic Resonance Spectrum (hexadeuterated dimethyl sulfoxide) δ ppm: 1.33 (3H, triplet, J=7 Hz), 3.73 (3H, singlet), 4.37 (2H, quartet, J=7 Hz), 6.90 (2H, doublet, J=9 Hz), 7.38 (2H, doublet, J=9 Hz), 8.39 (1H, singlet), 8.72 (1H, broad singlet, disappeared on adding deuterium oxide), 10.96 (1H, broad singlet, disappeared on adding deuterium oxide).

PREPARATION 5

Ethyl 2-(3-p-fluorophenylureido)thiazol-4-ylglyoxylate

Following a procedure similar to that described in Preparation 1, the desired compound was prepared from 5 g of ethyl 2-aminothiazol-4-ylgyoxylate, 5.1 g of p-fluorophenyl isocyanate and 30 ml of dimethylformamide. The resulting product was a yellow powder having the following physical properties.

Melting Point: 220° to 223° C.

Nuclear Magnetic Resonance Spectrum (hexadeuterated dimethyl sulfoxide) δ ppm: 1.34 (3H, triplet, J=7 Hz), 4.39 (2H, quartet, J=7 Hz), 7.17 (2H, triplet, J=9 Hz). 7.53 (2H, doublet of doublets, J=5 and 9 Hz), 8.43 (1H, singlet), 8.96 (1H, broad singlet), 11.09 (1H, broad singlet).

PREPARATION 6

Ethyl 2-(3-p-chlorophenylureido)thiazol-4-ylglyoxylate

Following a procedure similar to that described in Preparation 1, the desired compound was prepared from 10 g of ethyl 2-aminothiazol-4-ylglyoxylate, 8.6 g of p-chlorophenyl isocyanate and 100 ml of dimethylformamide. The resulting product was a yellow powder having the following physical properties.

Melting Point: 230° to 234° C.

Nuclear Magnetic Resonance Spectrum (hexadeuterated dimethylsulfoxide) δ ppm: 1.34 (3H, triplet, J=7 Hz), 4.39 (2H, quartet, J=7 Hz), 7.38 (2H, doublet, J=9 Hz), 7.55 (2H, doublet, J=9 Hz), 8.43 (1H, singlet), 9.06 (1H, broad singlet), 11.14 (1H, broad singlet).

PREPARATION 7

Ethyl 2-(3-p-bromophenylureido)thiazol-4-ylglyoxylate

Following a procedure similar to that described in Preparation 1, the desired compound was prepared from 10 g of ethyl 2-aminothiazol-4-ylglyoxylate, 8.7 g of p-bromophenyl isocyanate and 80 ml of dimethylformamide, as yellow crystals having the following physical properties.

Melting Point: 235° to 241° C.

Nuclear Magnetic Resonance Spectrum (hexadeuterated dimethyl sulfoxide) δ ppm: 1.33 (3H, triplet, J=7 Hz), 4.37 (2H, quartet, J=7 Hz) 7.44–7.53 (4H, multiplet), 8.42 (1H, singlet), 9.05 (1H, broad singlet), 11.10 (1H, broad singlet).

PREPARATION 8

Ethyl 2-[3-(3,4-dichlorophenyl)ureido]thiazol-4-ylglyoxylate

Following a procedure similar to that described in Preparation 1, the desired compound was prepared from 10 g of ethyl 2-aminothiazol-4-ylglyoxylate, 10 g of 3,4-dichlorophenyl isocyanate and 100 ml of dimethylformamide. The resulting product was a pale yellow powder having the following physical properties.

Melting Point: circa 250° C. (with decomposition).

Nuclear Magnetic Resonance Spectrum (hexadeuterated dimethyl sulfoxide) δ ppm: 1.34 (3H, triplet, J=7 Hz), 4.39 (2H, quartet, J=7 Hz), 7.43 (1H, doublet of doublets, J=2 and 9 Hz), 7.59 (1H, doublet, J=9 Hz), 7.89 (1H, doublet, J=2 Hz), 8.46 (1H, singlet), 9.22 (1H, broad singlet), 11.29 (1H, broad singlet).

PREPARATION 9

Ethyl 2-[3-(1-naphthyl)ureido]thiazol-4-ylglyoxylate

Following a procedure similar to that described in preparation 1, the desired compound was prepared from 10 g of ethyl 2-aminothiazol-4-ylglyoxylate, 10.1 g of 1-naphthyl isocyanate and 100 ml of dimethylformamide. The resulting product was a grayish-white powder having the following physical properties.

Melting Point: 209° to 211° C.

Nuclear Magnetic Resonance Spectrum (heptadeuterated dimethylformamide) δ ppm: 1.37 (3H, triplet, J=7 Hz), 4.44 (2H, quartet, J=7 Hz), 7.45–8.4 (7H, multiplet), 8.47 (1H, singlet), 9.44 (1H, broad singlet), 10.8–11.7 (1H, broad singlet).

PREPARATION 10

Ethyl 2-(3-p-toluenesulfonylureido)thiazol-4-ylglyoxylate

Following a procedure similar to that described in Preparation 1, the desired compound was prepared from 6 g of ethyl 2-aminothiazole-4-ylglyoxylate, 6 g of p-toluenesulfonyl isocyanate and 40 ml of dimethylformamide. The resulting product was a pale yellow powder having the following physical properties.

Melting Point: 200° to 207° C. (with decomposition).

Nuclear Magnetic Resonance Spectrum (hexadeuterated dimethyl sulfoxide) δ ppm: 1.31 (3H, triplet, J=7 Hz), 2.40 (3H, singlet), 4.35 (2H, quartet, J=7 Hz), 7.44 (2H, doublet, J=8 Hz), 7.86 (2H, doublet, J=8 Hz), 8.44 (1H, singlet), 11.10–11.65 (1H, broad singlet).

PREPARATION 11

Ethyl 2-(3-phenylthioureido)thiazol-4-ylglyoxylate 5 g of ethyl 2-aminothiazol-4-ylglyoxylate were dissolved in 30 ml of hexamethylphosphoric triamide, and 5.2 g of phenyl isothiocyanate were added to the resulting solution under ice-cooling. The reaction mixture was kept stirred at an external temperature of 60° C. for 8 hours, then acidified with dilute hydrochloric acid and extracted with ethyl acetate. The extract was dried over anhydrous magnesium sulfate and then concentrated under reduced pressure. The crystals which precipitated out were collected by filtration to give the desired compound as pale yellow crystals.

Melting Point: 190° to 192° C.

Nuclear Magnetic Resonance Spectrum (hexadeuterated dimethyl sulfoxide) δ ppm: 1.33 (3H, triplet, J=7 Hz), 4.41 (2H, quartet, J=7 Hz), 7.10–7.77 (5H, multiplet), 8.40 (1H, singlet), 10.52 (1H, broad singlet), 11.8–12.6 (1H, broad).

PREPARATION 12

Ethyl 2-(3-p-chlorophenylthioureido)thiazol-4-ylglyoxylate

Following a procedure similar to that described in Preparation 1, the desired compound was prepared from 5 g of ethyl 2-aminothiazol-4-ylglyoxylate, 6.35 g of p-chlorophenyl isothiocyanate and 30 ml of hexamethylphosphoric triamide. The resulting product was a yellow powder having the following physical properties.

Melting Point: 176° to 178° C. (with decomposition).

Nuclear Magnetic Resonance Spectrum (heptadeuterated dimethylformamide) δ ppm: 1.35 (3H, triplet, J=7 Hz), 4.43 (2H, quartet, J=7 Hz), 7.45 (2H, broad doublet, J=9 Hz), 7.80 (2H, broad doublet, J=9 Hz), 8.43 (1H, singlet), 10.7–11.2 (1H, broad).

PREPARATION 13

Ethyl 2-benzamidothiazol-4-ylglyoxylate 5 g of ethyl 2-aminothiazol-4-ylglyoxylate were dissolved in 50 ml of tetrahydrofuran, and 5.55 g of benzoyl bromide were added dropwise to the resulting solution under ice-cooling. The reaction mixture was kept stirred for one hour, then water was added to it, in order to precipitate out crystals. The crystals were collected by filtration and purified by silica gel column chromatography, using as eluent a 2:1 by volume mixture of hexane and ethyl acetate. The resulting product was a white powder having the following physical properties.

Melting Point: 152° to 153° C.

Nuclear Magnetic Resonance Spectrum (hexadeuterated acetone) δ ppm: 1.40 (3H, triplet, J=7 Hz), 4.44 (2H, quartet, J=7 Hz), 7.43–7.73 (2H, multiplet), 8.10–8.36 (2H, multiplet), 8.37 (1H, singlet).

PREPARATION 14

Ethyl 2-tritylaminothiazole-4-carboxylate

A mixture comprising 5 g of triphenylchloromethane and 15 ml of dichloromethane was added dropwise at −30° C. to a mixture comprising 3.1 g of ethyl 2-aminothiazole-4-carboxylate, 25 ml of dimethylformamide and 1.8 g of triethylamine. The reaction mixture was maintained at −30° C. for 10 minutes and was then stirred at room temperature for 2 hours, after which it was poured into ice water and extracted with ethyl acetate. The extract was washed successively with 0.1N hydrochloric acid and aqueous sodium chloride solution, and then dried over anhydrous sodium sulfate. The solvent was evaporated off under reduced pressure, and the residue was purified by silica gel chromatography, using as eluent a 10:1 by volume mixture of benzene and ethyl acetate. The crystals obtained thereby were washed with n-hexane, to afford the desired compound as a white powder.

Melting point: 140° to 141° C.

PREPARATION 15

2-Tritylaminothiazole-4-methanol

A mixture comprising 2.6 g of ethyl 2-tritylaminothiazole-4-carboxylate and 10 ml of tetrahydrofuran was added dropwise under ice-cooling to a mixture comprising 0.24 g of lithium aluminum hydride and 30 ml of tetrahydrofuran, under a stream of nitrogen. After completion of the dropwise addition, the resulting mixture was stirred at room temperature for 3 hours, and then with heating under reflux for one hour. Ethyl acetate and then water were added to the reaction mixture under ice-cooling, the organic layer was separated off, and the aqueous layer was re-extracted with ethyl acetate. The combined ethyl acetate extract was washed with saturated aqueous sodium chloride solution, and then dried over anhydrous sodium sulfate. The solvent was evaporated off under reduced pressure, and the residue was purified by silica gel column chromatography, using as eluent a 1:1 by volume mixture of benzene and ethyl acetate. The product was recrystallized from a mixture of ethyl acetate, acetone and n-hexane. giving the desired compound as a pale yellow powder.

Melting point: 186° to 187° C.

PREPARATION 16

2-tritylaminothiazole-4-carbaldehyde

A mixture comprising 0.5 g of 2-tritylaminothiazole-4-methanol, 5 g of manganese dioxide and 20 ml of acetone was stirred at room temperature for 60 hours. The manganese dioxide was filtered off and the filtrate was evaporated under reduced pressure. The residue was purified by silica gel column chromatography. using as eluent a 10:1 by volume mixture of benzene and ethyl acetate, giving the desired compound as a brownish-orange powder.

Nuclear Magnetic Resonance Spectrum (hexadeuterated dimethyl sulfoxide) δ ppm: 7.19–7.36 (15H, multiplet), 7.70 (1H, broad singlet), 8.93 (1H, broad singlet, disappeared on adding deuterium oxide), 9.40 (1H, singlet).

Mass spectrum (m/e): 370 (M+)

PREPARATION 17

4-(1,2-Dihydroxyethyl)-2-(3-phenylureido)thiazole 7 ml of methanol were added dropwise, over a period of one hour, to a mixture comprising 1 g of ethyl 2-(3-phenylureido)thiazol-4-ylglyoxylate, 0.6 g of sodium borohydride and 20 ml of tetrahydrofuran kept heated under reflux. The resulting mixture was cooled to room temperature and acidified with 3N hydrochloric acid. The solvent was evaporated off under reduced pressure, and the residue was washed with water, giving the desired compound as a white powder.

Melting Point: 175° to 178° C.

PREPARATION 18

2-(3-phenylureido)thiazole-4-carbaldehyde

A solution of 0.76 g of sodium metaperiodate in 15 ml of water was added dropwise at room temperature to a mixture comprising 0.5 g of 4-(1,2-dihydroxyethyl)-2-(3-phenylureido)thiazole and 15 ml of methanol, and the mixture was stirred for 2 hours after completion of the dropwise addition. The solvent was then evaporated off under reduced pressure and the residue was washed with water, giving the desired compound as a white powder.

Melting Point: 216° to 220° C. (with decomposition).

Nuclear Magnetic Resonance Spectrum (hexadeuterated dimethyl sulfoxide) δ ppm: 6.9–7.7 (5H, multiplet), 8.26 (1H, singlet), 9.03 (1H, broad singlet), 9.83 (1H, singlet), 10.5–11.2 (1H, broad).

PREPARATION 19

Ethyl 2-(3-benzoylthioureido)thiazol-4-ylglyoxylate

The reaction described in Preparation 1 was repeated, but using 20 g of ethyl 2-aminothiazol-4-ylglyoxylate, 16.5 g of benzoyl isothiocyanate, and 100 ml of dimethylformamide, giving the title compound as a pale yellow powder.

Melting Point: 155° to 157° C.

Nuclear Magnetic Resonance Spectrum (hexadeuterated dimethyl sulfoxide) δ ppm: 1.34 (3H, triplet, J=7 Hz), 4.40 (2H, quartet, J=7 Hz), 7.57 (2H, triplet, J=8 Hz), 7.70 (1H, triplet, J=8 Hz), 8.01 (2H, doublet, J=8 Hz), 8.53 (1H, singlet), 12.1–12.5 (1H, broad, disappeared on adding deuterium oxide), 14.0–14.4 (1H, broad, disappeared on adding deuterium oxide).

PREPARATION 20

Isobutyl 2-aminothiazol-4-ylglyoxylate

A mixture comprising 10 g of potassium 2-aminothiazol-4-ylglyoxylate, 15 g of isobutyl alcohol and 50 ml of a 4N dioxane solution of hydrogen chloride was stirred at room temperature for 2 days. The reaction mixture was poured into water and neutralized with potassium carbonate, followed by extraction with ethyl acetate. The extract was dried over anhydrous magnesium sulfate and the ethyl acetate was evaporated off under reduced pressure, giving the desired compound as a pale yellow powder.

Melting Point: 105° to 108° C.

Nuclear Magnetic Resonance Spectrum (hexadeuterated dimethyl sulfoxide) δ ppm: 0.93 (6H, doublet, J=7 Hz), 1.98 (1H, septet, J=7 Hz), 4.08 (2H, doublet, J=7 Hz), 7.40 (2H, broad singlet), 7.89 (1H, singlet).

PREPARATION 21

Isobutyl 2-(3-phenylureido)thiazol-4-ylglyoxylate

Following a procedure similar to that described in Preparation 1, the desired compound was prepared from 1 g of isobutyl 2-aminothiazol-4-ylglyoxylate, 620 mg of phenyl isocyanate and 10 ml of tetrahydrofuran. The resulting product was a pale yellow powder having the following physical properties.

Melting Point: 190° to 200° C. (with decomposition).

Nuclear Magnetic Resonance Spectrum (hexadeuterated dimethyl sulfoxide) δ ppm: 0.96 (6H, doublet, J=7 Hz), 2.02 (1H, septet, J=7 Hz), 4.14 (2H, doublet, J=7 Hz), 7.06 (1H, triplet, J=7 Hz). 7.33 (2H, triplet, J=8 Hz), 7.48 (2H, doublet, J=7 Hz), 8.40 (1H, singlet), 8.92 (1H, broad singlet), 0.98 (1H, broad singlet).

PREPARATION 22

Ethyl 2-(3-o-fluorophenylureido)thiazol-4-ylglyoxylate

Following a procedure similar to that described in Preparation 1, the desired compound was prepared from 5 g of ethyl 2-aminothiazol-4-ylglyoxylate, 4.87 g of o-fluorophenyl isocyanate and 30 ml of dimethylformamide. The resulting product was a pale yellow powder having the following physical properties.

Melting Point: 219° to 225° C.

Nuclear Magnetic Resonance Spectrum (hexadeuterated dimethyl sulfoxide) δ ppm: 1.34 (3H, triplet, J=7 Hz), 4.38 (2H, quartet, J=7 Hz), 7.1–7.15 (1H. multiplet), 7.20 (1H, triplet, J=8 Hz), 7.29 (1H, doublet of doublets, J=11 and 8 Hz), 8.08 (1H, triplet, J=8 Hz), 8.43 (1H, singlet), 8.85 (1H, broad singlet, disappeared on adding deuterium oxide), 11.22 (1H, broad singlet. disappeared on adding deuterium oxide).

PREPARATION 23

Ethyl 2-(3-m-fluorophenylureido)thiazol-4-ylglyoxylate

Following a procedure similar to that described in Preparation 1, the desired compound was prepared from 5 g of ethyl 2-aminothiazol-4-ylglyoxylate, 4.9 g of m-fluorophenyl isocyanate and 30 ml of dimethylformamide. The resulting product was a pale yellow powder having the following physical properties.

Melting Point: 215° to 216° C.

Nuclear Magnetic Resonance Spectrum (hexadeuterated dimethyl sulfoxide) $\delta$ ppm: 1.33 (3H, triplet, J=7 Hz), 4.38 (2H, quartet, J=7 Hz), 6.89 (1H, doublet of triplets, J=2 and 8 Hz), 7.20 (1H, doublet of triplets, J=8 and 1 Hz), 7.36 (1H, doublet of triplets. J=7 and 8 Hz), 7.47 (1H, doublet of triplets, J=12 and 2 Hz), 8.43 (1H, singlet), 9.13 (1H. broad singlet), 1.13 (1H. broad singlet).

PREPARATION 24

Ethyl 2-[3-(2,4-difluorophenyl)ureido]thiazol-4-ylglyoxylate

Following a procedure similar to that described in Preparation 1, the desired compound was prepared from 5 g of ethyl 2-aminothiazol-4-ylglyoxylate, 5.8 g of 2,4-difluorophenyl isocyanate and 30 ml of dimethylformamide. The resulting product was a white powder having the following physical properties.

Melting Point: 245° to 263° C. (with decomposition).

Nuclear Magnetic Resonance Spectrum (hexadeuterated dimethyl sulfoxide) $\delta$ ppm: 1.33 (3H, triplet, J=7 Hz), 4.38 (2H, quartet. J=7 Hz), 7.05-7.15 (1H, multiplet), 7.35 (1H, doublet of doublets of doublets, J=11, 9 and 3 Hz), 8.00 (1H, doublet of triplets, J=6 and 9 Hz), 8.42 (1H, singlet), 8.79 (1H, broad singlet), 11.22 (1H, broad singlet).

PREPARATION 25

Ethyl 2-[3-(4-fluoro-3-nitrophenyl)ureido]thiazol-4-ylglyoxylate

Following a procedure similar to that described in Preparation 1, the desired compound was prepared from 5 g of ethyl 2-aminothiazol-4-ylglyoxylate. 5.5 g of 4-fluoro-3-nitrophenyl isocyanate and 30 ml of dimethylformamide. The resulting product was a yellow powder having the following physical properties.

Melting Point: 230°to 240° C. (with decomposition).

Nuclear Magnetic Resonance Spectrum (hexadeuterated dimethyl sulfoxide) $\delta$ ppm: 1.33 (3H, triplet, J=7 Hz), 4.38 (2H, quartet, J=7 Hz), 7.56 (1H, doublet of doublets, J=11 and 9 Hz), 7.76-7.85 (1H, multiplet), 8.42 (1H, doublet of doublets, J=6 and 3 Hz), 8.46 (1H, singlet), 9.40 (1H, broad singlet, disappeared on adding deuterium oxide), 11.42 (1H, broad singlet, disappeared on adding deuterium oxide).

PREPARATION 26

Ethyl 2-dimethylaminothiazol-4-ylglyoxylate

A mixture comprising 10 ml of a 2M benzene solution of dimethylamine, 1.3 g of ethyl 2-chlorothiazol-4-ylglyoxylate, and 5 ml of tetrahydrofuran was stirred for 3 hours at room temperature. The reaction mixture was poured into water and extracted with ethyl acetate. The extract was washed with water, dried over anhydrous magnesium sulfate, and concentrated under reduced pressure. The residue was purified by silica gel column chromatography, using as eluent a 9:1 by volume mixture of benzene and ethyl acetate, giving the title compound as a pale yellow oil.

Nuclear Magnetic Resonance Spectrum (CDCl$_3$) $\delta$ ppm: 1.40 (3H, triplet, J=7 Hz), 2.16 (6H, singlet), 4.41 (2H, quartet. J=7 Hz), 7.83 (1H, singlet).

PREPARATION 27

Ethyl 2-[3-(3,4,5-trimethoxyphenyl)ureido]thiazol-4-ylglyoxylate

Following a procedure similar to that described in Preparation 1, the desired compound was prepared from 4.3 g of ethyl 2-aminothiazol-4-ylglyoxylate, 5 g of 3,4,5-trimethoxyphenyl isocyanate and 30 ml of dimethylformamide. The resulting product was a yellow powder having the following physical properties.

Melting Point: 185° to 186° C.

Nuclear Magnetic Resonance Spectrum (hexadeuterated dimethyl sulfoxide) $\delta$ ppm: 1.33 (3H, triplet. J=7 Hz), 3.62 (3H. singlet), 3.77 (6H, singlet), 4.37 (2H, quartet, J=7 Hz), 6.82 (2H, singlet), 8.41 (1H, singlet), 8.88 (1H, broad singlet, disappeared on adding deuterium oxide), 10.9-11.3 (1H, broad, disappeared on adding deuterium oxide).

PREPARATION 28

Ethyl 2-(3-o-chlorophenylureido)thiazol-4-ylglyoxylate

Following a procedure similar to that described in Preparation 1, the desired compound was prepared from 26.7 g of ethyl 2-aminothiazol-4-ylglyoxylate, 23 g of o-chlorophenyl isocyanate and 300 ml of dimethylformamide. The resulting product was a white powder having the following physical properties.

Melting Point: 246° to 248° C. (with decomposition).

Nuclear Magnetic Resonance Spectrum (hexadeuterated dimethyl sulfoxide) $\delta$ ppm: 1.33 (3H, triplet. J=7 Hz), 4.38 (2H, quartet, J=7 Hz), 7.13 (1H, doublet of triplets, J=1.5 and 8 Hz), 7.35 (1H, doublet of triplets, J=1.5 and 8 Hz), 7.51 (1H, doublet of doublets, J=8 and 1.5 Hz), 8.13 (1H, doublet of doublets, J=8 and 1.5 Hz), 8.44 (1H, singlet), 8.66 (1H, broad singlet), 11.66 (1H, broad singlet).

PREPARATION 29

Ethyl 2-(3-p-tolylureido)thiazol-4-ylglyoxylate

Following a procedure similar to that described in Preparation 1. the desired compound was prepared from 12 g of ethyl 2-aminothiazol-4-ylglyoxylate. 10 g of p-tolyl isocyanate and 80 ml of dimethylformamide. The resulting product was a yellow powder having the following physical properties.

Melting Point: 210° to 212° C.

Nuclear Magnetic Resonance Spectrum (hexadeuterated dimethyl sulfoxide) $\delta$ ppm: 1.33 (3H, triplet, J=7 Hz), 2.26 (3H. singlet), 4.37 (2H, quartet. J=7 Hz), 7.13 (2H, doublet, J=9 Hz), 7.36 (2H, doublet, J=9 Hz), 8.40 (1H, singlet), 8.79 (1H, broad singlet), 0.97 (1H, broad singlet).

PREPARATION 30

Ethyl 2-[3-(2,6-xylyl)ureido]thiazol-4-ylglyoxylate

Following a procedure similar to that described in Preparation 1, the desired compound was prepared from 5 g of ethyl 2-aminothiazol-4-ylglyoxylate, 5.5 g of 2,6-xylyl isocyanate and 30 ml of dimethylformamide. The resulting product was a pale yellow powder having the following physical properties.

Melting point: 172° to 174° C.

Nuclear Magnetic Resonance Spectrum (hexadeuterated dimethyl sulfoxide) δ ppm: 1.33 (3H, triplet, J=7 Hz), 2.19 (6H, singlet), 4.37 (2H, quartet, J=7 Hz), 7.10 (3H, singlet), 8.09 (1H, broad singlet), 8.35 (1H, singlet), 11.21 (1H, broad singlet).

PREPARATION 31

Ethyl 2-(3-p-nitrophenylureido)thiazol-4-ylglyoxylate

Following a procedure similar to that described in Preparation 1, the desired compound was prepared from 4.88 g of ethyl 2-aminothiazol-4-ylglyoxylate, 5 g of p-nitrophenyl isocyanate and 30 ml of dimethylformamide. The resulting product was a pale yellow powder having the following physical properties.

Melting point: 243° to 265° C. (with decomposition).

Nuclear Magnetic Resonance Spectrum (hexadeuterated dimethyl sulfoxide) δ ppm: 1.33 (3H. triplet, J=7 Hz), 4.38 (2H, quartet, J=7 Hz), 7.75 (2H, doublet, J=9 Hz), 8.23 (2H, doublet, J=9 Hz), 8.47 (1H, singlet), 9.61 (1H, broad singlet), 11.33 (1H, broad singlet).

PREPARATION 32

Ethyl 2-(3-o-trifluoromethylphenylureido)thiazol-4-ylglyoxylate

Following a procedure similar to that described in Preparation 1, the desired compound was prepared from 4.28 g of ethyl 2-aminothiazol-4-ylglyoxylate. 5 g of o-trifluoromethylphenyl isocyanate and 40 ml of dimethylformamide. The resulting product was a white powder having the following physical properties.

Melting Point: circa 260° C. (with decomposition).

Nuclear Maqnetic Resonance Spectrum (hexadeuterated dimethyl sulfoxide) δ ppm: 1.33 (3H. triplet, J=7 Hz). 4.37 (2H, quartet, J=7 Hz), 7.38 (1H. broad triplet, J=8 Hz), 7.69-7.75 (2H, not defined), 7.94 (1H, broad doublet, J=8 Hz), 8.41 (1H, broad singlet), 8.42 (1H, singlet), 11.65 (1H, broad singlet).

PREPARATION 33

Ethyl 2-(3-p-trifluoromethylphenylureido)-thiazol-4-ylglyoxylate

Following a procedure similar to that described in Preparation 1, the desired compound was prepared from 4.28 g of ethyl 2-aminothiazol-4-ylglyoxylate, 5 g of p-trifluoromethylphenyl isocyanate and 40 ml of dimethylformamide. The resulting product was a pale yellow powder having the following physical properties.

Melting Point: 240° to 245° C. (with decomposition).

Nuclear Magnetic Resonance Spectrum (hexadeuterated dimethyl sulfoxide) δ ppm: 1.33 (3H, triplet, J=7 Hz), 4.38 (2H, quartet, J=7 Hz), 7.69 and 7.70 (4H, $A_2B_2$, J=10 Hz), 8.45 (1H, singlet), 9.31 (1H, broad singlet), 11.20 (1H, broad singlet).

PREPARATION 34

Ethyl 2-(3.3-diphenylureido)thiazol-4-ylglyoxylate

Following a procedure similar to that described in Preparation 13, the desired compound was prepared from 5 g of ethyl 2-aminothiazol-4-ylglyoxylate, 7 g of diphenylcarbamoyl chloride, 30 ml of triethylamine and 20 ml of dimethylformamide. The resulting product was a brown oil having the following physical properties.

Nuclear Magnetic Resonance Spectrum (CDCl$_3$) δ ppm: 1.38 (3H, triplet, J=7 Hz), 4.39 (2H, quartet, J=7 Hz), 7.2-7.5 (10H, multiplet), 8.27 (1H, singlet).

PREPARATION 35

Ethyl 2-(3-methylureido)thiazol-4-ylglyoxylate

Following a procedure similar to that described in Preparation 1, the desired compound was prepared from 10 g of ethyl 2-aminothiazol-4-ylglyoxylate. 7 g of methyl isocyanate and 200 ml of ethyl acetate. The resulting product was a pale yellow powder having the following physical properties.

Melting Point: 210° to 213° C.

Nuclear Magnetic Resonance Spectrum (hexadeuterated dimethyl sulfoxide) δ ppm: 1.32 (3H, triplet. J=7 Hz), 2.71 (3H, doublet. J=4 Hz), 4.37 (2H, quartet, J=7 Hz), 6.41 (1H, broad quartet, J=4 Hz, disappeared on adding deuterium oxide), 8.31 (1H, singlet), 11.08 (1H, broad singlet, disappeared on adding deuterium oxide).

PREPARATION 36

Ethyl 2-(3-benzylureido)thiazol-4-ylglyoxylate

Following a procedure similar to that described in Preparation 1, the desired compound was prepared from 4.7 g of ethyl 2-aminothiazol-4-ylglyoxylate, 4.5 g of benzyl isocyanate and 30 ml of dimethylformamide. The resulting product was a yellow powder having the following physical properties.

Melting Point: circa 218° C. (with decomposition).

Nuclear Magnetic Resonance Spectrum (hexadeuterated dimethyl sulfoxide) δ ppm: 1.32 (3H, triplet, J=7 Hz), 4.36 (2H, quartet, J=7 Hz), 4.37 (2H, singlet), 7.03 (1H. broad triplet. J=6 Hz). 7.2-7.4 (5H, multiplet). 8.33 (1H, singlet), 11.08 (1H, broad singlet, disappeared on adding deuterium oxide).

PREPARATION 37

Ethyl 2-(3-cyclohexylureido)thiazol-4-ylglyoxylate

Following a procedure similar to that described in Preparation 1. the desired compound was prepared from 5 g of ethyl 2-aminothiazol-4-ylglyoxylate, 4.7 g of cyclohexyl isocyanate and 30 ml of dimethylformamide. The resulting product was a yellow powder having the following physical properties.

Melting Point: 212° to 215° C.

Nuclear Magnetic Resonance Spectrum (hexadeuterated dimethyl sulfoxide) δ ppm: 1.1-1.4 (5H. not defined), 1.32 (3H, triplet. J=7 Hz). 1.5-1.6 (1H, multiplet), 1.6-1.75 (2H, multiplet), 1.75-1.9 (2H, multiplet), 3.45-3.6 (1H, multiplet), 4.35 (2H, quartet, J=7 Hz), 6.44 (1H, broad doublet, J=8 Hz), 8.31 (1H, singlet), 10.64 (1H, broad singlet).

PREPARATION 38

Ethyl 2-[3-(2,4,6-trifluoroohenyl)ureido]thiazol-4-ylglyoxylate

A mixture comprising 25 g of carbonyldiimidazole, 30.87 g of ethyl 2-aminothiazol-4-ylglyoxylate and 300 ml of tetrahydrofuran was stirred at room temperature for 1 day. After completion of the reaction, the crystals which precipitated out were collected by filtration and washed with ethyl acetate to give crude ethyl 2-(1-imidazolylcarbonylamino)thiazol-4-ylglyoxylate.

A mixture comprising 7.92 g of this crude intermediate, 5 g of 2,4,6-trifluoroaniline and 100 ml of dimethylformamide was stirred overnight at room temperature. The reaction mixture was concentrated under reduced pressure and then ethyl acetate was added. Insolubles were filtered off, and the filtrate was purified by silica gel column chromatography, using as eluent a 8:2:1 to 6:2:1 mixture of hexane, ethyl acetate and acetic acid.

The resulting product was a white powder having the following physical properties.

Melting Point: 242° to 248° C. (with decomposition).

Nuclear Magnetic Resonance Spectrum (hexadeuterated dimethyl sulfoxide) δ ppm: 1.32 (3H, triplet, J=7 Hz). 4.37 (2H, quartet, J=7 Hz), 7.31 (2H, doublet of doublets, J=9 and 8 Hz), 8.41 (1H, singlet), 8.42 (1H, singlet, disappeared on adding deuterium oxide), 11.60 (1H. broad singlet, disappeared on adding deuterium oxide).

PREPARATION 39

2-Diethylaminothiazole-4-carbaldehyde

The reaction described in Preparation 26 was repeated, but using 2.3 g of diethylamine, 4 g of ethyl 2-chlorothiazole-4-carboxylate, 4.2 g of triethylamine, and 15 ml of dimethylformamide, giving ethyl 2-diethylaminothiazole-4-carboxylate as a pale yellow oil.

Nuclear Magnetic Resonance Spectrum (CDCl$_3$) δ ppm: 1.24 (6H, triplet, J=7 Hz), 1.37 (3H, triplet, J=7 Hz), 3.53 (4H, quartet, J=7 Hz), 4.34 (2H, quartet, J=7 Hz), 7.36 (1H, singlet).

The reaction described in Preparation 15 was then repeated, but using 1.9 g of the above ester, 0.31 g of lithium aluminum hydride, and 40 ml of tetrahydrofuran, giving 2-diethylaminothiazol-4-ylmethanol as colorless prisms.

Melting Point: 67° to 69° C.

A dimethyl sulfoxide (10 ml) solution of 3.3 g of pyridine sulfur trioxide complex was added dropwise, with stirring and at room temperature, to a mixture comprising 1.3 g of the above methanol derivative, 2.1 g of triethylamine and 10 ml of dimethyl sufoxide. The reaction mixture was stirred for 30 minutes at the same temperature, then poured into water and extracted with ethyl acetate. The extract was dried over anhydrous sodium sulfate and concentrated under reduced pressure. The residue was purified by silica gel column chromatography, using as eluent a 5:1 by volume mixture of benzene and ethyl acetate giving the title compound as a pale brown oil.

Nuclear Magnetic Resonance Spectrum (CDCl$_3$) δ ppm: 1.26 (6H, triplet, J=7 Hz), 3.54 (4H, quartet, J=7 Hz), 7.39 (1H, singlet), 9.74 (1H, singlet).

PREPARATION 40

Ethyl 2-(3-o-fluorophenylthioureido)thiazol-4-yl-glyoxylate

Following a procedure similar to that described in Preparation 1. the desired compound was prepared from 15 g of ethyl 2-aminothiazol-4-ylglyoxylate, 17 g of o-fluorophenyl isothiocyanate and 30 ml of hexamethylphosphoric triamide. The resulting product was a pale yellow powder having the following physical properties.

Melting Point: 192° to 193° C.

Nuclear Magnetic Resonance Spectrum (hexadeuterated dimethyl sulfoxide) δ ppm: 1.32 (3H. triplet, J=7 Hz), 4.37 (2H, quartet, J=7 Hz), 7.2–7.35 (3H, multiplet), 7.79 (1H, triplet. J=8 Hz), 8.39 (1H, singlet), 10.12 (1H, broad singlet, disappeared on adding deuterium oxide), 12.45 (1H, broad singlet, disappeared on adding deuterium oxide).

PREPARATION 41

Ethyl 2-(3-p-fluorophenylthioureido)thiazol-4-ylglyoxylate

Following a procedure similar to that described in Preparation 1, the desired compound was prepared from 5 g of ethyl 2-aminothiazol-4-ylglyoxylate, 4.6 g of p-fluorophenyl isothiocyanate and 20 ml of dimethyl sulfoxide. The resulting product was a pale yellow powder having the following physical properties.

Melting Point: 170° to 172° C.

Nuclear Magnetic Resonance Spectrum (hexadeuterated dimethyl sulfoxide) δ ppm: 1.32 (3H. triplet, J=7 Hz). 4.37 (2H, quartet, J=7 Hz), 7.23 (2H, triplet, J=9 Hz), 7.5–7.8 (2H, multiplet), 8.37 (1H, singlet), 10.34 (1H, broad singlet), 11.9–12.4 (1H, broad).

PREPARATION 42

Ethyl 2-anilinothiazole-4-carboxylate

A mixture comprising 8.6 g of phenylthiourea, 10 g of ethyl bromopyruvate and 100 ml of ethanol was heated under reflux for 3 hours, and the reaction mixture was then concentrated under reduced pressure. A saturated aqueous sodium hydrogen carbonate solution was added to the residue, followed by extraction with ethyl acetate. The extract was dried over anhydrous sodium sulfate and evaporated under reduced pressure. The crystals which formed were collected by filtration. washed with benzene, and then recrystallized from ethanol, giving the desired compound as pale yellow prismatic crystals.

Melting Point: 140.5° to 142° C.

Nuclear Magnetic Resonance Spectrum (hexadeuterated acetone) δ ppm: 1.33 (3H, triplet, J=7 Hz), 4.29 (2H, quartet, J=7 Hz), 6.98 (1H, triplet, J=8 Hz), 7.32 (2H, triplet, J=8 Hz), 7.60 (1H, singlet), 7.72 (2H, doublet, J=8 Hz), 9.33 (1H, broad singlet).

PREPARATION 43

2-Anilinothiazol-4-ylmethanol

Following a procedure similar to that described in Preparation 15, the desired compound was prepared from 8.5 g of ethyl 2-anilinothiazol-4-carboxylate, 2 g of lithium aluminum hydride and 150 ml of tetrahydrofuran, as colorless flakes having the following physical properties.

Melting Point: 115° to 118° C.

Nuclear Magnetic Resonance Spectrum (hexadeuterated acetone) δ ppm: 3.8–4.4 (1H. broad). 4.58 (2H, singlet), 6.59 (1H, singlet), 6.94 (1H, triplet, J=8 Hz), 7.30 (2H, triplet, J=8 Hz), 7.68 (2H, doublet, J=8 Hz), 8.8–9.4 (1H, broad).

PREPARATION 44

2-Anilinothiazole-4-carbaldehyde

A dimethyl sulfoxide solution (120 ml) of 20 g of sulfur trioxide pyridine complex was added dropwise to a mixture comprising 8.3 g of 2-anilinothiazol-4-ylmethanol, 16.5 ml of triethylamine and 120 ml of dimethyl sulfoxide. The resulting mixture was stirred at room temperature for 10 minutes and then poured into water. followed by extraction with ethyl acetate. The extract was washed successively with aqueous acetic acid, aqueous sodium chloride solution and aqueous sodium hydrogen carbonate solution, and dried over anhydrous sodium sulfate. The residue afforded by evaporation of the solvent under reduced pressure was recrystallized from a mixture of benzene and acetone. The resulting product was a brown powder having the following physical properties.

Melting Point: 145° to 147° C.

Nuclear Magnetic Resonance Spectrum (hexadeuterated acetone) δ ppm: 7.03 (1H, triplet, J=8 Hz), 7.36 (2H, triplet, J=8 Hz), 7.77 (2H, doublet, J=8 Hz), 7.83 (1H, singlet), 9.2–9.6 (1H, broad). 9 80 (1H, singlet).

PREPARATION 45

Ethyl 2-o-toluidinothiazole-4-carboxylate

Following a procedure similar to that described in Preparation 42, the desired compound was prepared from 20 g of o-tolylthiourea, 23 g of ethyl bromopyruvate and 200 ml of giving the desired compound as pale yellow prismatic crystals having the following physical properties.

Melting Point: 130° to 132.5° C.

Nuclear Magnetic Resonance Spectrum (hexadeuterated acetone) δ ppm: 1.30 (3H, triplet, J=7 Hz), 2.34 (3H, singlet), 4.24 (2H, quartet, J=7 Hz). 7.0–7.4 (3H. multiplet), 7.58 (1H, singlet), 7.89 (1H, doublet, J=8 Hz), 8.77 (1H, broad singlet).

PREPARATION 46

2-o-Toluidinothiazol-4-ylmethanol

Following a procedure similar to that described in Preparation 15, the desired compound was prepared from 10 g of ethyl 2-o-toluidinothiazole-4-carboxylate, 2.9 g of lithium aluminum hydride and 200 ml of tetrahydrofuran. The resulting product was a brown oil having the following physical properties.

Nuclear Magnetic Resonance Spectrum (hexadeuterated acetone) δ ppm: 2.34 (3H. singlet), 4.56 (2H. singlet), 6.57 (1H. singlet), 6.9–7.4 (3H multiplet), 7.92 (1H doublet. J=8 Hz).

PREPARATION 47

2-o-Toluidinothiazole-4-carbaldehyde

Following a procedure similar to that described in Preparation 44, the desired compound was prepared from 6.12 g of 2-(o-toluidino)thiazole-4-ylmethanol, 13.2 g of a sulfur trioxide pyridine complex, 12 ml of triethylamine and 210 ml of dimethyl sulfoxide, as pale brown prismatic crystals having the following physical properties.

Melting Point: 104° to 111° C.

Nuclear Magnetic Resonance Spectrum (hexadeuterated acetone) δ ppm: 2.36 (3H, singlet), 6.95–7.4 (3H, multiplet), 7.76 (1H, singlet), 7.97 (1H, doublet, J=8 Hz), 8.5–8.9 (1H, broad), 9.78 (1H, singlet).

PREPARATION 48

Ethyl 3-(2-anilinothiazol-4-yl)acrylate (Approximately 3:1 mixture of E and Z isomers)

A mixture comprising 3.5 g of 2-anilinothiazole-4-carbaldehyde, 6.5 g of (ethoxycarbonylmethylene)triphenylphosphorane and 35 ml of tetrahydrofuran was heated at 60° C. for 2 hours. The reaction mixture was poured into water and extracted with benzene. The benzene extract was dried over anhydrous sodium sulfate, and the solvent was evaporated off under reduced pressure, giving an oil. This oil was purified by silica gel column chromatography. using as eluent a 9:1 mixture of benzene and ethyl acetate, giving the desired compound as yellow crystals.

Melting Point: 113° to 118° C.

Nuclear Magnetic Resonance Spectrum (hexadeuterated dimethyl sulfoxide) δ ppm:

For the E isomer: 1.27 (3H, triplet. J=7 Hz), 4.19 (2H. quartet. J=7 Hz). 6.46 (1H, doublet, J=16 Hz), 6.97 (1H, triplet. J=7 Hz), 7.35 (2H, triplet, J=7 Hz), 7.40 (1H, singlet), 7.46 (1H, doublet. J=16 Hz), 7.69 (2H, doublet, J=7 Hz), 10.33 (1H, broad singlet).

For the Z isomer: 1.18 (3H, triplet. J=7 Hz). 4.17 (2H, quartet, J=7 Hz), 5.97 (1H, doublet, J=13 Hz), 6.70 (1H, doublet, J=13 Hz), 6.9–6.96 (1H, not defined), 7.28 (2H, triplet, J=7 Hz), 7.44 (1H, singlet), 7.61 (2H, doublet, J=7 Hz), 10.17 (1H. broad singlet).

PREPARATION 49

(E)-3-(2-Anilinothiazol-4-yl)acrylaldehyde 58 ml of a 1M hexane solution of diisobutyl aluminum hydride was added dropwise at −60° C. to a solution of 4 g of ethyl 3-(2-anilinothiazol-4-yl)acrylate (prepared by the procedure described in Preparation 48) in 40 ml of tetrahydrofuran. The resulting mixture was stirred at −50° C. for 2 hours, then the excess of the reducing reagent was decomposed with 90% aqueous methanol. The mixture was then neutralized with 3N hydrochloric acid and extracted with ethyl acetate. After the extract was dried over anhydrous sodium sulfate. the solvent was evaporated off under reduced pressure, giving crude 3-(2-anilinothiazol-4-yl)allyl alcohol.

2.6 g of the crude alcohol thus obtained were dissolved in 20 ml of dimethyl sulfoxide, and 3.4 g of triethylamine were added to the resulting solution. Next, a solution of 5.3 g of a sulfur trioxide pyridine complex in dimethyl sulfoxide (10 ml) was added dropwise to the reaction mixture at room temperature, and the mixture was stirred at the same temperature for 30 minutes. The reaction mixture was then poured into water, acidified with 3N hydrochloric acid, and extracted with ethyl acetate. After the extract was dried over anhydrous sodium sulfate, the solvent was evaporated off under reduced pressure. The residue was purified by silica gel column chromatography, using as eluent a 10:1 mixture of benzene and ethyl acetate, giving the desired compound as pale yellow crystals.

Melting Point: 142° to 143° C.

Nuclear Magnetic Resonance Spectrum (hexadeuterated dimethyl sulfoxide) δ ppm: 6.67 (1H. doublet of doublets, J=15 and 8 Hz), 6.98 (1H, triplet, J=8 Hz), 7.35 (2H, triplet, J=8 Hz), 7.53 (1H, singlet), 7.54 (1H, doublet, J=15 Hz), 7.69 (2H, doublet, J=8 Hz), 9.67 (1H, doublet, J=8 Hz), 10.38 (1H, broad singlet, disappeared on adding deuterium oxide).

PREPARATION 50

2-(3-p-Bromophenylureido)thiazole-4-carbaldehyde 2.4 g of sodium borohydride were added to a suspension of 5 g of ethyl 2-(3-p-bromophenylureido)thiazol-4-ylglyoxylate in 60 ml of tetrahydrofuran, then 20 ml of methanol were added dropwise over a period of 1 hour while heating the reaction mixture under reflux, and the reaction mixture was thereafter heated under reflux for a further 1 hour. The reaction mixture was poured into water and neutralized with 3N hydrochloric acid. The crystals which precipitated out were collected by filtration, washed with water and dried, giving crude 1-[2-(3-p-bromophenyl- ureido)thiazol-4-yl]ethane-1,2-diol.

Melting Point: 182° to 187° C. (with decomposition)

Subsequently, 4.3 g of the crude diol thus obtained were suspended in 200 ml of tetrahydrofuran. and an aqueous solution (30 ml) of 5.1 g of sodium metaperiodate was added dropwise to it under ice-cooling. The resulting mixture was stirred at the same temperature for 1 hour. and then for a further 1 hour at room temperature. The reaction mixture was poured into ice water and the crystals which precipitated out were collected by filtration. The resulting product was a white powder having the following physical properties.

Decomposition point: circa 250 ° C.

Nuclear Magnetic Resonance Spectrum (hexadeuterated dimethyl sulfoxide) δ ppm: 7.47 and 7.50 (4H, $A_2B_2$, J=9 Hz), 8.24 (1H, singlet), 9.16 (1H, broad singlet), 9.75 (1H, singlet), 10.93 (1H, broad singlet).

PREPARATION 51

(E)-3-[2-(3-p-Bromophenylureido)thiazol-4-yl]allyl alcohol

Following a procedure similar to that described in Preparation 48, crude ethyl 3-[2-(3-p-bromophenylureido)thiazol-4-yl]acrylate was prepared from 1 g of 2-(3-p-bromophenylureido)thiazole-4-carbaldehyde, 1.2 g of ethoxycarbonylmethylenetriphenylphosphorane and 20 ml of tetrahydrofuran. Subsequently. following a procedure similar to that described in Preparation 49, the desired compound was prepared from 1.1 g of the above crude ethyl ester, 14 ml of a 1M hexane solution of diisobutyl aluminum hydride and 30 ml of tetrahydrofuran. The resulting product was a white powder having the following physical properties.

Decomposition point: circa 220 ° C.

Nuclear Magnetic Resonance Spectrum (hexadeuterated dimethyl sulfoxide) δ ppm: 4.10 (2H doublet of doublets. J=5 and 3 Hz converted to doublet (J=3 Hz) on adding deuterium oxide), 4.84 (1H, triplet, J=5 Hz, disappeared on adding deuterium oxide), 6.40 (1H, doublet of doublets. J=16 and 3 Hz). 6.47 (1H, doublet, J=16 Hz), 6.94 (1H, singlet), 7.46 and 7.48 (4H, $A_2B_2$, J=9 Hz), 9.15 (1H. broad singlet, disappeared on adding deuterium oxide), 10.66 (1H, broad singlet, disappeared on adding deuterium oxide).

PREPARATION 52

(E)-3-[2-(3-p-Bromophenylureido)thiazol-4-yl]acrylaldehyde

Following a procedure similar to that described in Preparation 49, the desired compound was prepared from 0.84 g of (E)-3-[2-(3-p-bromophenylureido)-thiazol-4-yl]allyl alcohol, 1.13 g of a sulfur trioxide pyridine complex, 0.72 g of triethylamine and 20 ml of dimethyl sulfoxide. The resulting product was a pale brown powder having the following physical properties.

Decomposition point: circa 260° C.

Nuclear Magnetic Resonance Spectrum (hexadeuterated dimethyl sulfoxide) δ ppm: 6.61 (1H, doublet of doublets, J=15 and 8 Hz), 7.4-7.55 (4H, multiplet), 7.61 (1H, doublet, J=15 Hz), 7.73 (1H, singlet), 9.13 (1H, singlet, disappeared on adding deuterium oxide), 9.66 (1H, doublet, J=8 Hz), 10.6-11.2 (1H, broad, disappeared on adding deuterium oxide).

PREPARATION 53

Ethyl 2-[bis(o-fluorophenyl)methylamino]thiazol-4-ylglyoxylate

A mixture comprising 1.01 g of ethyl 2-aminothiazol-4-ylglyoxylate, 1.48 g of bis(p-fluorophenyl)methyl chloride, 0.75 g of triethylamine, 3 ml of dimethylformamide and 0.35 g of pulverized potassium iodide was stirred at 85° to 90° C. for 7.5 hours. After the reaction mixture was cooled, a saturated aqueous sodium hydrogen carbonate solution was added thereto, followed by extraction with ethyl acetate. The extract was dried over anhydrous sodium sulfate and the solvent was evaporated off under reduced pressure. The residue was purified by silica gel column chromatography, using as eluent a 10:1 mixture of benzene and ethyl acetate. The resulting product was recrystallized from benzene, giving the desired compound as yellow crystals having the following physical properties.

Melting Point: 122° to 124° C.

Nuclear Magnetic Resonance Spectrum (hexadeuterated dimethyl sulfoxide) δ ppm: 1.25 (3H, triplet, J=7 Hz). 4.29 (2H, quartet, J=7 Hz), 6.05 (1H, doublet, J=8 Hz), 7.12-7.21 (4H, multiplet). 7.33-7.42 (4H, multiplet), 8.01 (1H, singlet), 8.92 (1H, doublet, J=8 Hz).

PREPARATION 54

Ethyl 2-diphenylmethylaminothiazol-4-ylglyoxylate

Following a procedure similar to that described in Preparation 53, the desired compound was prepared from 10.1 g of 2-aminothiazol-4-ylglyoxylate, 10.0 g of diphenylmethyl chloride, 10 ml of triethylamine, 10 ml of dimethylformamide and 1.0 g of potassium iodide. The resulting product was a yellow powder having the following physical properties.

Melting Point: 82° to 85° C.

Nuclear Magnetic Resonance Spectrum ($CDCl_3$) δ ppm: 1.38 (3H, triplet, J=7 Hz), 4.38 (2H, quartet, J=7 Hz), 5.64 (1H, doublet, J=6 Hz), 6.04 (1H, broad doublet, J=6 Hz), 7.3-7.4 (10H, multiplet), 7.86 (1H, singlet).

PREPARATION 55

1-(2-Diphenylaminothiazol-4-yl)ethane-1,2-diol

Following a procedure similar to that described in Preparation 50, the desired compound was prepared from 1.68 g of ethyl 2-diphenylmethylaminothiazol-4-ylglyoxylate, 0.35 g of sodium borohydride, 3 ml of methanol and 8 ml of tetrahydrofuran. The resulting product was a white powder having the following physical properties.

Softening Point: 143° to 148 ° C.

Nuclear Magnetic Resonance Spectrum ($CDCl_3$) δ ppm: 3.73 (1H, doublet of doublets, J=11 and 4 Hz), 3.81 (1H, doublet of doublets, J=11 and 4 Hz), 3.8-4.3 (2H, broad, disappeared on adding deuterium oxide), 4.58 (1H, triplet, J=4 Hz), 5.57 (1H, singlet), 6.33 (1H, singlet). 7.2-7.35 (10H, multiplet).

PREPARATION 56

2-Diphenylmethylaminothiazole-4-carbaldehyde

Following a procedure similar to that described in Preparation 50, the desired compound was prepared from 2.11 g of 1-(2-diphenylmethylaminothiazol-4-yl)ethane-1,2-diol, 3.15 g of sodium metaperiodate, 40 ml of water and 20 ml of methanol. The resulting product was a pale brown foam having the following physical properties.

Nuclear Magnetic Resonance Spectrum (CDCl$_3$) δ ppm: 5.68 (1H, singlet), 7.3–7.4 (1H, not defined). 9.65 (1H, singlet).

Mass spectrum (m/e): 294 (M+).

PREPARATION 57

Ethyl 2-p-fluoroanilinothiazole-4-carboxylate

The reaction described in Preparation 42 was repeated, but using 12 g of p-fluorophenylthiourea, 14.8 g of ethyl bromopyruvate, and 120 ml of ethanol, giving the title compound as pale yellow prisms.

Melting Point: 133° to 136° C.

Nuclear Magnetic Resonance Spectrum (hexadeuterated acetone) δ ppm: 1.34 (3H, triplet. J=7 Hz), 4.31 (2H, quartet, J=7 Hz), 7.10 (2H, triplet, J=9 Hz), 7.65 (1H, singlet), 7.78 (2H, doublet of doublets, J=9 and 5 Hz), 9.2.–9.6 (1H, broad).

PREPARATION 58

2-p-Fluoroanilinothiazol-4-ylmethanol

The reaction described in Preparation 50 was repeated, but using 12.04 g of ethyl 2-p-fluoroanilinothiazole-4-carboxylate, 6 g of sodium borohydride, 120 ml of anhydrous tetrahydrofuran, and 70 ml of absolute methanol, giving the title compound as colorless prisms.

Melting Point: 156° to 161° C.

Nuclear Magnetic Resonance Spectrum (hexadeuterated acetone) δ ppm: 4.05 (1H, broad triplet, J=5 Hz), 4.56 (2H, broad doublet, J=5 Hz), 6.60 (1H, singlet), 7.07 (2H, triplet. J=9 Hz), 7.74 (2H. doublet of doublets, J=9 and 5 Hz), 8.9–9.4 (1H, broad).

PREPARATION 59

2-p-Fluoroanilinothiazole-4-carbaldehyde

The reaction described in Preparation 44 was repeated, but using 3.03 g of 2-p-fluoroanilinothiazol-4-ylmethanol, 8.5 g of pyridine sulfur trioxide complex, 7.5 ml of triethylamine and 140 ml of dimethyl sulfoxide. giving the title compound as pale brown prisms.

Melting Point: 152° to 155° C.

Nuclear Magnetic Resonance Spectrum (hexadeuterated acetone) δ ppm: 7.12 (2H, triplet, J=9 Hz), 7.7–7.9 (2H. not defined), 7.86 (1H, singlet), 9.3–9.7 (1H, broad), 9.83 (1H, singlet).

PREPARATION 60

Ethyl 2-p-anisidinothiazole-4-carboxylate

The reaction described in Preparation 42 was repeated, but using 10.03 g of 4-methoxyphenylthiourea. 10 g of ethyl bromopyruvate, and 100 ml of ethanol, giving the title compound as pale yellow prisms.

Melting Point: 119° to 120.5° C.

Nuclear Magnetic Resonance Spectrum (hexadeuterated acetone) δ ppm: 1.33 (3H, triplet, J=7 Hz), 3.80 (3H. singlet,). 4.29 (2H, quartet, J=7 Hz), 6.94 (2H, doublet, J=9 Hz), 7.55–7.7 (3H, not defined), 9.13 (1H, broad singlet).

PREPARATION 61

2-p-Anisidinothiazol-4-ylmethanol

The reaction described in Preparation 15 was repeated, but using 5.0 g of ethyl 2-p-anisidinothiazole-4-carboxylate, 1 5 g of lithium aluminum hydride and 100 ml of anhydrous tetrahydrofuran, giving the title compound as a pale red powder.

Melting Point: 104° to 105° C.

Nuclear Magnetic Resonance Spectrum (hexadeuterated acetone) δ ppm: 3.80 (3H, singlet), 3.8–4.3 (1H, broad), 4.56 (2H, broad singlet), 6.53 (1H, singlet), 6.91 (2H, doublet, J=9 Hz), 7.59 (2H, doublet, J=9 Hz), 8.7–9.1 (1H, broad).

PREPARATION 62

2-p-Anisidinothiazole-4-carbaldehyde

The reaction described in Preparation 44 was repeated, but using 3 g of 2-p-anisidinothiazol-4-ylmethanol, 6.1 g of pyridine sulfur trioxide complex, 5.3 ml of triethylamine and 90 ml of dimethyl sulfoxide, giving the title compound as pale brown crystals.

Melting Point: 108° to 110° C.

Nuclear Magnetic Resonance Spectrum (hexadeuterated acetone) δ ppm: 3.80 (3H, singlet), 6.94 (2H, doublet. J=9 Hz), 7.65 (2H, doublet, J=9 Hz), 7.76 (1H, singlet), 9.0–9.4 (1H, broad), 9.79 (1H, singlet).

PREPARATION 63

Ethyl 2-m-trifluoromethylanilinothiazole-4-carboxylate

The reaction described in Preparation 42 was repeated, but using 10.02 g of m-trifluoromethylphenylthiourea, 8.8 g of ethyl bromopyruvate and 100 ml of ethanol, giving the title compound as pale yellow crystals.

Melting Point: 124.5° to 127° C.

Nuclear Magnetic Resonance Spectrum (hexadeuterated acetone) δ ppm: 1.36 (3H. triplet, J=7 Hz), 4.31 (2H, quartet, J=7 Hz), 7.25–7.7 (2H, not defined), 7.75 (1H, singlet), 7.97 (1H, broad doublet, J=8 Hz). 8.35 (1H. broad singlet), 9.6–9.9 (1H, broad).

PREPARATION 64

2-m-Trifluoromethylanilinothiazol-4-ylmethanol

The reaction described in Preparation 15 was repeated, but using 3.92 g of ethyl 2-m-trifluoromethylanilinothiazole-4-carboxylate, 1 g of lithium aluminum hydride and 80 ml of anhydrous tetrahydrofuran, giving the title compound as a colorless powder.

Melting Point: 126.5° to 128° C.

Nuclear Magnetic Resonance Spectrum (hexadeuterated acetone) δ ppm: 4.16 (1H, broad triplet, J=5 Hz), 4.61 (2H, broad doublet, J=5 Hz), 6.70 (1H, singlet), 7.26 (1H, broad doublet, J=8 Hz), 7.53 (1H, triplet, J=8 Hz), 7.99 (1H. broad doublet, J=8 Hz), 8.17 (1H, broad singlet), 9.1–9.9 (1H, broad).

PREPARATION 65

2-m-Trifluoromethylanilinothiazole-4-carbaldehyde

The reaction described in Preparation 44 was repeated, but using 2.65 g of 2-m-trifluoromethylanilinothiazol-4-ylmethanol, 4.8 g of pyridine sulfur trioxide complex, 4.2 ml of triethylamine and 90 ml of dimethyl sulfoxide, giving the title compound as a pale brown powder.

Melting Point: 151° to 153° C.

Nuclear Magnetic Resonance Spectrum (hexadeuterated acetone) δ ppm: 7.34 (1H, broad doublet, J=8 Hz). 7.58 (1H, triplet, J=8 Hz), 7.94 (1H, singlet), 8.06 (1H, broad doublet, J=8 Hz), 8.26 (1H, broad singlet), 9.6–10.0 (1H, broad), 9.87 (1H, singlet).

PREPARATION 66

Ethyl 2-ethylaminothiazole-4-carboxylate

The reaction described in Preparation 42 was repeated but using 10 g of ethylthiourea, 20 g of ethyl bromopyruvate and 100 ml of ethanol, giving the title compound as a pale yellow powder.

Melting point: 93° to 95° C.

Nuclear Magnetic Resonance Spectrum (hexadeuterated dimethyl sulfoxide) δ ppm: 1.17 (3H triplet. J =7 Hz), 1.28 (3H, triplet, J=7 Hz), 3.1–3.4 (2H, not defined), 4.23 (2H, quartet, J=7 Hz), 7.51 (1H, singlet), 7.76 (1H, broad triplet. J=5 Hz).

PREPARATION 67

2-Ethylaminothiazol-4-ylmethanol

The reaction described in Preparation 17 was repeated but using 10 g of ethyl 2-ethylaminothiazole-4-carboxylate, 3.8 g of sodium borohydride, 70 ml of methanol and 150 ml of tetrahydrofuran, giving the title compound as a yellow oil.

Nuclear Magnetic Resonance Spectrum (CDCl$_3$) δ ppm: 1.30 (3H. triplet, J=7 Hz), 3.24 (2H, quartet, J=7 Hz), 4.51 (2H, singlet), 6.2–6.5 (3H, not defined, changed to 6.34 (1H, singlet) on adding deuterium oxide).

PREPARATION 68

2-Ethylaminothiazole-4-carbaldehyde

The reaction described in Preparation 44 was repeated, but using 4.4 g of 2-ethylaminothiazol-4-ylmethanol, 13.3 g of sulfur trioxide pyridine complex, 8.4 g of triethylamine and 60 ml of dimethyl sulfoxide, giving the title compound as pale brown prisms.

Melting Point: 84° to 85° C.

Nuclear Magnetic Resonance Spectrum (CDCl$_3$) δ ppm: 1.32 (3H, triplet, J=7 Hz), 3.2–3.6 (2H, multiplet), 6.3–6.7 (1H, broad), 7.40 (1H. singlet), 9.70 (1H, singlet).

PREPARATION 69

Ethyl 2-allylaminothiazole-4-carboxylate

The reaction described in Preparation 42 was repeated but using 20 g of allylthiourea, 37 g of ethyl bromopyruvate and 200 ml of ethanol, giving the title compound as a pale yellow powder.

Melting Point: 85° to 86° C.

Nuclear Magnetic Resonance Spectrum (hexadeuterated dimethyl sulfoxide) δ ppm: 1.26 (3H. triplet, J=7 Hz), 3.84–3.90 (2H, multiplet), 4.21 (2H. quartet, J=7 Hz), 5.13 (1H. doublet of doublets of doublets, J=10, 3and 1.5 Hz), 5.24 (1H, doublet of doublets of doublets, J=17, 3and 1.5 Hz), 5.8–5.97 (1H, multiplet), 7.51 (1H, singlet), 7.96 (1H, broad triplet, J=5 Hz).

PREPARATION 70

2-allylaminothiazol-4-ylmethanol

The reaction described in Preparation 15 was repeated, but using 10 g of ethyl 2-allylaminothiazole-4-carboxylate, 2.7 g of lithium aluminum hydride and 150 ml of tetrahydrofuran. giving the title compound as pale brown needles.

Melting Point: 74° to 75° C.

Nuclear Magnetic Resonance Spectrum (CDCl$_3$) δ ppm: 3.1–3.9 (1H, broad), 3.86 (2H, broad doublet, J=5 Hz), 4.51 (2H, singlet), 5.1–5.45 (2H, multiplet), 5.5–6.2 (2H, multiplet), 6.37 (1H, singlet).

PREPARATION 71

2-Allylaminothiazole-4-carbaldehyde

The reaction described in Preparation 44 was repeated, but using 11 g of 2-allylaminothiazol-4-ylmethanol, 31 g of sulfur trioxide pyridine complex, 20 g of triethylamine and 100 ml of dimethyl sulfoxide, giving the title compound as pale brown needles.

Melting Point: 106° to 107° C.

Nuclear Magnetic Resonance Spectrum (CDCl$_3$) δ ppm: 4.05 (2H, broad singlet). 5.1–5.5 (2H, multiplet), 5.7–6.15 (1H, multiplet), 7.3–7.7 (1H, broad), 7.40 (1H, singlet), 9.69 (1H, singlet).

PREPARATION 72

Ethyl 2-cyclohexylaminothiazole-4-carboxylate

The reaction described in Preparation 42 was repeated, but using 17 g of cyclohexylthiourea, 22 g of ethyl bromopyruvate and 200 ml of ethanol, giving the title compound as a yellow oil.

Nuclear Magnetic Resonance Spectrum (CDCl$_3$) δ ppm: 1.0–2.3 (10H, multiplet), 1.37 (3H, triplet, J=7 Hz), 3.0–3.5 (1H, multiplet), 4.34 (2H, quartet. J=7 Hz), 5.1–5.6 (1H, multiplet), 7.41 (1H, singlet).

PREPARATION 73

2-Cyclohexylaminothiazol-4-ylmethanol

The reaction described in Preparation 15 was repeated, but using 19 g of ethyl 2-cyclohexylaminothiazole-4-carboxylate, 4.2 g of lithium aluminum hydride and 250 ml of tetrahydrofuran, giving the title compound as pale yellow needles.

Melting Point: 118° to 120° C.

Nuclear Magnetic Resonance Spectrum (CDCl$_3$) δ ppm: 1.0–2.2 (10H, multiplet), 2.9–3.5 (2H, not defined), 4.50 (2H, singlet), 5.0–5.5 (1H, broad), 6.33 (1H, singlet).

PREPARATION 74

2-Cyclohexylaminothiazole-4-carbaldehyde

The reaction described in Preparation 44 was repeated, but using 10 g of 2-cyclohexylaminothiazol-4-ylmethanol, 22.4 g of sulfur trioxide pyridine complex, 14.3 g of triethylamine and 100 ml of dimethyl sulfoxide, giving the title compound as a pale brown oil.

Nuclear Magnetic Resonance Spectrum (CDCl$_3$) δ ppm: 1.0–2.2 (10H, multiplet), 3.2–3.6 (1H. multiplet), 5.1–5.4 (1H, multiplet), 7.40 (1H, singlet), 9.72 (1H, singlet).

PREPARATION 75

Ethyl 2-diphenylaminothiazole-4-carboxylate

The reaction described in Preparation 42 was repeated, but using 20 g of 1,1-diphenylthiourea, 19 g of ethyl bromopyruvate and 200 ml of ethanol, giving the title compound as an orange oil.

Nuclear Magnetic Resonance Spectrum (CDCl$_3$) δ ppm: 1.36 (3H. triplet. J=7 Hz), 4.35 (2H, quartet, J=7 Hz), 7.1–7.5 (10H, multiplet), 7.54 (1H, singlet).

PREPARATION 76

2-Diphenylaminothiazol-4-ylmethanol

The reaction described in Preparation 15 was repeated, but using 27 g of ethyl 2-diphenylaminothiazole-4-carboxylate, 4.7 g of lithium aluminum hydride and 400 ml of tetrahydrofuran, giving the title compound as pale yellow prisms.

Melting Point: 136° to 138° C.

Nuclear Magnetic Resonance Spectrum (CDCl$_3$) δ ppm: 2.33 (1H, broad triplet, J=6 Hz). 4.56 (2H, broad doublet, J=6 Hz), 6.52 (1H, singlet), 7.1–7.5 (10H, multiplet).

PREPARATION 77

2-Diphenylaminothiazole-4-carbaldehyde

The reaction described in Preparation 44 was repeated, but using 10 g of 2-dimethylaminothiazol-4-ylmethanol, 16.8 g of sulfur trioxide pyridine complex, 10.7 g of triethylamine and 100 ml of dimethyl sulfoxide, giving the title compound as pale yellow prisms.

Melting Point: 160° to 161° C.

Nuclear Magnetic Resonance Spectrum (hexadeuterated dimethyl sulfoxide) δ ppm: 7.2–7.6 (10H, multiplet). 8.06 (1H, singlet), 9.70 (1H. singlet).

PREPARATION 78

Ethyl 2-morpholinothiazole-4-carboxylate

The reaction described in Preparation 26 was repeated, but using 1.4 g of morpholine, 3 g of ethyl 2-chlorothiazole-4-carboxylate. 3 g of triethylamine and 12 ml of dimethylformamide, giving the title compound as colorless needles.

Melting Point: 84° to 86° C.

Nuclear Magnetic Resonance Spectrum (CDCl$_3$) δ ppm: 1.37 (3H, triplet, J=7 Hz). 3.45–3.6 (4H, multiplet), 3.75–3.9 (4H, multiplet), 4.36 (2H, quartet, J=7 Hz). 7.50 (1H, singlet).

PREPARATION 79

2-Moroholinothiazol-4-ylmethanol

The reaction described in Preparation 15 was repeated, but using 3.7 g of ethyl 2-morpholinothiazole-4-carboxylate, 0.6 g of lithium aluminum hydride and 50 ml of tetrahydrofuran, giving the title compound as white needles.

Melting Point: 120° to 121° C.

Nuclear Magnetic Resonance Spectrum (CDCl$_3$) δ ppm: 2.40 (1H, triplet, J=6 Hz), 3.35–3.55 (4H, multiplet), 3.7–3.9 (4H, multiplet), 4.59 (2H, doublet, J=6 Hz), 6.47 (1H, singlet).

PREPARATION 80

2-Morpholinothiazole-4-carbaldehyde

The reaction described in Preparation 44 was repeated but using 2.4 g of 2-morpholinothiazol-4-ylmethanol, 5.7 g of sulfur trioxide pyridine complex. 3.6 g of triethylamine and 30 ml of dimethyl sulfoxide, giving the title compound as pale yellow needles.

Melting Point: 107° to 108° C.

Nuclear Magnetic Resonance Spectrum (CDCl$_3$) δ ppm: 3.45–3.65 (4H, multiplet), 3.75–3.9 (4H, multiplet), 7.51 (1H. singlet), 9.77 (1H. singlet).

PREPARATION 81

Ethyl 2-piperidinothiazole-4-carboxylate

A mixture comprising 2.1 g of piperidine, 4 g of ethyl 2-chlorothiazole-4-carboxylate, 4.2 g of triethylamine and 20 ml of benzene was refluxed for 12 hours. The reaction mixture was poured into water and extracted with benzene. The extract was washed with water, dried over anhydrous magnesium sulfate and concentrated under reduced pressure.

The residue was then purified by silica gel column chromatography. using as eluent a 10:1 mixture of benzene and ethyl acetate, giving the title compound as a pale yellow oil.

Nuclear Magnetic Resonance Spectrum (CDCl$_3$) δ ppm: 1.36 (3H, triplet, J=7 Hz), 1.5–1.9 (6H, multiplet), 3.3–3.7 (4H, multiplet), 4.35 (2H, quartet, J=7 Hz), 7.42 (1H, singlet).

PREPARATION 82

2-piperidinothiazol-4-yimethanol

The reaction described in Preparation 15 was repeated, but using 3.0 g of ethyl 2-piperidinothiazole-4-carboxylate, 0.5 g of lithium aluminum hydride and 50 ml of tetrahydrofuran, giving the title compound as pale yellow prisms.

Melting point: 89° to 90° C.

Nuclear Magnetic Resonance Spectrum (CDCl$_3$) δ ppm: 1.5–1.9 (6H, multiplet), 2.50 (1H, broad), 3.3–3.6 (4H. multiplet). 4.45–4.65 (2H broad doublet), 6.37 (1H, singlet).

PREPARATION 83

2-piperidinothiazole-4-carbaldehyde

The reaction described in Preparation 44 was repeated, but using 2.4 g of 2-piperidinothiazol-4-ylmethanol, 5.8 g of sulfur trioxide pyridine complex, 3.7 g of triethylamine and 30 ml of dimethyl sulfoxide, giving the title compound as pale orange prisms.

Melting Point: 68° to 69° C.

Nuclear Magnetic Resonance Spectrum (CDCl$_3$) δ ppm: 1.55–1.85 (6H, multiplet), 3.4–3.7 (4H, multiplet), 7.44 (1H, singlet), 9.75 (1H, singlet).

PREPARATION 84

Ethyl 2-(Thiomorpholin-4-yl)thiazole-4-carboxylate

The reaction described in Preparation 26 was repeated, but using 1.53 g of thiomorpholine, 2.36 g of ethyl 2-bromothiazole-4-carboxylate, 2.02 g of triethylamine and 40 ml of dimethylformamide, giving the title compound as a pale yellow powder.

Melting Point: 99° to 100° C.

Nuclear Magnetic Resonance Spectrum (CDCl$_3$) δ ppm: 1.37 (3H. triplet. J=7 Hz), 2.7–2.75 (4H, multiplet), 3.85–3.9 (4H. multiplet), 4.35 (2H. quartet. J=7 Hz), 7.44 (1H, singlet),

PREPARATION 85

2-(Thiomorpholin-4-yl)thiazol-4-ylmethanol

The reaction described in Preparation 15 was repeated, but using 1.5 g of ethyl 2-(thiomorpholin-4-yl)thiazole -4-carboxylate, 0.26 g of lithium aluminum hydride and 15 ml of tetrahydrofuran, giving the title compound as a colorless powder.

Melting Point: 83° to 84° C.

Nuclear Magnetic Resonance Spectrum (CDCl$_3$) δ ppm: 2.51 (1H, broad doublet, J=5 Hz, disappeared on adding deuterium oxide), 2.68–2.73 (4H, multiplet), 3.8–3.85 (4H, multiplet), 4.53 (2H, doublet, J=5 Hz, changed to 4.51 (2H, singlet) on adding deuterium oxide), 6.41 (1H. triplet, J=1 Hz).

PREPARATION 86

2-(Thiomorpholin-4-yl)thiazole-4-carbaldehyde

The reaction described in Preparation 44 was repeated, but using 1.2 g of 2-(thiomorpholin-4-yl)thiazol-4-ylmethanol, 2.65 g of sulfur trioxide pyridine complex, 1.68 g of triethylamine and 30 ml of dimethyl sulfoxide, giving the title compound as a colorless powder.

Melting Point: 69° to 71° C.

Nuclear Magnetic Resonance Spectrum (CDCl$_3$) δ ppm: 2.7–2.76 (4H multiplet), 3.85–3.93 (4H. multiplet). 7.47 (1H, singlet), 9.69 (1H, singlet).

PREPARATION 87

Ethyl 2-(4-Methyl-l-oiperazinyl)thiazole-4-carboxylate

The reaction described in Preparation 26 was repeated, but using 2.5 g of N-methylpiperazine, 4.0 g of ethyl 2-chlorothiazole-4-carboxylate, 4.2 g of triethylamine and 30 ml of toluene, giving the title compound as a pale yellow oil.

Nuclear Magnetic Resonance Spectrum (CDCl$_3$) δ ppm: 1.37 (3H. triplet J=7 Hz). 2.34 (3H, singlet), 2.51 (4H, broad triplet, J=6 Hz), 3.56 (4H, broad triplet, J=6 Hz), 4.35 (2H, quartet, J=7 Hz), 7.46 (1H, singlet).

PREPARATION 88

2-(4-Methyl-1-piperazinyl)thiazol-4-ylmethanol

The reaction described in Preparation 15 was repeated, but using 4.0 g of ethyl 2-(4-methyl-1-piperazinyl)-thiazole-4-carboxylate, 0.6 g of lithium aluminum hydride and 50 ml of tetrahydrofuran, giving the title compound as white prisms.

Melting Point: 103° to 105° C.

Nuclear Magnetic Resonance Spectrum (CDCl$_3$) δ ppm: 2.26 (3H, singlet), 2.43 (4H, broad triplet, J=5 Hz), 2.6–2.8 (1H, broad), 3.41 (4H, broad triplet, J=5 Hz), 4.47 (2H, singlet), 6.34 (1H, triplet, J=1 Hz),

PREPARATION 89

2-(4-Methyl-1-piperazinyl)thiazole-4-carbaldehyde

The reaction described in Preparation 44 was repeated, but using 2.4 g of 2-(4-methyl-1-piperazinyl)-thiazol-4-yl-methanol, 5.4 g of sulfur trioxide pyridine complex, 3.4 g of triethylamine, and 30 ml of dimethyl sulfoxide, giving the title compound as a pale brown oil.

Nuclear Magnetic Resonance Spectrum (CDCl$_3$) δ ppm: 2.35 (3H, singlet), 2.53 (4H, broad triplet, J=5 Hz), 3.59 (4H, broad triplet, J=5 Hz), 7.47 (1H, singlet), 9.70 (1H, singlet).

PREPARATION 90

Ethyl 2-octylaminothiazole-4-carboxylate

The reaction described in Preparation 26 was repeated, but using 2.7 g of octylamine, 4.0 g of ethyl 2-chlorothiazole-4-carboxylate, 4.2 g of triethylamine and 15 ml of dimethylformamide, giving the title compound as a pale yellow oil.

Nuclear Magnetic Resonance Spectrum (CDCl$_3$) δ ppm: 0.7–1.9 (18H, not defined), 3.0–3.4 (2H, multiplet), 4.36 (2H, quartet, J=7 Hz), 5.5–6.0 (1H, broad), 7.41 (1H, singlet).

PREPARATION 91

2-Octylaminothiazol-4-ylmethanol

The reaction described in preparabion 15 was repeated, but using 1.5 g of 2-octylaminothiazol-4-carboxylate, 0.2 g of lithium aluminum hydride and 30 ml of tetrahydrofuran, giving the title compound as a pale yellow oil.

Nuclear Magnetic Resonance Spectrum (CDCl$_3$) δ ppm: 0.88 (3H, broad triplet, J=7 Hz), 1.2–1.45 (10H, multiplet), 1.55–1.75 (2H, multiplet), 3.15–3.3 (2H, multiplet), 4.51 (2H, doublet, J=1 Hz), 5.26 (1H, broad singlet), 6.34 (1H, singlet).

PREPARATION 92

2-Octylaminothiazole-4-carbaldehyde

The reaction described in Preparation 44 was repeated, but using 1.3 g of 2-octylaminothiazol-4-ylmethanol, 2.6 g of pyridine sulfur trioxide complex, 1.6 g of triethylamine and 20 ml of dimethyl sulfoxide. giving the title compound as pale brown needles.

Melting Point: 60° to 62° C.

Nuclear Magnetic Resonance Spectrum (CDCl$_3$) δ ppm: 0.7–1.9 (15H, multiplet), 3.1–3.6 (2H, multiplet), 5.9–6.3 (1H, broad), 7.41 (1H, singlet), 9.72 (1H, singlet).

PREPARATION 93

Ethyl 2-isopropylaminothiazole-4-carboxylate

The reaction described in Preparation 42 was repeated, but using 3.7 g of isopropylthiourea, 7.4 g of ethyl bromopyruvate and 50 ml of ethanol, giving the title compound as a pale yellow oil.

Nuclear Magnetic Resonance Spectrum (CDCl$_3$) δ ppm: 1.29 (6H. doublet, J=7 Hz), 1.37 (3H, triplet. J=7 Hz), 3.35–3.85 (1H. multiplet), 4.35 (2H. quartet, J=7 Hz). 5.0–5.7 (1H, broad), 7.42 (1H. singlet).

PREPARATION 94

2-Isopropylaminothiazol-4-ylmethanol

The reaction described in Preparation 15 was repeated, but using 6.8 g of ethyl 2-isopropylaminothiazole-4-carboxylate. 1.2 g of lithium aluminum hydride and 100 ml of tetrahydrofuran, giving the title compound as a pale yellow oil.

Nuclear Magnetic Resonance Spectrum (CDCl$_3$) δ ppm: 2.27 (6H, doublet. J=7 Hz), 3.4–3.9 (1H, multiplet), 4.51 (2H, singlet). 4.8–5.3 (1H, broad), 6.34 (1H, singlet).

PREPARATION 95

2-Isopropylaminothiazole-4-carbaldehyde

The reaction described in Preparation 44 was repeated, but using 4.4 q of 2-isopropylaminothiazol-4-ylmethanol, 12.2 g of pyridine sulfur trioxide complex, 7.7 g of triethylamine and 60 ml of dimethyl sulfoxide, giving the title compound as a pale brown oil.

Nuclear Magnetic Resonance Spectrum (CDCl$_3$) δ ppm: 2.31 (6H, doublet, J=7 Hz), 3.55–4.0 (1H, multiplet), 5.1–5.5 (1H, broad), 7.41 (1H, singlet), 9.74 (1H. singlet).

PREPARATION 96

Ethyl 2-benzylaminothiazole-4-carboxylate

The reaction described in Preparation 42 was repeated, but using 5.02 g of benzylthiourea, 5.87 g of ethyl bromopyruvate and 50 ml of ethanol, giving the title compound as pale yellow needles.

Melting Point: 132° to 136° C.

Nuclear Magnetic Resonance Spectrum (hexadeuterated dimethyl sulfoxide) δ ppm: 1.27 (3H, triplet, J=7 Hz), 4.22 (2H, quartet, J=7 Hz), 4.47 (2H, doublet, J=6 Hz), 7.1–7.6 (5H, multiplet), 7.53 (1H, singlet), 8.30 (1H, broad triplet, J=6 Hz),

PREPARATION 97

2-Benzylaminothiazol-4-ylmethanol

The reaction described in Preparation 15 was repeated, but using 5 g of ethyl 2-benzylaminothiazole-4-carboxylate, 1.4 g of lithium aluminum hydride and 100 ml of tetrahydrofuran, giving the title compound as colorless needles.

Melting Point: 85° to 86.5° C.

Nuclear Magnetic Resonance Spectrum (hexadeuterated acetone) δ ppm: 3.7–4.1 (1H, broad), 4.44 (2H, broad singlet), 4.54 (2H, broad singlet), 6.38 (1H. singlet), 6.9–7.3 (1H, broad), 7.2–7.4 (5H, multiplet).

PREPARATION 98

2-Benzylaminothiazole-4-carbaldehyde

The reaction described in Preparation 44 was repeated, but using 1.21 g of 2-benzylaminothiazol-4-ylmethanol, 2.6 g of pyridine sulfur trioxide complex, 3 ml of triethylamine and 30 ml of dimethyl sulfoxide, giving the title compound as pale brown crystals.

Melting point: 162° to 165° C.

Nuclear Magnetic Resonance Spectrum (hexadeuterated acetone) δ ppm: 4.44 (2H, broad doublet, J=5 Hz), 7.2–7.5 (5H, multiplet), 7.5–7.9 (1H, broad), 7.65 (1H, singlet), 9.71 (1H, singlet).

PREPARATION 99

Sodium 2-(3-benzoylthioureido)thiazol-4-ylglyoxylate

A mixture comprising 2.0 g of ethyl 2-(3-benzoylthioureido)thiazol-4-ylglyoxylate, 2.3 g of potassium carbonate, 100 ml of acetone. 100 ml of methanol and 20 ml of water was stirred for 50 minutes at 60 ° C. after which the solvent was evaporated off under reduced pressure. Ethyl acetate and brine were added to the residue, giving the crude title compound as a yellow powder.

Melting point: 223° to 226° C.

Nuclear Magnetic Resonance Spectrum (hexadeuterated dimethyl sulfoxide) δ ppm: 7.35–7.6 (3H, multiplet), 7.70 (1H, singlet), 7.92 (2H, broad doublet, J=7 Hz), 9.4–10.0 (1H, broad, disappeared on adding deuterium oxide).

PREPARATION 100

Ethyl 2-cyclopropylaminothiazole-4-carboxylate

The reaction described in Preparation 26 was repeated, except that a mixture comprising 2.28 g of cyclopropylamine, 5.0 g of ethyl 2-bromothiazole-4-carboxylate and 20 ml of toluene was heated at 100°–110 ° C. for 16 hours in a sealed tube, giving the title compound as a pale yellow oil.

Nuclear Magnetic Resonance Spectrum (CDCl3) δ ppm: 0.5–0.9 (4H, multiplet), 1.37 (3H, triplet, J=7 Hz), 2.45–2.75 (1H, multiplet), 4.36 (2H, quartet, J=7 Hz), 5.8–6.1 (1H, broad), 7.48 (1H, singlet).

PREPARATION 101

2-Cyclopropylaminothiazol-4-ylmethanol

The reaction described in Preparation 15 was repeated, but using 1.2 g of ethyl 2-cyclopropylaminothiazole- 4-carboxylate, 0.2 g of lithium aluminum hydride and 20 ml of tetrahydrofuran, giving the title compound as a pale yellow oil.

Nuclear Magnetic Resonance Spectrum (CDCl3) δ ppm: 0.5–1.0 (4H, multiplet), 2.45–2.7 (1H, multiplet), 3.1–4.0 (1H, broad), 4.53 (2H, singlet), 5.9–6.7 (1H, broad), 6.42 (1H, singlet).

PREPARATION 102

2-Cyclopropylaminothiazole-4-carbaldehyde

The reaction described in Preparation 44 was repeated, but using 1.1 g of 2-cyclopropylaminothiazol-4-ylmethanol, 3.1 g of sulfur trioxide pyridine complex, 2 g of triethylamine and 15 ml of dimethyl sulfoxide, giving the title compound as pale yellow prisms.

Melting point: 124° to 127 ° C.

Nuclear Magnetic Resonance Spectrum (CDCl3) δ ppm: 0.6–1.0 (4H, multiplet), 1.55–1.8 (1H, multiplet), 6.7–7.3 (1H, broad), 7.48 (1H, singlet), 9.76 (1H, singlet).

We claim:

1. A compound of formula (I):

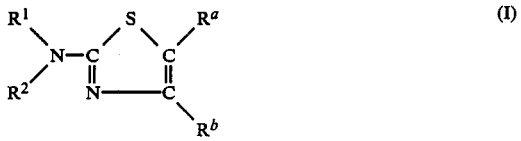

in which:
R$^1$ and R$^2$ are independently selected from the group consisting of:
hydrogen atoms,
C$_1$–C$_{12}$ alkyl groups,
C$_3$–C$_6$ aliphatic hydrocarbon groups having one or two carbon-carbon double or treble bonds,
C$_3$–C$_8$ cycloalkyl groups,
C$_6$–C$_{14}$ aryl groups,
substituted C$_6$–C$_{14}$ aryl groups having at least one substituent selected from the group consisting of substituents (a) defined below,
aralkyl and substituted aralkyl groups with from 1 to 3 aryl parts each of which is C$_6$–C$_{14}$ and an alkyl part which is C$_1$–C$_5$, and said substituted aralkyl groups having at least one substituent selected from the group consisting of substituents (a) defined below,
C$_1$–C$_{12}$ alkanoyl groups.
C$_3$–C$_{12}$ alkenoyl groups,
C$_4$–C$_9$ cycloalkylcarbonyl groups,
C$_7$–C$_{15}$ arylcarbonyl groups,
substituted C$_7$–C$_{15}$ arylcarbonyl groups having at least one substituent selected from the group consisting of substituents (a) defined below,
arylalkanoyl groups in which the aryl part is C$_6$–C$_{14}$ and is unsubstituted or has at least one substituent selected from the group consisting of substituents (a) defined below and the alkanoyl part is $C_2$–$C_6$, arylalkenoyl groups in which the aryl part is $C_6$–$C_{14}$ and is unsubstituted or has at least one substituent selected from the group consisting of substituents (a) defined below and the alkenoyl part is $C_3$–$C_6$, $C_2$–$C_7$ alkoxycarbonyl groups, $C_7$–$C_{15}$ aryloxycarbonyl groups, substituted $C_7$–$C_{15}$ aryloxycarbonyl groups having at least one substituent selected from the group consisting of substituents (a) defined below, $C_8$–$C_{20}$ aralkyloxycarbonyl groups, substituted $C_8$–$C_{20}$ aralkyloxycarbonyl groups having at least one substituent selected from the group consisting of substituents (a) defined below, groups of formula —$CONR^6R^7$, groups of formula —$CSNR^6R^7$, $C_1$–$C_6$ alkylsulfonyl groups, $C_1$–$C_6$ haloalkylsulfonyl groups, $C_6$–$C_{14}$ arylsulfonyl groups, substituted $C_6$–$C_{14}$ arylsulfonyl groups having at least one substituent selected from the group consisting of substituents (a) defined below, $C_1$–$C_6$ alkylthio groups, $C_6$–$C_{14}$ arylthio groups and substituted $C_6$–$C_{14}$ arylthio groups having at least one substituent selected from the group consisting of substituents (a) defined below;

or $R^1$ and $R^2$, together with the nitrogen atom to which they are attached, form a nitrogen-containing heterocyclic group having from 5 to 8 ring atoms, of which 0 or 1 is an additional hetero-atom selected from the group consisting of nitrogen, oxygen and sulfur hetero-atoms, said heterocyclic group being unsubstituted or having at least one substituent selected from the group consisting of substituents (b) defined below, or form such a heterocyclic group fused to at least one benzene or naphthalene ring system which ring system is unsubstituted or has at least one substituent selected from the group consisting of substituents (c) defined below;

one of $R^a$ and $R^b$ represents a hydrogen atom, a $C_1$–$C_6$ alkyl group or a halogen atom, and the other of $R^a$ and $R^b$ represents a group of formula (II):

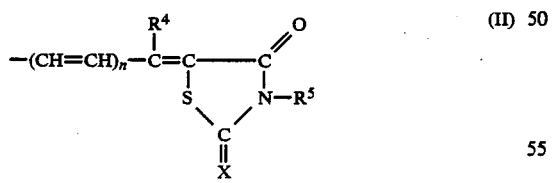

$R^4$ represents a hydrogen atom, a carboxy group, a protected carboxy group or a group of formula —$CONR^8R^9$;

$R^5$ represents a hydrogen atom, or a carboxyalkyl or protected carboxyalkyl group in which the alkyl part is $C_1$–$C_6$;

n=0, 1 or 2;

X represents an oxygen or sulfur atom;

$R^6$ and $R^7$ are independently selected from the group consisting of:

hydrogen atoms, $C_1$–$C_6$ alkyl groups, $C_3$–$C_6$ alkenyl groups, $C_3$–$C_8$ cycloalkyl groups, $C_6$–$C_{14}$ aryl groups, substituted $C_6$–$C_{14}$ aryl groups having at least one substituent selected from the group consisting of substituents (c) defined below, $C_7$–$C_{19}$ aralkyl groups, substituted $C_7$–$C_{19}$ aralkyl groups having at least one substituent selected from the group consisting of substituents (c) defined below, $C_1$–$C_6$ alkylsulfonyl groups, $C_1$–$C_6$ haloalkylsulfonyl groups, $C_6$–$C_{14}$ arylsulfonyl groups, substituted $C_6$–$C_{14}$ arylsulfonyl groups having at least one substituent selected from the group consisting of substituents (c) defined below, $C_1$–$C_{12}$ alkanoyl groups, $C_4$–$C_9$ cycloalkylcarbonyl groups, $C_7$–$C_{15}$ arylcarbonyl groups, substituted $C_7$–$C_{15}$ arylcarbonyl groups having at least one substituent selected from the group consisting of substituents (c) defined below;

$R^8$ and $R^9$ are independently selected from the group consisting of hydrogen atoms and $C_1$–$C_6$ alkyl groups;

substituents (a):

$C_1$–$C_8$ alkyl groups, $C_1$–$C_6$ haloalkyl groups, $C_6$–$C_{14}$ aryl groups, $C_7$–$C_{19}$ aralkyl groups, $C_1$–$C_{12}$ alkanoyl groups, $C_7$–$C_{15}$ arylcarbonyl groups, $C_2$–$C_7$ alkoxycarbonyl groups, $C_7$–$C_{15}$ aryloxycarbonyl groups, $C_8$–$C_{20}$ aralkyloxycarbonyl groups, groups of formula —$CONR^{10}R^{11}$, groups of formula —$CSNR^{10}R^{11}$, (where $R^{10}$ and $R^{11}$ are independently selected from the group consisting of hydrogen atoms, $C_1$–$C_6$ alkyl groups and $C_6$–$C_{14}$ aryl groups), groups of formula —$NR^{12}R^{13}$, (where $R^{12}$ and $R^{13}$ are independently selected from the group consisting of hydrogen atoms, $C_1$–$C_6$ alkyl groups, $C_6$–$C_{14}$ aryl groups, $C_1$–$C_6$ alkanoyl groups and $C_7$–$C_{15}$ arylcarbonyl groups), halogen atoms, nitro groups, cyano groups, hydroxy groups, $C_1$–$C_6$ alkoxy groups, $C_6$–$C_{14}$ aryloxy groups, $C_1$–$C_{12}$ alkanoyloxy groups, $C_7$–$C_{15}$ arylcarbonyloxy groups, $C_2$–$C_7$ alkoxycarbonyloxy groups, $C_7$–$C_{15}$ aryloxycarbonyloxy groups, $C_8$–$C_{20}$ aralkyloxycarbonyloxy groups, carboxy groups, sulfo groups, and sulfamoyl groups;

substituents (b):

oxygen atoms, halogen atoms, $C_1$–$C_6$ alkyl groups, $C_6$–$C_{14}$ aryl groups, substituted $C_6$–$C_{14}$ aryl groups having at least one substituent selected from the group consisting of substituents (c) defined below, $C_7$-$C_{19}$ aralkyl groups,
substituted $C_7$-$C_{19}$ aralkyl groups having at least one substituent selected from the group consisting of substituents (c) defined below,
$C_1$-$C_6$ alkanoyl groups,
$C_7$-$C_{15}$ arylcarbonyl groups and
substituted $C_7$-$C_{15}$ arylcarbonyl groups having at least one substituent selected from the group consisting of substituents (c) defined below;
substituents (c):
$C_1$-$C_4$ alkyl groups,
$C_1$-$C_4$ alkoxy groups,
$C_6$-$C_{10}$ aryl groups,
$C_6$-$C_{10}$ aryloxy groups,
$C_1$-$C_6$ alkanoyloxy groups,
halogen atoms,
hydroxy groups,
cyano groups,
trifluoromethyl groups,
carboxy groups, and
nitro groups;
and pharmaceutically acceptable salts and esters thereof.

2. The compound of claim 1, wherein:
$R^1$ and $R^2$ are independently selected from the group consisting of:
hydrogen atoms,
$C_1$-$C_8$ alkyl groups,
$C_3$-$C_6$ alkenyl groups,
$C_3$-$C_8$ cycloalkyl groups,
$C_6$-$C_{14}$ aryl groups,
substituted $C_6$-$C_{14}$ aryl groups having at least one substituent selected from the group consisting of substituents ($a^1$) defined below,
aralkyl and substituted aralkyl groups with from 1 to 3 aryl parts each of which is $C_6$-$C_{10}$ and an alkyl part which is $C_1$-$C_3$, and said substituted aralkyl groups having at least one substituent selected from the group consisting of substituents ($a^1$) defined below,
$C_1$-$C_6$ alkanoyl groups,
benzoyl groups,
substituted benzoyl groups having at least one substituent selected from the group consisting of substituents ($a^1$) defined below,
$C_2$-$C_7$ alkoxycarbonyl groups,
groups of formula —CONR$^{6'}$R$^{7'}$,
groups of formula —CSNR$^{6'}$R$^{7'}$,
benzenesulfonyl groups, and
toluenesulfonyl groups,
or $R^1$ and $R^2$, together with the nitrogen atom to which they are attached, form a nitrogen-containing heterocyclic group having 5 or 6 ring atoms, of which 0 or 1 is an additional hetero-atom selected from the group consisting of nitrogen, oxygen and sulfur hetero-atoms, said heterocyclic group being unsubstituted or having at least one substituent selected from the group consisting of substituents ($b^1$) defined below, or form such a heterocyclic group fused to at least one benzene ring system which ring system is unsubstituted or has at least one substituent selected from the group consisting of substituents ($c^1$) defined below;
$R^{6'}$ and $R^{7'}$ are independently selected from the group consisting of:
hydrogen atoms,
$C_1$-$C_6$ alkyl groups,
$C_3$-$C_6$ alkenyl groups,
$C_3$-$C_8$ cycloalkyl groups,
$C_6$-$C_{14}$ aryl groups,
benzyl groups,
substituted $C_6$-$C_{14}$ aryl groups having at least one substituent selected from the group consisting of substituents ($c^1$) defined below,
benzenesulfonyl groups,
toluenesulfonyl groups,
$C_2$-$C_6$ alkanoyl groups, and
$C_7$-$C_{11}$ arylcarbonyl groups,
substituents ($a^1$):
$C_1$-$C_6$ alkyl groups,
trifluoromethyl groups,
$C_6$-$C_{10}$ aryl groups,
$C_7$-$C_{12}$ aralkyl groups,
$C_1$-$C_6$ alkanoyl groups,
$C_7$-$C_{11}$ arylcarbonyl groups,
$C_2$-$C_7$ alkoxycarbonyl groups,
groups of formula —CONR$^{10'}$R$^{11'}$,
groups of formula —CSNR$^{10'}$R$^{11'}$, (where $R^{10'}$ and $R^{11'}$ are independently selected from the group consisting of hydrogen atoms, $C_1$-$C_6$ alkyl groups and $C_6$-$C_{10}$ aryl groups),
groups of formula —NR$^{12'}$R$^{13'}$, (where $R^{12'}$ and $R^{13'}$ are independently selected from the group consisting of hydrogen atoms, $C_1$-$C_6$ alkyl groups, phenyl groups, $C_1$-$C_6$ alkanoyl groups and benzoyl groups),
halogen atoms,
nitro groups,
cyano groups,
hydroxy groups,
$C_1$-$C_6$ alkoxy groups,
phenoxy groups,
$C_1$-$C_6$ alkanoyloxy groups,
benzoyloxy groups,
$C_2$-$C_7$ alkoxycarbonyloxy groups, and
carboxy groups;
substituents ($b^1$):
oxygen atoms,
$C_1$-$C_4$ alkyl groups,
phenyl groups,
benzyl groups,
$C_1$-$C_6$ alkanoyl groups, and
benzoyl groups;
substituents ($c^1$):
$C_1$-$C_4$ alkyl groups,
$C_1$-$C_4$ alkoxy groups,
halogen atoms,
trifluoromethyl groups, and
nitro groups.

3. The compound of claim 1, wherein one of $R^a$ and $R^b$ represents a hydrogen atom, and the other of $R^a$ and $R^b$ represents a group of formula (II), defined in claim 1.

4. The compound of claim 1, wherein $R^4$ represents a hydrogen atom, a $C_2$-$C_5$ alkoxycarbonyl group or a benzyloxycarbonyl group.

5. The compound of claim 1, wherein $R^5$ represents a hydrogen atom, a carboxymethyl group or a protected carboxymethyl group, in which the protecting group is a $C_1$-$C_4$ alkyl group, a benzyl group or a group capable of being hydrolyzed in vivo.

6. The compound of claim 1, wherein n=0 or 1.

7. The compound of claim 1, wherein X represents a sulfur atom.

8. The compound of claim 1, wherein $R^a$ represents a hydrogen atom and $R^b$ represents a group of formula (II), as defined in claim 1.

9. The compound of claim 1, wherein:
R$^1$ and R$^2$ are independently selected from the group consisting of:
hydrogen atoms,
C$_1$–C$_8$ alkyl groups,
C$_3$–C$_6$ alkenyl groups,
C$_3$–C$_8$ cycloalkyl groups,
C$_6$–C$_{14}$ aryl groups,
substituted C$_6$–C$_{14}$ aryl groups having at least one substituent selected from the group consisting of substituents (a$^1$) defined below,
aralkyl and substituted aralkyl groups with from 1 to 3 aryl parts each of which is C$_6$–C$_{10}$ and an alkyl part which is C$_1$–C$_3$, and said substituted aralkyl groups having at least one substituent selected from the group consisting of substituents (a$^1$) defined below,
C$_1$–C$_6$ alkanoyl groups,
benzoyl groups,
substituted benzoyl groups having at least one substituent selected from the group consisting of substituents (a$^1$) defined below.
C$_2$–C$_7$ alkoxycarbonyl groups,
groups of formula —CONR$^{6'}$R$^{7'}$,
groups of formula —CSNR$^{6'}$R$^{7'}$,
benzenesulfonyl groups, and
toluenesulfonyl groups,
or R$^1$ and R$^2$, together with the nitrogen atom to which they are attached, form a nitrogen-containing heterocyclic group having 5 or 6 ring atoms, of which 0 or 1 is an additional hetero-atom selected from the group consisting of nitrogen, oxygen and sulfur hetero-atoms, said heterocyclic group being unsubstituted or having at least one substituent selected from the group consisting of substituents (b$^1$I) defined below, or form such a heterocyclic group fused to at least one benzene ring system which ring system is unsubstituted or has at least one substituent selected from the group consisting of substituents (c$^1$) defined below;
one of R$^a$ and R$^b$ represents a hydrogen atom, and the other of R$^a$ and R$^b$ represents a group of formula (II), defined in claim 1;
R$^4$ represents a hydrogen atom, a C$_2$–C$_5$ alkoxycarbonyl group or a benzyloxycarbonyl group;
R$^5$ represents a hydrogen atom, a carboxymethyl group or a protected carboxymethyl group, in which the protecting group is a C$_1$–C$_4$ alkyl group, a benzyl group or a group capable of being hydrolyzed in vivo;
n=0 or 1;
X represents a sulfur atom;
R$^{6'}$ and R$^{7'}$ are independently selected from the group consisting of:
hydrogen atoms,
C$_1$–C$_6$ alkyl groups.
C$_3$–C$_6$ alkenyl groups,
C$_3$–C$_8$ cycloalkyl groups,
C$_6$–C$_{14}$ aryl groups,
substituted C$_6$–C$_{14}$ aryl groups having at least one substituent selected from the group consisting of substituents (c$^1$) defined below,
benzyl groups,
benzenesulfonyl groups,
toluenesulfonyl groups,
C$_2$–C$_6$ alkanoyl groups, and
C$_7$–C$_{11}$ arylcarbonyl groups,
substituents (a$^1$):
C$_1$–C$_6$ alkyl groups,
trifluoromethyl groups,
C$_6$–C$_{10}$ aryl groups,
C$_7$–C$_{12}$ aralkyl groups,
C$_1$–C$_6$ alkanoyl groups,
C$_7$–C$_{11}$ arylcarbonyl groups,
C$_2$–C$_7$ alkoxycarbonyl groups,
groups of formula —CONR$^{10'}$R$^{11'}$,
groups of formula —CSNR$^{10'}$R$^{11'}$, (where R$^{10'}$ and R$^{11'}$ are independently selected from the group consisting of hydrogen atoms, C$_1$–C$_6$ alkyl groups and C$_6$–C$_{10}$ aryl groups),
groups of formula —NR$^{12'}$R$^{13'}$, (where R$^{12'}$ and R$^{13'}$ are independently selected from the group consisting of hydrogen atoms, C$_1$–C$_6$ alkyl groups, phenyl groups, C$_1$–C$_6$ alkanoyl groups and benzoyl groups),
halogen atoms,
nitro groups,
cyano groups,
hydroxy groups,
C$_1$–C$_6$ alkoxy groups,
phenoxy groups,
C$_1$–C$_6$ alkanoyloxy groups,
benzoyloxy groups,
C$_2$–C$_7$ alkoxycarbonyloxy groups, and carboxy groups;
substituents (b$^1$):
oxygen atoms,
C$_1$–C$_4$ alkyl groups,
phenyl groups,
benzyl groups,
C$_1$–C$_6$ alkanoyl groups, and
benzoyl groups;
substituents (c$^1$):
C$_1$–C$_4$ alkyl groups,
C$_1$–C$_4$ alkoxy groups,
halogen atoms,
trifluoromethyl groups, and
nitro groups;
provided that, when R$^1$ represents said alkanoyl, benzoyl, substituted benzoyl, alkoxycarbonyl, benzenesulfonyl or toluenesulfonyl group or said group of formula —CONR$^{6'}$R$^{7'}$ or —CSNR$^{6'}$R$^{7'}$, then R$^2$ represents said hydrogen atom or said alkyl, alkenyl, cycloalkyl, aryl, substituted aryl, aralkyl or substituted aralkyl group.

10. The compound of claim 1, which is represented by the formula (Ia):

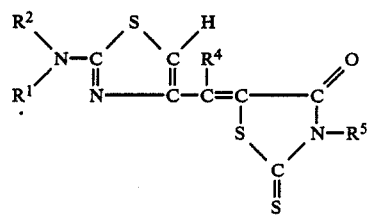

in which:
R$^1$ and R$^2$ are independently selected from the group consisting of:
hydrogen atoms,
C$_1$–C$_6$ alkyl groups,
C$_3$–C$_6$ alkenyl groups.
C$_3$–C$_6$ cycloalkyl groups,
phenyl groups, naphthyl groups,
substituted phenyl groups and substituted naphthyl groups having at least one substituent selected from the group consisting of substituents ($a^2$) defined below,
$C_2$–$C_6$ alkanoyl groups,
$C_7$–$C_{19}$ aralkyl groups,
$C_7$–$C_{19}$ substituted aralkyl groups having at least one substituent selected from the group consisting of substituents ($a^2$) defined below,
benzoyl groups,
substituted benzoyl groups having at least one substituent selected from the group consisting of substituents ($a^2$) defined below,
groups of formula —$CONR^{6''}R^{7''}$, and
groups of formula —$CSNR^{6''}R^{7''}$,
or $R^1$ and $R^2$, together with the nitrogen atom to which they are attached form a 1-pyrrolidinyl, piperidino hexamethyleneimino, morpholino, thiomorpholino or 1-piperazinyl group which is unsubstituted or has at least one substituent selected from the group consisting of substituents ($b^2$) defined below;
$R^4$ represents a hydrogen atom or a $C_2$–$C_5$ alkoxycarbonyl group;
$R^5$ represents a hydrogen atom, a carboxymethyl group or a protected carboxymethyl group, in which the protecting group is a $C_1$–$C_4$ alkyl group, a benzyl group or a group capable of being hydrolyzed in vivo;
$R^{6''}$ and $R^{7''}$ are independently selected from the group consisting of:
hydrogen atoms,
$C_1$–$C_6$ alkyl groups,
allyl groups.
cyclohexyl groups,
$C_6$–$C_{10}$ aryl groups,
substituted $C_6$–$C_{10}$ aryl groups having at least one substituent selected from the group consisting of substituents ($c^2$) defined below,
benzenesulfonyl groups,
toluenesulfonyl groups, and
benzoyl groups,
substituents ($a^2$):
$C_1$–$C_6$ alkyl groups,
trifluoromethyl groups,
phenyl groups,
halogen atoms, and
$C_1$–$C_6$ alkoxy groups;
substituents ($b^2$):
$C_1$–$C_4$ alkyl groups,
phenyl groups,
benzyl groups,
$C_1$–$C_6$ alkanoyl groups, and
benzoyl groups;
substituents ($c^2$):
$C_1$–$C_4$ alkyl groups,
$C_1$–$C_4$ alkoxy groups,
halogen atoms,
nitro groups, and
trifluoromethyl groups;
provided that, when $R^1$ represents a hydrogen atom then $R^2$ represents a group other than a hydrogen atom, and, when $R^1$ represents said alkanoyl, benzoyl or substituted benzoyl group or said group of formula —$CONR^{6''}R^{7''}$ or —$CSNR^{6''}R^{7''}$, then $R^2$ represents said hydrogen atom or said alkyl, alkenyl, cycloalkyl, phenyl, naphthyl, substituted phenyl, substituted naphthyl, aralkyl or substituted aralkyl group;
and pharmaceutically acceptable salts and esters thereof.

11. The compound of claim 10, wherein:
$R^1$ and $R^2$ are independently selected from the group consisting of:
hydrogen atoms,
$C_1$–$C_4$ alkyl groups,
$C_3$–$C_6$ alkenyl groups,
$C_3$–$C_6$ cycloalkyl groups,
phenyl groups,
substituted phenyl groups having at least one substituent selected from the group consisting of $C_1$–$C_4$ alkyl groups, $C_1$–$C_4$ alkoxy groups, halogen atoms and trifluoromethyl groups,
monoarylcarbamoyl and monoaryl(thiocarbamoyl) groups in which the aryl group is a $C_6$–$C_{10}$ carbocyclic aryl group which is unsubstituted or has at least one substituent selected from the group consisting of $C_1$–$C_4$ alkyl groups, $C_1$–$C_4$ alkoxy groups, halogen atoms, trifluoromethyl groups and nitro groups,
$R^4$ represents a hydrogen atom or a $C_2$–$C_5$ alkoxycarbonyl group;
$R^5$ represents a hydrogen atom, a carboxymethyl group or a protected carboxymethyl group, in which the protecting group is a $C_1$–$C_4$ alkyl group, a benzyl group or a group capable of being hydrolyzed in vivo;
provided that, when $R^1$ represents a hydrogen atom then $R^2$ represents a group other than a hydrogen atom, and, when $R^1$ represents said monoarylcarbamoyl or monoaryl(thiocarbamoyl) group, then $R^2$ represents said hydrogen atom or said alkyl, alkenyl, phenyl or substituted phenyl group;
and pharmaceutically acceptable salts and esters thereof.

12. The compound of claim 10, which is represented by the formula (Ib):

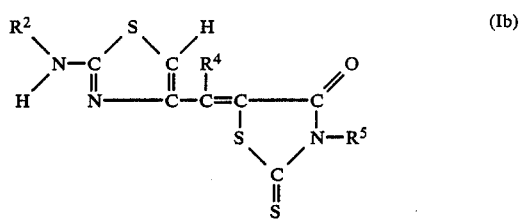

in which:
$R^2$ represents a $C_1$–$C_4$ alkyl group, a $C_3$–$C_6$ alkenyl group, a phenyl group, a substituted phenyl group having at least one substituent selected from the group consisting of $C_1$–$C_4$ alkyl groups, $C_1$–$C_4$ alkoxy groups, halogen atoms and trifluoromethyl groups, a phenylcarbamoyl group or a phenyl(thiocarbamoyl) group in which the phenyl group is unsubstituted or has at least one substituent selected from the group consisting of $C_1$–$C_4$ alkyl groups, $C_1$–$C_4$ alkoxy groups, halogen atoms, trifluoromethyl groups and nitro groups,
$R^4$ represents a hydrogen atom or a $C_2$–$C_5$ alkoxycarbonyl group;
$R^5$ represents a carboxymethyl group;
and pharmaceutically acceptable salts and esters thereof.

13. The compound of claim 1, selected from the group consisting of 5-{1-ethoxycarbonyl-1-[2-(3-phenylureido)thiazol-4-yl]methylene}rhodanine-3-acetic acid and pharmaceutically acceptable salts and esters thereof.

14. The compound of claim 1, selected from the group consisting of 5-[2-(3-phenylureido)thiazol-4-ylmethylene]rhodanine-3-acetic acid and pharmaceutically acceptable salts and esters thereof.

15. The compound of claim 1, selected from the group consisting of 5-{1-ethoxycarbonyl-1-[2-[3-(1-naphthyl)ureido]thiazol-4-yl]methylene}rhodanine-3-acetic acid and pharmaceutically acceptable salts and esters thereof.

16. The compound of claim 1, selected from the group consisting of 5-[1-[2-(3-p-chlorophenylureido)-thiazol-4yl]-1-ethoxycarbonylmethylene}rhodanine-3-acetic acid and pharmaceutically acceptable salts and esters thereof.

17. The compound of claim 1, selected from the group consisting of 5-[1-[2-(3-p-fluorophenylureido)-thiazol-4-yl]-1-ethoxycarbonylmethylene}rhodanine-3-acetic acid and pharmaceutically acceptable salts and esters thereof.

18. The compound of claim 1, selected from the group consisting of 5-{1-ethoxycarbonyl-1-[2-[3-(4-fluoro-3nitrophenyl)ureido]thiazol-4-yl]methylene}rhodanine-3acetic acid and pharmaceutically acceptable salts and esters thereof.

19. The compound of claim 1, selected from the group consisting of 5-{1-ethoxycarbonyl-1-[2-[3-(2,4,6-trifluorophenyl)ureido]thiazol-4-yl]methylene}rhodanine-3acetic acid and pharmaceutically acceptable salts and esters thereof.

20. The compound of claim 1, selected from the group consisting of 5-{1-ethoxycarbonyl-1-[2-(3-phenylthioureido)thiazol-4-yl]methylene}rhodanine-3-acetic acid and pharmaceutically acceptable salts and esters thereof.

21. The compound of claim 1 selected from the group consisting of 5-{1-[2-(3-p-chlorophenylthioureido)-thiazol-4-yl]-1-ethoxycarbonylmethylene}rhodanine-3-acetic acid and pharmaceutically acceptable salts and esters thereof.

22. The compound of claim 1, selected from the group consisting of 5-(2-ethylaminothiazol-4-ylmethylene)rhodanine-3-acetic acid and pharmaceutically acceptable salts and esters thereof.

23. The compound of claim 1, selected from the group consisting of 5-(2-isopropylaminothiazol-4-ylmethylene)rhodanine-3-acetic acid and pharmaceutically acceptable salts and esters thereof.

24. The compound of claim 1, selected from the group consisting of 5-(2-allylaminothiazol-4-ylmethylene)rhodanine-3-acetic acid and pharmaceutically acceptable salts and esters thereof.

25. The compound of claim 1, selected from the group consisting of 5-(2-cyclopropylaminothiazol-4-ylmethylene)rhodanine-3-acetic acid and pharmaceutically acceptable salts and esters thereof.

26. A pharmaceutical composition for the treatment or prevention of complications of diabetes, which comprises at least one active compound in admixture with a pharmaceutically acceptable carrier or diluent wherein said active compound is a compound of formula (I):

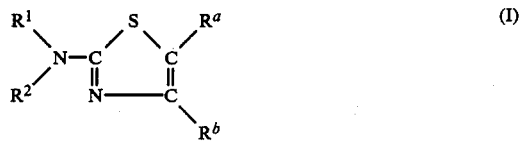

in which:
$R^1$ and $R^2$ are independently selected from the group consisting of:
hydrogen atoms,
$C_1$–$C_{12}$ alkyl groups,
$C_3$–$C_6$ aliphatic hydrocarbon groups having one or two carbon-carbon double or treble bonds,
$C_3$–$C_8$ cycloalkyl groups,
$C_6$–$C_{14}$ aryl groups,
substituted $C_6$–$C_{14}$ aryl groups having at least one substituent selected from the group consisting of substituents (a) defined below,
aralkyl and substituted aralkyl groups with from 1 to 3 aryl parts each of which is $C_6$–$C_{14}$ and an alkyl part which is $C_1$–$C_5$, and said substituted aralkyl groups having at least one substituent selected from the group consisting of substituents (a) defined below,
$C_1$–$C_{12}$ alkanoyl groups,
$C_3$–$C_{12}$ alkenoyl groups,
$C_4$–$C_9$ cycloalkylcarbonyl groups,
$C_7$–$C_{15}$ arylcarbonyl groups,
substituted $C_7$–$C_{15}$ arylcarbonyl groups having at least one substituent selected from the group consisting of substituents (a) defined below,
arylalkanoyl groups in which the aryl part is $C_6$–$C_{14}$ and is unsubstituted or has at least one substituent selected from the group consisting of substituents (a) defined below and the alkanoyl part is $C_2$–$C_6$,
arylalkenoyl groups in which the aryl part is $C_6$–$C_{14}$ and is unsubstituted or has at least one substituent selected from the group consisting of substituents (a) defined below and the alkenoyl part is $C_3$–$C_6$,
$C_2$–$C_7$ alkoxycarbonyl groups,
$C_7$–$C_{15}$ aryloxycarbonyl groups,
substituted $C_7$–$C_{15}$ aryloxycarbonyl groups having at least one substituent selected from the group consisting of substituents (a) defined below,
$C_8$–$C_{20}$ aralkyloxycarbonyl groups,
substituted $C_8$–$C_{20}$ aralkyloxycarbonyl groups having at least one substituent selected from the group consisting of substituents (a) defined below,
groups of formula —$CONR^6R^7$,
groups of formula —$CSNR^6R^7$,
$C_1$–$C_6$ alkylsulfonyl groups,
$C_1$–$C_6$ haloalkylsulfonyl groups,
$C_6$–$C_{14}$ arylsulfonyl groups,
substituted $C_6$–$C_{14}$ arylsulfonyl groups having at least one substituent selected from the group consisting of substituents (a) defined below,
$C_1$–$C_6$ alkylthio groups,
$C_6$–$C_{14}$ arylthio groups and
substituted $C_6$–$C_{14}$ arylthio groups having at least one substituent selected from the group consisting of substituents (a) defined below;
or $R^1$ and $R^2$, together with the nitrogen atom to which they are attached, form a nitrogen-containing heterocyclic group having from 5 to 8 ring atoms, of which 0 or 1 is an additional hetero-atom selected from the group consisting of nitrogen, oxygen and sulfur hetero-atoms, said heterocyclic group being unsubstituted or having at least one substituent selected from the group consisting of substituents (b) defined below, or form such a heterocyclic group fused to at least one benzene or naphthalene ring system which ring system is unsubstituted or has at least one substituent selected from the group consisting of substituents (c) defined below;

one of $R^a$ and $R^b$ represents a hydrogen atom, a $C_1$-$C_6$ alkyl group or a halogen atom, and the other of $R^a$ and $R^b$ represents a group of formula (II):

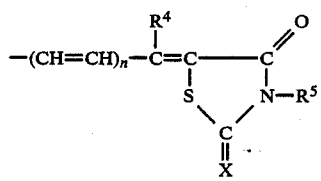

$R^4$ represents a hydrogen atom, a carboxy group, a protected carboxy group or a group of formula —$CONR^8R^9$;

$R^5$ represents a hydrogen atom, or a carboxyalkyl or protected carboxyalkyl group in which the alkyl part is $C_1$-$C_6$;

$n = 0, 1$ or $2$;

X represents an oxygen or sulfur atom;

$R^6$ and $R^7$ are independently selected from the group consisting of:
 hydrogen atoms,
 $C_1$-$C_6$ alkyl groups,
 $C_3$-$C_6$ alkenyl groups,
 $C_3$-$C_8$ cycloalkyl groups,
 $C_6$-$C_{14}$ aryl groups,
 substituted $C_6$-$C_{14}$ aryl groups having at least one substituent selected from the group consisting of substituents (c) defined below,
 $C_7$-$C_{19}$ aralkyl groups,
 substituted $C_7$-$C_{19}$ aralkyl groups having at least one substituent selected from the group consisting of substituents (c) defined below,
 $C_1$-$C_6$ alkylsulfonyl groups,
 $C_1$-$C_6$ haloalkylsulfonyl groups,
 $C_6$-$C_{14}$ arylsulfonyl groups,
 substituted $C_6$-$C_{14}$ arylsulfonyl groups having at least one substituent selected from the group consisting of substituents (c) defined below,
 $C_1$-$C_{12}$ alkanoyl groups,
 $C_4$-$C_9$ cycloalkylcarbonyl groups,
 $C_7$-$C_{15}$ arylcarbonyl groups,
 substituted $C_7$-$C_{15}$ arylcarbonyl groups having at least one substituent selected from the group consisting of substituents (c) defined below;

$R^8$ and $R^9$ are independently selected from the group consisting of hydrogen atoms and $C_1$-$C_6$ alkyl groups;

substituents (a):
 $C_1$-$C_8$ alkyl groups,
 $C_1$-$C_6$ haloalkyl groups,
 $C_6$-$C_{14}$ aryl groups,
 $C_7$-$C_{19}$ aralkyl groups,
 $C_1$-$C_{12}$ alkanoyl groups,
 $C_7$-$C_{15}$ arylcarbonyl groups,
 $C_2$-$C_7$ alkoxycarbonyl groups,
 $C_7$-$C_{15}$ aryloxycarbonyl groups,
 $C_8$-$C_{20}$ aralkyloxycarbonyl groups,
 groups of formula —$CONR^{10}R^{11}$,
 groups of formula —$CSNR^{10}R^{11}$, (where $R^{10}$ and $R^{11}$ are independently selected from the group consisting of hydrogen atoms, $C_1$-$C_6$ alkyl groups and $C_6$-$C_{14}$ aryl groups),
 groups of formula —$NR^{12}R^{13}$, (where $R^{12}$ and $R^{13}$ are independently selected from the group consisting of hydrogen atoms, $C_1$-$C_6$ alkyl groups, $C_6$-$C_{14}$ aryl groups, $C_1$-$C_6$ alkanoyl groups and $C_7$-$C_{15}$ arylcarbonyl groups),
 halogen atoms,
 nitro groups,
 cyano groups,
 hydroxy groups,
 $C_1$-$C_6$ alkoxy groups,
 $C_6$-$C_{14}$ aryloxy groups,
 $C_1$-$C_{12}$ alkanoyloxy groups,
 $C_7$-$C_{12}$ arylcarbonyloxy groups,
 $C_2$-$C_7$ alkoxycarbonyloxy groups,
 $C_7$-$C_{15}$ aryloxycarbonyloxy groups,
 $C_8$-$C_{20}$ aralkyloxycarbonyloxy groups,
 carboxy groups,
 sulfo groups, and
 sulfamoyl groups;

substituents (b):
 oxygen atoms,
 halogen atoms,
 $C_1$-$C_6$ alkyl groups,
 $C_6$-$C_{14}$ aryl groups,
 substituted $C_6$-$C_{14}$ aryl groups having at least one substituent selected from the group consisting of substituents (c) defined below,
 $C_7$-$C_{19}$ aralkyl groups,
 substituted $C_7$-$C_{19}$ aralkyl groups having at least one substituent selected from the group consisting of substituents (c) defined below,
 $C_1$-$C_6$ alkanoyl groups,
 $C_7$-$C_{15}$ arylcarbonyl groups and
 substituted $C_7$-$C_{15}$ arylcarbonyl groups having at least one substituent selected from the group consisting of substituents (c) defined below;

substituents (c):
 $C_1$-$C_4$ alkyl groups,
 $C_1$-$C_4$ alkoxy groups,
 $C_6$-$C_{10}$ aryl groups,
 $C_6$-$C_{10}$ aryloxy groups,
 $C_1$-$C_6$ alkanoyloxy groups,
 halogen atoms,
 hydroxy groups,
 cyano groups,
 trifluoromethyl groups,
 carboxy groups, and
 nitro groups;

or a pharmaceutically acceptable salt or ester thereof.

27. The composition of claim 26, wherein:
$R^1$ and $R^2$ are independently selected from the group consisting of:
 hydrogen atoms,
 $C_1$-$C_8$ alkyl groups,
 $C_3$-$C_6$ alkenyl groups,
 $C_3$-$C_8$ cycloalkyl groups.
 $C_6$-$C_{14}$ aryl groups, substituted $C_6$-$C_{14}$ aryl groups having at least one substituent selected from the group consisting of substituents ($a^1$) defined below, aralkyl and substituted aralkyl groups with from 1 to 3 aryl parts each of which is $C_6$-$C_{10}$ and an alkyl part which is $C_1$-$C_3$, and said substituted aralkyl groups having at least one substituent selected from the group consisting of substituents ($a^1$) defined below, $C_1$-$C_6$ alkanoyl groups, benzoyl groups.

substituted benzoyl groups having at least one substituent selected from the group consisting of substituents ($a^1$) defined below, $C_2$-$C_7$ alkoxycarbonyl groups, groups of formula —$CONR^{6'}R^{7'}$, groups of formula —$CSNR^{6'}R^{7'}$, benzenesulfonyl groups, and toluenesulfonyl groups, or $R^1$ and $R^2$, together with the nitrogen atom to which they are attached, form a nitrogen-containing heterocyclic group having 5 or 6 ring atoms, of which 0 or 1 is an additional hetero-atom selected from the group consisting of nitrogen, oxygen and sulfur hetero-atoms, said heterocyclic group being unsubstituted or having at least one substituent selected from the group consisting of substituents ($b^1$) defined below, or form such a heterocyclic group fused to at least one benzene ring system which ring system is unsubstituted or has at least one substituent selected from the group consisting of substituents ($c^1$) defined below;

one of $R^a$ and $R^b$ represents a hydrogen atom, and the other of $R^a$ and $R^b$ represents a group of formula (II), defined in claim 26;

$R^4$ represents a hydrogen atom, a $C_2$-$C_5$ alkoxycarbonyl group or a benzyloxycarbonyl group;

$R^5$ represents a hydrogen atom, a carboxymethyl group or a protected carboxymethyl group, in which the protecting group is a $C_1$-$C_4$ alkyl group, a benzyl group or a group capable of being hydrolyzed in vivo;

n=0 or 1;

X represents a sulfur atom;

$R^{6'}$ and $R^{7'}$ are independently selected from the group consisting of:

hydrogen atoms, $C_1$-$C_6$ alkyl groups, $C_3$-$C_6$ alkenyl groups, $C_3$-$C_8$ cycloalkyl groups, $C_6$-$C_{14}$ aryl groups, benzyl groups, substituted $C_6$-$C_{14}$ aryl groups having at least one substituent selected from the group consisting of substituents ($c^1$) defined below, benzenesulfonyl groups, toluenesulfonyl groups, $C_2$-$C_6$ alkanoyl groups, and $C_7$-$C_{11}$ arylcarbonyl groups, substituents ($a^1$):

$C_1$-$C_6$ alkyl groups, trifluoromethyl groups, $C_6$-$C_{10}$ aryl groups, $C_7$-$C_{12}$ aralkyl groups, $C_1$-$C_6$ alkanoyl groups, $C_7$-$C_{11}$ arylcarbonyl groups, $C_2$-$C_7$ alkoxycarbonyl groups, groups of formula —$CONR^{10'}R^{11'}$, groups of formula —$CSNR^{10'}R^{11'}$, (where $R^{10'}$ and $R^{11'}$ are independently selected from the group consisting of hydrogen atoms, $C_1$-$C_6$ alkyl groups and $C_6$-$C_{10}$ aryl groups), groups of formula —$NR^{12'}R^{13'}$, (where $R^{12'}$ and $R^{13'}$ are independently selected from the group consisting of hydrogen atoms, $C_1$-$C_6$ alkyl groups, phenyl groups, $C_1$-$C_6$ alkanoyl groups and benzoyl groups), halogen atoms, nitro groups, cyano groups, hydroxy groups, $C_1$-$C_6$ alkoxy groups, phenoxy groups, $C_1$-$C_6$ alkanoyloxy groups, benzoyloxy groups, $C_2$-$C_7$ alkoxycarbonyloxy groups, and carboxy groups;

substituents ($b^1$):

oxygen atoms, $C_1$-$C_4$ alkyl groups, phenyl groups.

benzyl groups, $C_1$-$C_6$ alkanoyl groups, and benzoyl groups;

substituents ($c^1$):

$C_1$-$C_4$ alkyl groups, $C_1$-$C_4$ alkoxy groups, halogen atoms, trifluoromethyl groups, and nitro groups;

provided that, when $R^1$ represents said alkanoyl, benzoyl, substituted benzoyl, alkoxycarbonyl, benzenesulfonyl or toluenesulfonyl group or said group of formula —$CONR^{6'}R^{7'}$ or —$CSNR^{6'}R^{7'}$, then $R^2$ represents said hydrogen atom or said alkyl, alkenyl, cycloalkyl, aryl, substituted aryl, aralkyl or substituted aralkyl group.

28. The composition of claim 26, in which said active compound is represented by the formula (Ia):

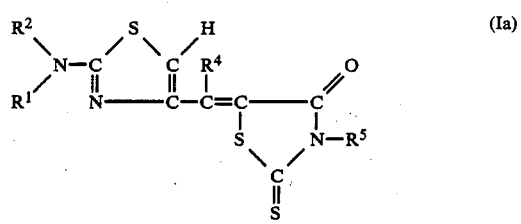

in which $R^1$ and $R^2$ are independently selected from the group consisting of:

hydrogen atoms, $C_1$-$C_6$ alkyl groups, $C_3$-$C_6$ alkenyl groups, $C_3$-$C_6$ cycloalkyl groups, phenyl groups, naphthyl groups, substituted phenyl groups and substituted naphthyl groups having at least one substituent selected from the group consisting of substituents ($a^2$) defined below, $C_2$-$C_6$ alkanoyl groups, $C_7$-$C_{19}$ aralkyl groups, $C_7-C_{19}$ substituted aralkyl groups having at least one substituent selected from the group consisting of substituents ($a^2$) defined below,
benzoyl groups,
substituted benzoyl groups having at least one substituent selected from the group consisting of substituents ($a^2$) defined below,
groups of formula $-CONR^{6''}R^{7''}$, and
groups of formula $-CSNR^{6''}R^{7''}$, or $R^1$ and $R^2$, together with the nitrogen atom to which hey are attached, form a 1-pyrrolidinyl, piperidino, hexamethyleneimino, morpholino, thiomorpholino or 1-piperazinyl group which is unsubstituted or has at least one substituent selected from the group consisting of substituents ($b^2$) defined below;
$R^4$ represents a hydrogen atom or a $C_2-C_5$ alkoxycarbonyl group;
$R^5$ represents a hydrogen atom, a carboxymethyl group or a protected carboxymethyl group, in which the protecting group is a $C_1-C_4$ alkyl group, a benzyl group or a group capable of being hydrolyzed in vivo:
$R^{6''}$ and $R^{7''}$ are independently selected from the group consisting of:
hydrogen atoms,
$C_1-C_6$ alkyl groups,
allyl groups,
cyclohexyl groups,
$C_6-C_{10}$ aryl groups,
substituted $C_6-C_{10}$ aryl groups having at least one substituent selected from the group consisting of substituents ($c^2$) defined below,
benzenesulfonyl groups.
toluenesulfonyl groups, and
benzoyl groups,
substituents ($a^2$)
$C_1-C_6$ alkyl groups.
trifluoromethyl groups,
phenyl groups,
halogen atoms, and
$C_1-C_6$ alkoxy groups;
substituents ($b^2$):
$C_1-C_4$ alkyl groups,
phenyl groups,
benzyl groups,
$C_1-C_6$ alkanoyl groups, and
benzoyl groups;
substituents ($c^2$):
$C_1-C_4$ alkyl groups,
$C_1-C_4$ alkoxy groups,
halogen atoms,
nitro groups, and
trifluoromethyl groups;
provided that, when $R^1$ represents a hydrogen atom then $R^2$ represents a group other than a hydrogen atom, and, when $R^1$ represents said alkanoyl, benzoyl or substituted benzoyl group or said group of formula $-CONR^{6''}R^{7''}$ or $-CSNR^{6''}R^{7''}$, then $R^2$ represents said hydrogen atom or said alkyl, alkenyl, cycloalkyl, phenyl. naphthyl, substituted phenyl, substituted naphthyl, aralkyl or substituted aralkyl group;
or is a pharmaceutically acceptable salt or ester thereof.

29. The composition of claim 28, wherein:
$R^1$ and $R^2$ are independently selected from the group consisting of:
hydrogen atoms,
$C_1-C_4$ alkyl groups,
$C_3-C_6$ alkenyl groups,
$C_3-C_6$ cycloalkyl groups,
phenyl groups.
substituted phenyl groups having at least one substituent selected from the group consisting of $C_1-C_4$ alkyl groups, $C_1-C_4$ alkoxy groups, halogen atoms and trifluoromethyl groups,
monoarylcarbamoyl and monoaryl(thiocarbamoyl) groups in which the aryl group is a $C_6-C_{10}$ carbocyclic aryl group which is unsubstituted or has at least one substituent selected from the group consisting of $C_1-C_4$ alkyl groups, $C_1-C_4$ alkoxy groups, halogen atoms, trifluoromethyl groups and nitro groups,
$R^4$ represents a hydrogen atom or a $C_2-C_5$ alkoxycarbonyl group;
$R^5$ represents a hydrogen atom, a carboxymethyl group or a protected carboxymethyl group, in which the protecting group is a $C_1-C_4$ alkyl group, a benzyl group or a group capable of being hydrolyzed in vivo;
provided that, when $R^1$ represents a hydrogen atom then $R^2$ represents a group other than a hydrogen atom, and, when $R^1$ represents said monoarylcarbamoyl or monoaryl(thiocarbamoyl) group, then $R^2$ represents said hydrogen atom or said alkyl, alkenyl, phenyl or substituted phenyl group.

30. The composition of claim 28, in which said active compound is represented by the formula (Ib):

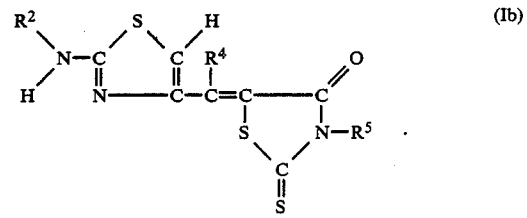

in which:
$R^2$ represents
a $C_1-C_4$ alkyl group,
a $C_3-C_6$ alkenyl group,
a phenyl group,
a substituted phenyl group having at least one substituent selected from the group consisting of $C_1-C_4$ alkyl groups, $C_1-C_4$ alkoxy groups, halogen atoms and trifluoromethyl groups, or
a phenylcarbamoyl group or a phenyl(thiocarbamoyl) group in which the phenyl group is unsubstituted or has at least one substituent selected from the group consisting of $C_1-C_4$ alkyl groups, $C_1-C_4$ alkoxy groups, halogen atoms, trifluoromethyl groups and nitro groups,
$R^4$ represents a hydrogen atom or a $C_2-C_5$ alkoxycarbonyl group;
$R^5$ represents a carboxymethyl group.

31. The composition of claim 26, wherein said active compound is selected from the group consisting of:
5-{1-ethoxycarbonyl-1-[2-(3-phenylureido)thiazol-4-yl]methylene}rhodanine-3-acetic acid;
5-[2-(3-phenylureido)thiazol-4-ylmethylene]rhodanine-3-acetic acid;
5-{1'-ethoxycarbonyl-1-[2-[3-(1-naphthyl)ureido]-thiazol-4-yl]methylene}rhodanine-3-acetic acid;

5-{1-[2-(3-p-chlorophenylureido)thiazol-4-yl]-1-ethoxycarbonylmethylene}rhodanine-3-acetic acid;

5-{1-[2-(3-p-fluorophenylureido)thiazol-4-yl]-1-ethoxycarbonylmethylene}rhodanine-3-acetic acid;

5-{1-ethoxycarbonyl-1-[2-[3-(4-fluoro-3-nitrophenyl)ureido]thiazol-4-yl]methylene}rhodanine-3-acetic acid;

5-{1-ethoxycarbonyl-1-[2-[3-(2,4,6-trifluorophenyl)ureido]thiazol-4-yl]methylene}rhodanine-3-acetic acid:

5-{1-ethoxycarbonyl-1-[2-(3-phenylthioureido)-thiazol-4-yl]methylene}rhodanine-3-acetic acid;

5-{1-[2-(3-p-chlorophenylthioureido)thiazol-4-yl]-1-ethoxycarbonylmethylene}rhodanine-3-acetic acid;

5-(2-ethylaminothiazol-4-ylmethylene)rhodanine-3-acetic acid;

5-(2-isopropylaminothiazol-4-ylmethylene)rhodanine-3-acetic acid;

5-(2-allylaminothiazol-4-ylmethylene)rhodanine-3-acetic acid;

5-(2-cyclopropylaminothiazol-4-ylmethylene)rhodanine-3-acetic acid;

and pharmaceutically acceptable salts and esters thereof.

32. A method for the treatment or prophylaxis of the complications of diabetes in a mammal suffering from diabetes by administering thereto an effective amount of at least one active compound, in which said active compound is a compound of formula (I):

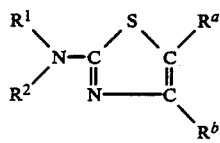

in which:

$R^1$ and $R^2$ are independently selected from the group consisting of:
hydrogen atoms,
$C_1$-$C_{12}$ alkyl groups,
$C_3$-$C_6$ aliphatic hydrocarbon groups having one or two carbon-carbon double or treble bonds,
$C_3$-$C_8$ cycloalkyl groups,
$C_6$-$C_{14}$ aryl groups,
substituted $C_6$-$C_{14}$ aryl groups having at least one substituent selected from the group consisting of substituents (a) defined below,
aralkyl and substituted aralkyl groups with from 1 to 3 aryl parts each of which is $C_6$-$C_{14}$ and an alkyl part which is $C_1$-$C_5$, and said substituted aralkyl groups having at least one substituent selected from the group consisting of substituents (a) defined below,
$C_1$-$C_{12}$ alkanoyl groups,
$C_3$-$C_{12}$ alkenoyl groups,
$C_4$-$C_9$ cycloalkylcarbonyl groups,
$C_7$-$C_{15}$ arylcarbonyl groups,
substituted $C_7$-$C_{15}$ arylcarbonyl groups having at least one substituent selected from the group consisting of substituents (a) defined below.
arylalkanoyl groups in which the aryl part is $C_6$-$C_{14}$ and is unsubstituted or has at least one substituent selected from the group consisting of substituents (a) defined below and the alkanoyl part is $C_2$-$C_6$,
arylalkenoyl groups in which the aryl part is $C_6$-$C_{14}$ and is unsubstituted or has at least one substituent selected from the group consisting of substituents (a) defined below and the alkenoyl part is $C_3$-$C_6$,
$C_2$-$C_7$ alkoxycarbonyl groups,
$C_7$-$C_{15}$ aryloxycarbonyl groups,
substituted $C_7$14 $C_{15}$ aryloxycarbonyl groups having at least one substituent selected from the group consisting of substituents (a) defined below,
$C_8$-$C_{20}$ aralkyloxycarbonyl groups,
substituted $C_8$-$C_{20}$ aralkyloxycarbonyl groups having at least one substituent selected from the group consisting of substituents (a) defined below,
groups of formula —$CONR^6R^7$,
groups of formula —$CSNR^6R^7$,
$C_1$-$C_6$ alkylsulfonyl groups,
$C_1$-$C_6$ haloalkylsulfonyl groups,
$C_6$-$C_{14}$ arylsulfonyl groups,
substituted $C_6$-$C_{14}$ arylsulfonyl groups having at least one substituent selected from the group consisting of substituents (a) defined below;
$C_1$-$C_6$ alkylthio groups,
$C_6$-$C_{14}$ arylthio groups and
substituted $C_6$-$C_{14}$ arylthio groups having at least one substituent selected from the group consisting of substituents (a) defined below;
or $R^1$ and $R^2$, together with the nitrogen atom to which they are attached, form a nitrogen-containing heterocyclic group having from 5 to 8 ring atoms, of which 0 or 1 is an additional hetero-atom selected from the group consisting of nitrogen, oxygen and sulfur hetero-atoms, said heterocyclic group being unsubstituted or having at least one substituent selected from the group consisting of substituents (b) defined below, or form such a heterocyclic group fused to at least one benzene or naphthalene ring system which ring system is unsubstituted or has at least one substituent selected from the group consisting of substituents (c) defined below;
one of $R^a$ and $R^b$ represents a hydrogen atom, a $C_1$-$C_6$ alkyl group or a halogen atom, and the other of $R^a$ and $R^b$ represents a group of formula (II):

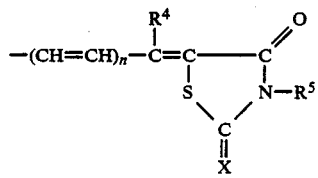

$R^4$ represents a hydrogen atom, a carboxy group, a protected carboxy group or a group of formula —$CONR^8R^9$;
$R^5$ represents a hydrogen atom, or a carboxyalkyl or protected carboxyalkyl group in which the alkyl part is $C_1$-$C_6$;
n=0, 1 or 2;
X represents an oxygen or sulfur atom;
$R^6$ $R^7$ are independently selected from the group consisting of:

hydrogen atoms,
$C_1$-$C_6$ alkyl groups,
$C_3$-$C_6$ alkenyl groups,
$C_3$-$C_8$ cycloalkyl groups,
$C_6$-$C_{14}$ aryl groups,
substituted $C_6$-$C_{14}$ aryl groups having at least one substituent selected from the group consisting of substituents (c) defined below,
$C_7$-$C_{19}$ aralkyl groups,
substituted $C_7$-$C_{19}$ aralkyl groups having at least one substituent selected from the group consisting of substituents (c) defined below,
$C_1$-$C_6$ alkylsulfonyl groups,
$C_1$-$C_6$ haloalkylsulfonyl groups,
$C_6$-$C_{14}$ arylsulfonyl groups,
substituted $C_6$-$C_{14}$ arylsulfonyl groups having at least one substituent selected from the group consisting of substituents (c) defined below,
$C_1$-$C_{12}$ alkanoyl groups,
$C_4$-$C_9$ cycloalkylcarbonyl groups,
$C_7$-$C_{15}$ arylcarbonyl groups,
substituted $C_7$-$C_{15}$ arylcarbonyl groups having at least one substituent selected from the group consisting of substituents (c) defined below;
$R^8$ and $R^9$ are independently selected from the group consisting of hydrogen atoms and $C_1$-$C_6$ alkyl groups;

substituents (a):
$C_1$-$C_8$ alkyl groups,
$C_1$-$C_6$ haloalkyl groups,
$C_6$-$C_{14}$ aryl groups,
$C_7$-$C_{19}$ aralkyl groups,
$C_1$-$C_{12}$ alkanoyl groups,
$C_7$-$C_{15}$ arylcarbonyl groups,
$C_2$-$C_7$ alkoxycarbonyl groups,
$C_7$-$C_{15}$ aryloxycarbonyl groups,
$C_8$-$C_{20}$ aralkyloxycarbonyl groups,
groups of formula —$CONR^{10}R^{11}$,
groups of formula —$CSNR^{10}R^{11}$, (where $R^{10}$ and $R^{11}$ are independently selected from the group consisting of hydrogen atoms, $C_1$-$C_6$ alkyl groups and $C_6$-$C_{14}$ aryl groups),
groups of formula —$NR^{12}R^{13}$, (where $R^{12}$ and $R^{13}$ are independently selected from the group consisting of hydrogen atoms, Chd $1$-$C_6$ alkyl groups, $C_6$-$C_{14}$ aryl groups, $C_1$-$C_6$ alkanoyl groups and $C_7$-$C_{15}$ arylcarbonyl groups),
halogen atoms,
nitro groups,
cyano groups,
hydroxy groups,
$C_1$-$C_6$ alkoxy groups,
$C_6$-$C_{14}$ aryloxy groups,
$C_1$-$C_{12}$ alkanoyloxy groups,
$C_7$-$C_{15}$ arylcarbonyloxy groups,
$C_2$-$C_7$ alkoxycarbonyloxy groups,
$C_7$-$C_{15}$ aryloxycarbonyloxy groups,
$C_8$-$C_{20}$ aralkyloxycarbonyloxy groups,
carboxy groups,
sulfo groups, and
sulfamoyl groups;

substituents (b):
oxygen atoms,
halogen atoms,
$C_1$-$C_6$ alkyl groups,
$C_6$-$C_{14}$ aryl groups,
substituted $C_6$-$C_{14}$ aryl groups having at least one substituent selected from the group consisting of substituents (c) defined below,
$C_7$-$C_{19}$ aralkyl groups,
substituted $C_7$-$C_{19}$ aralkyl groups having at least one substituent selected from the group consisting of substituents (c) defined below,
$C_1$-$C_6$ alkanoyl groups,
$C_7$-$C_{15}$ arylcarbonyl groups and
substituted $C_7$-$C_{15}$ arylcarbonyl groups having at least one substituent selected from the group consisting of substituents (c) defined below;

substituents (c):
$C_1$-$C_4$ alkyl groups,
$C_1$-$C_4$ alkoxy groups,
$C_6$-$C_{10}$ aryl groups,
$C_6$-$C_{10}$ aryloxy groups,
$C_1$-$C_6$ alkanoyloxy groups,
halogen atoms,
hydroxy groups,
cyano groups,
trifluoromethyl groups,
carboxy groups, and
nitro groups;
or a pharmaceutically acceptable salt or ester thereof.

33. The method of claim 32, wherein:
$R^1$ and $R^2$ are independently selected from the group consisting of:
hydrogen atoms,
$C_1$-$C_8$ alkyl groups,
$C_3$-$C_6$ alkenyl groups,
$C_3$-$C_8$ cycloalkyl groups,
$C_6$-$C_{14}$ aryl groups,
substituted $C_6$-$C_{14}$ aryl groups having at least one substituent selected from the group consisting of substituents ($a^1$) defined below,
aralkyl and substituted aralkyl groups with from 1 to 3 aryl parts each of which is $C_6$-$C_{10}$ and an alkyl part which is $C_1$-$C_3$, and said substituted aralkyl groups having at least one substituent selected from the group consisting of substituents ($a^1$) defined below,
$C_1$-$C_6$ alkanoyl groups,
benzoyl groups,
substituted benzoyl groups having at least one substituent selected from the group consisting of substituents ($a^1$) defined below,
$C_2$-$C_7$ alkoxycarbonyl groups,
groups of formula —$CONR^{6'}R^{7'}$,
groups of formula —$CSNR^{6'}R^{7'}$,
benzenesulfonyl groups, and
toluenesulfonyl groups,
or $R^1$ and $R^2$, together with the nitrogen atom to which they are attached, form a nitrogen-containing heterocyclic group having 5 or 6 ring atoms, of which 0 or 1 is an additional hetero-atom selected from the group consisting of nitrogen, oxygen and sulfur hetero-atoms, said heterocyclic group being unsubstituted or having at least one substituent selected from the group consisting of substituents ($b^1$) defined below, or form such a heterocyclic group fused to at least one benzene ring system which ring system is unsubstituted or has at least one substituent selected from the group consisting of substituents ($c^1$) defined below;
one of $R^a$ and $R^b$ represents a hydrogen atom, and the other of $R^a$ and $R^b$ represents a group of formula (II), defined in claim 32;

R[4] represents a hydrogen atom, a C2–C5 alkoxycarbonyl group or a benzyloxycarbonyl group;

R[5] represents a hydrogen atom, a carboxymethyl group or a protected carboxymethyl group, in which the protecting group is a C1–C4 alkyl group, a benzyl group or a group capable of being hydrolyzed in vivo;

n=0 or 1;

X represents a sulfur atom;

R[6'] [7'] are independently selected from the group consisting of:
hydrogen atoms,
C1–C6 alkyl groups,
C3–C6 alkenyl groups,
C3–C8 cycloalkyl groups,
C6–C14 aryl groups,
benzyl groups,
substituted C6–C14 aryl groups having at least one substituent selected from the group consisting of substituents (c[1]) defined below,
benzenesulfonyl groups,
toluenesulfonyl groups,
C2–C6 alkanoyl groups, and
C7–C11 arylcarbonyl groups, substituents (a[1]):
C1–C6 alkyl groups,
trifluoromethyl groups,
C6–C10 aryl groups,
C7–C12 aralkyl groups,
C1–C6 alkanoyl groups,
C7–C11 arylcarbonyl groups.
C2–C7 alkoxycarbonyl groups,
groups of formula —CONR[10']R[11'],
groups of formula —CSNR[10']R[11'],
(where R[10'] and R[11'] are independently selected from the group consisting of hydrogen atoms, C1–C6 alkyl groups and C6–C10 aryl groups).
groups of formula —NR[12']R[13'],
(Where R[12'] and R[13'] are independently selected from the group consisting of hydrogen atoms, C1–C6 alkyl groups, phenyl groups, C1–C6 alkanoyl groups and benzoyl groups),
halogen atoms,
nitro groups,
cyano groups,
hydroxy groups,
C1–C6 alkoxy groups,
phenoxy groups,
C1–C6 alkanoyloxy groups,
benzoyloxy groups,
C2–C7 alkoxycarbonyloxy groups, and
carboxy groups;

substituents (b[1]):
oxygen atoms,
C1–C4 alkyl groups,
phenyl groups,
benzyl groups,
C1–C6 alkanoyl groups, and
benzoyl groups;

substituents (c[1]):
C1–C4 alkyl groups,
C1–C4 alkoxy groups,
halogen atoms,
trifluoromethyl groups, and
nitro groups;

provided that, when R[1] represents said alkanoyl, benzoyl, substituted benzoyl, alkoxycarbonyl, benzenesulfonyl or toluenesulfonyl group or said group of formula —CONR[6']R[7'] or —CSNR[6']R[7'], then R[2] represents said hydrogen atom or said alkyl, alkenyl, cycloalkyl, aryl, substituted aryl, aralkyl or substituted aralkyl group.

34. The method of claim 32, in which said active compound is represented by the formula (Ia):

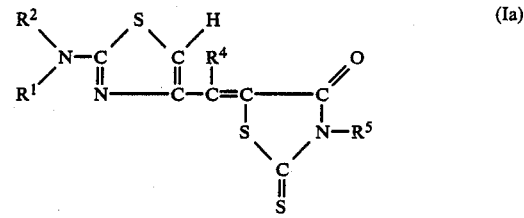

in which:

R[1] and R[2] are independently selected from the group consisting of:
hydrogen atoms,
C1–C6 alkyl groups,
C3–C6 alkenyl groups,
C3–C6 cycloalkyl groups,
phenyl groups,
naphthyl groups,
substituted phenyl groups and substituted naphthyl groups having at least one substituent selected from the group consisting of substituents (a[2]) defined below,
C2–C6 alkanoyl groups,
C7–C19 aralkyl groups,
C7–C19 substituted aralkyl groups having at least one substituent selected from the group consisting of substituents (a[2]) defined below,
benzoyl groups,
substituted benzoyl groups having at least one substituent selected from the group consisting of substituents (a[2]) defined below,
groups of formula —CONR[6"]R[7"], and
groups of formula —CSNR[6"]R[7"], or R[1] and R[2], together with the nitrogen atom to which they are attached, form a 1-pyrrolidinyl, piperidino, hexamethyleneimino, morpholino, thiomorpholino or 1-piperazinyl group which is unsubstituted or has at least one substituent selected from the group consisting of substituents (b[2]) defined below;

R[4] represents a hydrogen atom or a C2–C5 alkoxycarbonyl group;

R[5] represents a hydrogen atom, a carboxymethyl group or a protected carboxymethyl group, in which the protecting group is a C1–C4 alkyl group, a benzyl group or a group capable of being hydrolyzed in vivo;

R[6"] and R[7"] are independently selected from the group consisting of:
hydrogen atoms,
C1–C6 alkyl groups,
allyl groups,
cyclohexyl groups,
C6–C10 aryl groups,
substituted C6–C10 aryl groups having at least one substituent selected from the group consisting of substituents (c[2]) defined below,
benzenesulfonyl groups,
toluenesulfonyl groups, and benzoyl groups.
substituents (a²):
C₁–C₆ alkyl groups,
trifluoromethyl groups,
phenyl groups,
halogen atoms, and
C₁–C₆ alkoxy groups;
substituents (b²):
C₁–C₄ alkyl groups,
phenyl groups,
benzyl groups,
C₁–C₆ alkanoyl groups, and
benzoyl groups;
substituents (c²):
C₁–C₄ alkyl groups,
C₁–C₄ alkoxy groups,
halogen atoms,
nitro groups, and
trifluoromethyl groups;
provided that, when R¹ represents a hydrogen atom then R² represents a group other than a hydrogen atom, and, when R¹ represents said alkanoyl, benzoyl or substituted benzoyl group or said group of formula —CONR⁶″R⁷″ or —CSNR⁶″R⁷″, then R² represents said hydrogen atom or said alkyl, alkenyl, cycloalkyl, phenyl, naphthyl, substituted phenyl, substituted naphthyl, aralkyl or substituted aralkyl group;
or is a pharmaceutically acceptable salt or ester thereof.

35. The method of claim 34, wherein:
R¹ and R² are independently selected from the group consisting of:
hydrogen atoms,
C₁–C₄ alkyl groups,
C₃–C₆ alkenyl groups,
C₃–C₆ cycloalkyl groups,
phenyl groups,
substituted phenyl groups having at least one substituent selected from the group consisting of C₁–C₄ alkyl groups, C₁–C₄ alkoxy groups, halogen atoms and trifluoromethyl groups,
monoarylcarbamoyl and monoaryl(thiocarbamoyl) groups in which the aryl group is a C₆–C₁₀ carbocyclic aryl group which is unsubstituted or has at least one substituent selected from the group consisting of C₁–C₄ alkyl groups, C₁–C₄ alkoxy groups, halogen atoms, trifluoromethyl groups and nitro groups,
R⁴ represents a hydrogen atom or a C₂–C₅ alkoxycarbonyl group;
R⁵ represents a hydrogen atom, a carboxymethyl group of a protected carboxymethyl group, in which the protecting group is a C₁–C₄ alkyl group, a benzyl group or a group capable of being hydrolyzed in vivo;
provided that, when R¹ represents a hydrogen atom then R² represents a group other than a hydrogen atom, and, when R¹ represents said monoarylcarbamoyl or monoaryl(thiocarbamoyl) group, then R² represents said hydrogen atom or said alkyl, alkenyl, phenyl or substituted phenyl group.

36. The method of claim 34, in which said active compound is represented by the formula (Ib):

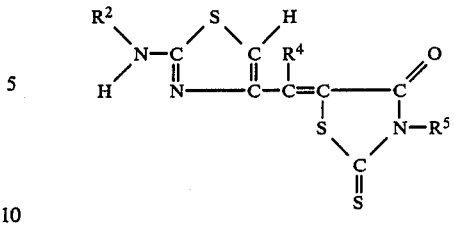

in which:
R² represents
a C₁–C₄ alkyl group,
a C₃–C₆ alkenyl group,
a phenyl group,
a substituted phenyl group having at least one substituent selected from the group consisting of C₁–C₄ alkyl groups, C₁–C₄ alkoxy groups, halogen atoms and trifluoromethyl groups, or
a phenylcarbamoyl group or a phenyl(thiocarbamoyl) group in which the phenyl group is unsubstituted or has at least one substituent selected from the group consisting of C₁–C₄ alkyl groups, C₁–C₄ alkoxy groups, halogen atoms, trifluoromethyl groups and nitro groups,
R⁴ represents a hydrogen atom or a C₂–C₅ alkoxycarbonyl group;
R⁵ represents a carboxymethyl group;
or is a pharmaceutically acceptable salt or ester thereof.

37. The method of claim 32, wherein said active compound is selected from the group consisting of:
5-{1-ethoxycarbonyl-1-[2-(3-phenylureido)thiazol-4-yl]methylene}rhodanine-3-acetic acid;
5-[2-(3-phenylureido)thiazol-4-ylmethylene]rhodanine-3-acetic acid;
5-{1-ethoxycarbonyl-1-[2-[3-(1-naphthyl)ureido]-thiazol-4-yl]methylene}rhodanine-3-acetic acid:
5-{1-[2-(3-p-chlorophenylureido)thiazol-4-yl]-1-ethoxycarbonylmethylene}rhodanine-3-acetic acid;
5-{1-[2-(3-p-fluorophenylureido)thiazol-4-yl]-1-ethoxycarbonylmethylene}rhodanine-3-acetic acid;
5-{1-ethoxycarbonyl-1-[2-[3-(4-fluoro-3-nitrophenyl)ureido]thiazol-4-yl]methylene}rhodanine-3-acetic acid;
5-[1-ethoxycarbonyl-1-[2-[3-(2,4,6-trifluorophenyl)ureido]thiazol-4-yl]methylene}rhodanine-3-acetic acid;
5-{1-ethoxycarbonyl-1-[2-(3-phenylthioureido)-thiazol-4-yl]methylene}rhodanine-3-acetic acid;
5-[1-[2-(3-p-chlorophenylthioureido)thiazol-4-yl]-1-ethoxycarbonylmethylene}rhodanine-3-acetic acid;
5-(2-ethylaminothiazol-4-ylmethylene)rhodanine-3-acetic acid;
5-(2-isopropylaminothiazol-4-ylmethylene)rhodanine-3-acetic acid;
5-(2-allylaminothiazol-4-ylmethylene)rhodanine-3-acetic acid;
5-(2-cyclopropylaminothiazol-4-ylmethylene)rhodanine-3-acetic acid;
and pharmaceutically acceptable salts and esters thereof.

* * * * *

UNITED STATES PATENT AND TRADEMARK OFFICE
CERTIFICATE OF CORRECTION

PATENT NO. : 4,933,355
DATED : June 12, 1990
INVENTOR(S) : YOSHIOKA et al

It is certified that error appears in the above-identified patent and that said Letters Patent is hereby corrected as shown below:

In the title page:

Under "FOREIGN PATENT DOCUMENTS", insert -
--FR-A1-2117336 7/1972 France....548/183--

Under "OTHER DOCUMENTS", insert -
--T.E. ACHARY et al, "Studies on thiazolidinones: Part IV. Thiazolidinones and their derivatives from unsymmetrical thioureas", CHEMICAL ABSTRACTS, Vol. 85, No.3, July 19, 1976, Columbus, Ohio USA, page 676, column 1, abstract No.21 190g, & Indiam Chem. Soc. 1975, 52(12), 1204-6--.

Column 4, line 14, change "$C_7$-$C_5$" to --$C_7$-$C_{15}$--.

Column 6, line 29, change "rhe" to --the--.

Column 9, line 22, change "o-" (second occurance)
    to -- m- --.

Column 14, lines 3 and 4 change "arylcarbony)oxy" to
    --arylcarbonyloxy--.

Column 19, line 2, new paragraph starting with the words
    "The compounds".

Column 23, Cpd.No. 2-77 (second line), change "4-(HOPh)"
    to -- 4-HOPh)--.

Column 36, line 17, change " =- 1-[2-(3-o-..." to
    -- 5- 1-[2-(3-o... --.

UNITED STATES PATENT AND TRADEMARK OFFICE
CERTIFICATE OF CORRECTION

PATENT NO. : 4,933,355
DATED : June 12, 1990
INVENTOR(S) : YOSHIOKA et al

It is certified that error appears in the above-identified patent and that said Letters Patent is hereby corrected as shown below:

Column 37, line 34, change "1.05" to --11.05--.

Column 44, line 50, change "yl]met hylene]..." to -- yl]methylene]... --.

Column 45, line 35, change "ellow" to --yellow--.

Column 46, line 20, after "eluent", insert --a 3:1--.

Column 46, line 44, change "guartet" to --quartet--.

Column 49, line 11, change "ml" to --20 ml--.

Column 54, line 49, change "ml" to --2 ml--.

Column 54, line 59, change "0.05" to --10.05--.

Column 55, line 2, change "29 mg" to --290 mg--.

Column 57, line 32, change "anine-acetic" to --anine-3-acetic--.

Column 57, line 63, change "- 1-2-Bis..." to -- 5- 1-[2-Bis...--.

Column 58, line 1, change "thiazol-4-glglyoxylate" to --thiazol-4-ylglyoxylate--.

Column 61, line 52, change "-(2-Octyl..." to --5-(2-Octyl...--.

UNITED STATES PATENT AND TRADEMARK OFFICE
CERTIFICATE OF CORRECTION

PATENT NO. : 4,933,355

DATED : June 12, 1990

INVENTOR(S) : YOSHIOKA et al

It is certified that error appears in the above-identified patent and that said Letters Patent is hereby corrected as shown below:

Column 61, last line, change "3.0-13.6" to --13.00-13.6--.

Column 62, line 17, change "3.0-13.8" to --13.00-13.8--.

Column 80, line 1, change "1 5 g" to --1.5 g--.

Column 89, line 64, change "n=0," to --$\underline{n}$=0,--.

Column 92, line 15, change "$C_7$1-$C_{12}$" to --$C_7$-$C_{12}$--.

Column 92, line 63 (claim 6), change "n=0" to --$\underline{n}$=0--.

Column 93, line 50, change "in vivo" to --$\underline{in}$ $\underline{vivo}$--.

Column 93, line 51, change "n=0" to --$\underline{n}$=0--.

Column 95, line 30, change "in vivo" to --$\underline{in}$ $\underline{vivo}$--.

Column 96, line 31, change "in vivo" to --$\underline{in}$ $\underline{vivo}$--.

Column 100, line 23, change "$C_7$-$C_{12}$" to --$C_7$-$C_{15}$--.

Column 101, line 42, change "in vivo" to --$\underline{in}$ $\underline{vivo}$--.

Column 101, line 43, change "n=0" to --$\underline{n}$=0--.

UNITED STATES PATENT AND TRADEMARK OFFICE
CERTIFICATE OF CORRECTION

PATENT NO.  : 4,933,355
DATED       : June 12, 1990
INVENTOR(S) : YOSHIOKA et al It is certified that error appears in the above-identified patent and that said Letters Patent is hereby corrected as shown below:

Column 103, line 10, change "hey" to --they--.

Column 103, line 23, change "in vivo" to --$\underline{in}$ $\underline{vivo}$--.

Column 104, line 23, change "in vivo" to --$\underline{in}$ $\underline{vivo}$--.

Column 107, line 46, change "Chd 1-$C_6$" to --$C_1$-$C_6$--.

Signed and Sealed this

Fourteenth Day of July, 1992

Attest:

DOUGLAS B. COMER

*Attesting Officer*      *Acting Commissioner of Patents and Trademarks*

UNITED STATES PATENT AND TRADEMARK OFFICE
CERTIFICATE OF CORRECTION

PATENT NO. : 4,933,355
DATED : June 12, 1990
INVENTOR(S) : YOSHIOKA et al

It is certified that error appears in the above-identified patent and that said Letters Patent is hereby corrected as shown below:

Column 97, line 67: after "diluent" insert --,--.

Column 106, line 67: change "$R^6$ $R^7$" to --$R^6$ and $R^7$--.

Column 107, line 5: change "$C_6C_{14}$" to --$C_6$-$C_{14}$--.

Signed and Sealed this

Ninth Day of August, 1994

Attest:

BRUCE LEHMAN

Attesting Officer     Commissioner of Patents and Trademarks